United States Patent
Laughlin, II et al.

(10) Patent No.: US 11,850,299 B2
(45) Date of Patent: *Dec. 26, 2023

(54) SKIN CARE COMPOSITION AND METHOD OF USING THE SAME

(71) Applicant: The Procter & Gamble Company, Cincinnati, OH (US)

(72) Inventors: Leo Timothy Laughlin, II, Mason, OH (US); Michael Joseph Flagler, Anderson Township, OH (US); Lisa Ann Mullins, West Chester, OH (US); Makio Tamura, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,728

(22) Filed: Jan. 4, 2023

(65) Prior Publication Data
US 2023/0165774 A1   Jun. 1, 2023

Related U.S. Application Data

(63) Continuation of application No. 17/155,357, filed on Jan. 22, 2021, now Pat. No. 11,571,378.

(51) Int. Cl.
*A61K 38/00* (2006.01)
*A61K 8/64* (2006.01)
*A61Q 19/00* (2006.01)

(52) U.S. Cl.
CPC ............... *A61K 8/64* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 3,755,560 A | 8/1973 | Dickert et al. | |
| 4,421,769 A | 12/1983 | Dixon et al. | |
| 5,011,681 A | 4/1991 | Ciotti et al. | |
| 5,872,112 A | 2/1999 | Blank | |
| 5,939,082 A | 8/1999 | Oblong et al. | |
| 5,972,359 A | 10/1999 | Sine et al. | |
| 6,174,533 B1 | 1/2001 | Sanogueira, Jr. et al. | |
| 6,492,326 B1 | 12/2002 | Robinson | |
| 6,524,598 B2 | 2/2003 | Sunkel et al. | |
| 6,696,049 B2 | 2/2004 | Vatter | |
| 8,568,751 B1* | 10/2013 | Goldsberry | A61Q 19/08 424/401 |
| 9,192,558 B2 | 11/2015 | Chen et al. | |
| 9,446,265 B2 | 9/2016 | Jansen et al. | |
| 9,511,010 B2 | 12/2016 | Van Den Nest et al. | |
| 9,597,274 B2 | 3/2017 | Idkowiak-baldys et al. | |
| 9,795,552 B2 | 10/2017 | Tanner et al. | |
| 9,833,405 B2 | 12/2017 | Xu et al. | |
| 10,265,348 B2 | 4/2019 | Soley Astals et al. | |
| 10,668,000 B2 | 6/2020 | Peschard et al. | |
| 11,571,378 B2 | 2/2023 | Laughlin, II et al. | |
| 2002/0022040 A1 | 2/2002 | Robinson et al. | |
| 2003/0049212 A1 | 3/2003 | Robinson et al. | |
| 2004/0175347 A1 | 9/2004 | Bissett | |
| 2006/0018860 A1 | 1/2006 | Chen et al. | |
| 2006/0275237 A1 | 12/2006 | Bissett | |
| 2007/0196344 A1 | 8/2007 | Osborne et al. | |
| 2008/0095732 A1 | 4/2008 | Osborne | |
| 2008/0181956 A1 | 7/2008 | Ha et al. | |
| 2008/0206373 A1 | 8/2008 | Millikin et al. | |
| 2009/0111731 A1 | 4/2009 | Imfeld et al. | |
| 2010/0092408 A1 | 4/2010 | Breyfogle | |
| 2010/0098752 A1 | 4/2010 | Pinsky | |
| 2010/0189669 A1 | 7/2010 | Hakozaki | |
| 2010/0227011 A1 | 9/2010 | Kuhlman et al. | |
| 2010/0239510 A1 | 9/2010 | Ha et al. | |
| 2010/0272667 A1 | 10/2010 | Kyte, III et al. | |
| 2011/0097286 A1 | 4/2011 | Swanson | |
| 2011/0262025 A1 | 10/2011 | Jarrold et al. | |
| 2011/0262570 A1 | 10/2011 | Finlay et al. | |
| 2011/0300199 A1 | 12/2011 | Garcia et al. | |
| 2011/0305737 A1 | 12/2011 | Alexiades-armenakas | |
| 2012/0028916 A1 | 2/2012 | Fournial et al. | |
| 2012/0076842 A1 | 3/2012 | Fournial et al. | |
| 2012/0121675 A1 | 5/2012 | Garcia et al. | |

(Continued)

FOREIGN PATENT DOCUMENTS

| | | | |
|---|---|---|---|
| CN | 103767971 A | 5/2014 | |
| CN | 104688622 A | 6/2015 | |

(Continued)

OTHER PUBLICATIONS

Osborne et al. (J Am Acad Dermatol. 2008;58(2): Supplement 2, AB25). In vitro skin structure benefits with a new antiaging peptide, Pal-KT. (Year: 2008).*
The English language translation of the CN 107375041A publication obtained by Google patent (Year: 2017).*
PCT Search Report and Written Opinion for PCT/US2022/070278 dated May 12, 2022, 11 Pages.
All Office Actions; U.S. Appl. No. 17/155,327, filed Jan. 22, 2021.
All Office Actions; U.S. Appl. No. 17/155,357, filed Jan. 22, 2021.
Database GNPD [Online] 1 MINTEL; Aug. 13, 2021 (Aug. 13, 2021), anonymous: "Serum", XP055915466, Database accession No. 8935135, the whole document, 5 pages.

(Continued)

*Primary Examiner* — Aradhana Sasan
*Assistant Examiner* — Mercy H Sabila
(74) *Attorney, Agent, or Firm* — Alexandra S. Anoff

(57) ABSTRACT

A skin care composition that includes a combination of palmitoyl dipeptide-7, acetyl tetrapeptide-11, other optional skin ingredients, and a dermatologically acceptable carrier. The combination of peptides synergistically improves cellular ATP level and/or upregulates the expression of peroxisome proliferator activated receptor alpha and/or methylsterol monooxygenase 1 to help provide improved skin health and appearance.

12 Claims, No Drawings

Specification includes a Sequence Listing.

(56) References Cited

U.S. PATENT DOCUMENTS

| | | |
|---|---|---|
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0197016 A1 | 8/2012 | Laughlin, II |
| 2012/0301410 A1 | 11/2012 | Ali |
| 2012/0315235 A1 | 12/2012 | Weisenfluh et al. |
| 2013/0017239 A1 | 1/2013 | Viladot et al. |
| 2013/0022557 A1 | 1/2013 | Swanson et al. |
| 2013/0064876 A1 | 3/2013 | Viladot et al. |
| 2013/0101662 A1 | 4/2013 | Carreno et al. |
| 2013/0216596 A1 | 8/2013 | Viladot et al. |
| 2013/0302261 A1 | 11/2013 | Courtois et al. |
| 2014/0370098 A1 | 12/2014 | Terrisse et al. |
| 2015/0017269 A1 | 1/2015 | Fournial et al. |
| 2015/0071974 A1 | 3/2015 | Ferrer Montiel et al. |
| 2015/0098989 A1 | 4/2015 | Ferrer Montiel et al. |
| 2015/0140046 A1 | 5/2015 | Ferrer Montiel et al. |
| 2015/0183823 A1 | 7/2015 | Garca et al. |
| 2015/0196464 A1 | 7/2015 | Jansen et al. |
| 2016/0074291 A1 | 3/2016 | Tamura et al. |
| 2016/0074301 A1 | 3/2016 | Tamura et al. |
| 2016/0074309 A1 | 3/2016 | Kessler-becker et al. |
| 2016/0120794 A1 | 5/2016 | Liu et al. |
| 2016/0317419 A1 | 11/2016 | Hakazaki et al. |
| 2017/0319462 A1 | 11/2017 | Marchant et al. |
| 2018/0264245 A1 | 9/2018 | Edwards et al. |
| 2018/0311358 A1 | 11/2018 | Marchant et al. |
| 2018/0332951 A1 | 11/2018 | Jang et al. |
| 2018/0369579 A1 | 12/2018 | Jang et al. |
| 2019/0099362 A1 | 4/2019 | Ringenbach et al. |
| 2019/0153030 A1 | 5/2019 | Peschard et al. |
| 2020/0297654 A1 | 9/2020 | Marchant et al. |
| 2021/0069088 A1 | 3/2021 | Jiang et al. |
| 2022/0233424 A1 | 7/2022 | Laughlin, II et al. |
| 2022/0241175 A1* | 8/2022 | Laughlin, II ............. A61K 8/64 |

FOREIGN PATENT DOCUMENTS

| | | | |
|---|---|---|---|
| CN | 105342927 A | | 2/2016 |
| CN | 105560078 A | | 5/2016 |
| CN | 105640845 A | | 6/2016 |
| CN | 105748319 A | | 7/2016 |
| CN | 107184459 A | | 9/2017 |
| CN | 107375041 A | * | 11/2017 |
| CN | 107375041 A | | 11/2017 |
| CN | 107802561 A | | 3/2018 |
| CN | 108309919 A | | 7/2018 |
| CN | 108670896 A | | 10/2018 |
| CN | 109330964 A | | 2/2019 |
| CN | 109394612 A | | 3/2019 |
| CN | 109453095 A | | 3/2019 |
| CN | 109464307 A | | 3/2019 |
| CN | 109846804 A | | 6/2019 |
| CN | 109953927 A | | 7/2019 |
| CN | 109984952 A | | 7/2019 |
| CN | 110074990 A | | 8/2019 |
| CN | 110123729 A | | 8/2019 |
| CN | 110179725 A | | 8/2019 |
| CN | 110269831 A | | 9/2019 |
| CN | 110302077 A | | 10/2019 |
| CN | 110302089 A | | 10/2019 |
| CN | 110384629 A | | 10/2019 |
| CN | 110420160 A | | 11/2019 |
| CN | 110522711 A | | 12/2019 |
| CN | 110585055 A | | 12/2019 |
| CN | 110585056 A | | 12/2019 |
| EP | 1790330 A2 | | 5/2007 |
| JP | 2003040724 A | | 2/2003 |
| JP | 2004238354 A | | 8/2004 |
| JP | 2004238355 A | | 8/2004 |
| JP | 2013053147 A | | 3/2013 |
| JP | 2014114289 A | | 6/2014 |
| KR | 20090062226 A | | 6/2009 |
| KR | 101769416 B1 | | 8/2017 |
| KR | 20190116693 A | | 10/2019 |
| WO | 0062743 A2 | | 10/2000 |
| WO | 2012164488 A2 | | 12/2012 |
| WO | 2018236069 A1 | | 12/2018 |

OTHER PUBLICATIONS

Database GNPD [Online] 1 MINTEL; Jun. 21, 2021 (Jun. 21, 2021), anonymous: "Eye Cream", XP055915464, Database accession No. 8749319, the whole document, 5 pages.

Database GNPD [Online] MINTEL; Oct. 23, 2020 (Oct. 23, 2020), anonymous: "Cream", XP055917310, Database accession No. 8209161 the whole document, 5 pages.

Generation of a Stable Antioxidant Response Element-Driven Reporter Gene Cell Line and Its Use to Show Redox-Dependent Activation of Nrf2 by Cancer Chemotherapeutic Agents. Cancer Res 2006; 66(22): Nov. 15, 2006; pp. 10983-10994.

He M. et al, "The role of sterol-C4-methyl oxidase in epidermal biology." Biochim Biophys Acta. Mar. 2014; 1841(3), pp. 331-335.

Lopez-Leon, S et al. "Sports genetics: the PPARA gene and athletes' high ability in endurance sports. A systematic review and meta-analysis." Biology of sport vol. 33,1 (2016): pp. 3-6.

NeoGenLab, Sur medic+ Perfection 100 All in One Facial Eye Cream, Publication date Nov. 20, 2020, date acquired from The Wayback Machine (Year: 2000), 5 Pages.

Silke Karin Schagen, "Topical Peptide Treatments with Effective Anti-Aging Results", Cosmetics, 2017—mdpi.com , retrieved from https://doi.org/10.3390/cosmetics4020016, May 22, 2017, pp. 1-14.

Soko Glam, Sur. medic+ Perfection 100 All in One Facial Eye Cream, downloaded in Jan. 2023, (Year: 2023), 5 Pages.

All Office Actions: U.S. Appl. No. 18/234,938, filed Aug. 17, 2023.

Unpublished U.S. Appl. No. 18/234,938, filed Aug. 17, 2023, Leo Timothy Laughlin et al.

* cited by examiner

```
SEQUENCE LISTING

Sequence total quantity: 3
SEQ ID NO: 1           moltype = AA   length = 4
FEATURE                Location/Qualifiers
REGION                 1..4
                       note = Description of artificial sequence: acetyl
                        tetrapeptide-11(ac-PPYL)
source                 1..4
                       mol_type = protein
                       organism = synthetic construct
SEQUENCE: 1
PPYL                                                                    4

SEQ ID NO: 2           moltype = DNA   length = 93231
FEATURE                Location/Qualifiers
source                 1..93231
                       mol_type = other DNA
                       organism = Homo sapiens
SEQUENCE: 2
gtggacgcgg cggccccgcg gcggggggcag cgggcggcgg gggcggaggc ggccgctagc     60
gccctgcccg gcgccgcctc cttcggcgtt cgccccacgg accggcaggc ggcggaccgc    120
ggcccaggtg cccgggggcg ggcgggcggg cgggcgggaa cgcgcgcggg ggtccgcggt    180
ccgggcttcc caggtcccgg gacccggagg gcggcggacg ggggaggggc aggggctggg    240
cggcgcatgc gcggggcccg gggtctcggg gtctccgggt cccggggacc cgggggcccg    300
gggtgcgcgg ctggggacct gagggcgagg agcgaggaca cacaccgagg actcttgcga    360
gggatctcgg ggcccagctc ggcctccctc ctagcgctgg gggcctgccc ggaacccgag    420
tccgcggctg tccctggggt ttggcgctgc gcggaggtcg ggtctgggga ccgcagcgac    480
tctgggtctt cgggttgtcc cctcggaggg agggcccacg ggcggggaca tcgggacttg    540
cccttttcctc ggcgcagcgg agctgggcg tcgccgactc agaaggtgct ttccgagacc    600
tccagggatc tccgaggcga ggaaacccgg gccccggaca gaccgaccct gggtgggtgc    660
gcccggcttc tgccgtcgga cggagacgcg cgtgtttgtt cctccagctg cgaccaccct    720
tgaggaacgg ttcccacttt gtgccccaac gcggcggggc gaccccggac aggctgcgct    780
gggccgggtg gcttctctgc ggaagccgcg ccacgtcgct cccggtcggg gccgctgagg    840
gtcggcgcc caggtctttc cggagtcccg ggctgcgcgg cccgcgtggt gcgggtgaag    900
ctggagggc gcggggtggt gccagtggaa gtcaggaggg tcggccctgc ccctcacgc    960
accccaaccg ggcacaactg cacgcctgtg cttttctgaa gtcttttta aaagttaaaa   1020
gagaggaagt gtgctccaag tgtcaggatt ctttccaaga aaaacccaca gttgtccaat   1080
ggcctgggct tcgtgggacc tccggggctg cacgccacg tcagcctcag ccgacccctg   1140
ccaggaaacc agggaggccc ctcctctccc agcctccttg ggataagggt gccttgggga   1200
actgggtcag ggcaaggaca cgggattttc ctgggaagga ccctgcgaca cccgtgtcgt   1260
tgcggggcag ggtcagcatg actttcctct tccaaggtga agagttgggg ggcatccaga   1320
gaacaaccgt aatcacttcc tccttcacct tcttactgcc aggctgaagc tcagggccct   1380
gtctgctctg tggactcaac agtttgtggc aagacaagct cagaactgag aagctgtcac   1440
cacaggtaaa tagaaggttt aatttactgt ttccagatgg aaatatttaa gtgttttcag   1500
tgtttacttc tgttgcacta cagaccagca atctgggggt tattactttg tgatgcaagg   1560
ttagatacgt tttcagactg aaagtaaaat acatgtgcat ggattcattt tttttttttt   1620
tttttttttt tgagacggag tctcgctctg ccgcccaggc tggagtgcag tggcctaatc   1680
tcagatcaca gcaacctctg ccactgggt tcaagcgatt ctcttgcctc agcctcccga   1740
gtagctggga ttacaggcgc ctgccaccat gcccagctaa tttttgtagt tttagtagag   1800
gcggggtttc accatcttgg ccaggctgat cttgaactcc tgacctcatg atccacctgt   1860
tcctcccaaa gtgctgggat tacagacgtg agccaccgtg cctggcctag gattcacttt   1920
gaagttctga gttattgtgt gacttttgct aggaacttca ttgcttcgtg gcaggcatgt   1980
tttgtataat ttaaaacttg atgacattaa ctttgagaaa cgtgagtgct tactagaccc   2040
ttgggatgtc cacactgact ggtaccgagt agtgtactgt ctctgagctg ttttcatttt   2100
gatttgaata ttaagcagat ggcttcttga gatagacccg tgccagaaca tgccagggat   2160
aggctgaaga aacgggccag atgatacaaa tttgtgtggt caccatccat gagagaccag   2220
ggacactggg gctgatgatg acctctgcaa ctctgaagca aaagtaaact aattggcaag   2280
ttgggtgcgg tggctcactc ctgtaatccc agcactttgg aagctggggt gggcagatcg   2340
cttgaggcca ggagttcgag accagcctgg ccaacatggt gaaaccttgt ctctacaaaa   2400
aaatagaaat attgcctggg catggtggcg gacatctgta atcccagcta ctcaagaaac   2460
tgaggcagga gaatcgcttg agcctgggag gtgaaggttt tagtgaactg agattgtgcc   2520
actgcactgc agcctgggcg ccagggcgag actccgtctc aaaaataaat aaataaaata   2580
aaattaatta actaattgac attagaaaaa aatgtttttt cttttctttttc ccacatcctt   2640
tttttttttt ttttttttt tgtgacagag ttttgctctt gtcacccagg ctggagtgca   2700
gtggcatgat cttggctcac cgcaacgtcc acctcacgga ttcgaacaat actcctgcct   2760
cagcctcccg agtagctggg attacaggca ctcaccacca cacccggcta attttttgtat   2820
ttttagtaga ggtgggtttc accatgttgg ctgggctggt ctcaaactcc tgacctcagg   2880
tgaaccgcct gccttggcct cccaaagggc tgaggttaca ggtgcgagcc accgcgccgg   2940
gcccttttcc gacatcttaa acgtaaagta ggagacgtgt cataatcatc gaatactgca   3000
gtggttttca ttagctcctg tttgtcaaac ttatgaacag agttttaaaa attgtgtatc   3060
agccgggtgc ggtggctcac acctgtaatc tttggaggc tgaggtgggc agatgacaag   3120
```

```
atcaggagtt tgagaccagc ctggccaata tggtgaaacc ctgtctctac taaaaataca   3180
aaaattagct gggcatggtg gcgggtgcct atggtcccag ctactcagga ggctgaagca   3240
ggagaatctc ttgaacccgg gaggtggagg ttgcagtgag ctgagatggc accacagcac   3300
cccagcctgg gtgacagagc aagactccgt ttccaaaaaa aaaaaattgt atatgagaga   3360
gacagaacta gacagagaag aaggagaaaa tgtgtcttct ttatacacta ttttgtaact   3420
tgctttatcg agtaggttat gaaaaatctt cctatgtgaa aaacatttct gcatcatttg   3480
aaatgtctat ataatatccc attgtgttta gatacaataa tatttagcca atctctttat   3540
gtgtatatat ttaatacagt cattctataa atattgactg agtagctgct gtgggctact   3600
gtccgcagtg ctgaacaaga caagcatgaa tccatgaaac tgattttcat accagaaatat  3660
aaaaaagaaa cttaaagata atcctcatca tggtaaaaga tgaagaacct attttttgccg  3720
ggacatctta ctctttagta attggtggcc agtgttcttt ttcttgcatg ctgtttggga   3780
gagtctgttt tttaaataaa tatttaagta gcctgggcgc agtggctcac gcctatggtt   3840
tcagcacttt gtgaggccga aggggatgga ttgcttgagc ccaggcttc aagaccagcc    3900
tgggcaacct ggcgaaaccc tgcatctact aaaaatacaa aaattagcca ggtatagtgg   3960
cgtgtgcctg tggccccatc tacttgggag gctgaggtgg gaggatccct tgagcctgag   4020
aagtggaggt tgcagtgact gagatggcac cactacactc cagcctgggt gacagagtga   4080
gacctggtct caaaaaataa ataaaatattt atgtaatcat ctttaagcag tgttttttaat 4140
tttatttatt tattattta tttttgagac agggtctcac tgtgtcacct aggctagagc   4200
acagctgcat gatcacggcc tattgcagcc tcgacctccc tgggctcagg tgatcctccc   4260
acctcagcct cccaagcagc taggaccaca ggcacacgcc accaggcctg actcattttt   4320
gtattttttg cagagacggg gtcttgctat gttgttcaga cctgtctcaa actcctgggc   4380
tcaagccatc ctcctgcctc ggcctcccat agtgctggga ctaagccatg aaccactgca   4440
cccggcataa gtggtctttc tttaaaaaaa aaaaaaaaa aaaaaaaaa aaaaaaaaa     4500
aaccacatta ttaaaatat gtatttgctt attataaata tatttgaaac atgccaattt    4560
ttcttctctt ttttgctct attggtttct gtgtgtggat ggatatattt ttaatggcaa   4620
ataggatgag tgtcttttact tccaagtagt cagtgttttt ctttaatgtt tgtactaatt 4680
ttgtcacatt gcagttagag gttgtggcct gtctaattc tgcttttttg gaacttgaga   4740
gtctctgttt ttatttgttt ttggtagcct ggcatagagt ccattttttct tttcttttct  4800
tttttgaga cggagtttag ctcttgttgc ccagactggc gtgcagtggc gcaatctcag   4860
ctcactgcaa cctccgcctc ctgggttcaa gcgattctcc tgcctcagtc tcccccagtag 4920
ctgggattac aggtgcccac caccacacct ggctatttt tgtattttta gtagagacgg   4980
ggttttgcca tgttggccag gctggtctcg aactcctgat ctcaggtgat ccacccgcct   5040
cggcctccca aagtgctggg attacaggtg tgagccactg cgcccagctg tagatacttt   5100
ttaaaaaggt atagtttctg attatggggt agaaatgtgc tatgtctgtc atttcagcct   5160
tatgaattgc ccagaataag ctagatcacc tttaaggcca tgtggttagg gaaacttggg   5220
cacagaattt acattttcaa cttggtgata agatgggttt aaggtaagaa tcaaatagga   5280
gaaagcctta gctgttccag cggcccatgt ttaaagaat gtgcttcttt ttccaagtat   5340
ttctgccgct tgcatgcact gagcttcttt ggaaaggagc accatgcagg catatttcc   5400
agacaggacc ggatttgctc gttactcaga ggtgtgtgca ttctttgctt ttaggatatt   5460
taattagcat ctttaatag tgatattacg gtgtcttaaa agtttatgca tttgaaaaga   5520
aaagaactta ctccttgcca ggtctcaacc tatcatggtt atctttgcag ctgagctgcg   5580
ttggttttga ggctcacata tggtaaaagt ggttggaaat ctgaaatatat tgctgtgtat  5640
ctgcaaagca cttgatata gtggaaaagt tattaggtca ttaatcatga gatttggatt   5700
ctagcccctt agctgctgcc tgccaggcct ggagaccttt gttctcttct ttaaactgct   5760
gctttctcat cagaaaatga agttcctctc cataccacct ctctgaaggg ctgtgaagct   5820
cgaagtggca gcttaaaaaa ctgcccatct caggaggtgt cttaagaagg aggacatacc   5880
gctggctcct gccttttctca cttagccagg tctgatacct gtgttgtttt cactgtggcc   5940
attttaggat ttttcaaagg ctttcagaaa gcaacatgct accgtacccc ttatacacca   6000
aaactggttt tcattttgga atataaaagt gagatttctc caccagtaca ataaagttgt   6060
tacaagtggt tcctatgtgt ttgttttgt ttttgagaca gagtctcact ctgtcaccca   6120
ggctgcagtg cagtggcaca atcttggctc actgcaacct ccgcctcccg ggttcaagca   6180
attctcccac ctcagcctcc taagtagctg gactacagg cacccgccac cacgcccagc   6240
taattttgt attttagta gagatggagt ttcaccatgt tggccaggct ggttttgaac    6300
ttctgacctc aggtgatcca cctgcttcag cctcccaaag tcttaggatt acaggcgtga   6360
gccaccacac ccggcctcct gtgtgttttg aagtgattg tgacctcagg ttttggcagg   6420
gctataccctt gtgtttgctc ttactccaac tccatggcat acctggacca ggcctcttca  6480
tcttgaagag ggatctgctg aaatgcaggc ccagtgaatc tccccatgcc tggacacagt   6540
tccgtcaagc caggacccgg tgctgcctgc acccctgttt ctgttagtct gactgtcctc   6600
gctgagtcta actccttgag ggcagagagg atgtcttatt tatttctgcc ccgctagccg   6660
tgtaaactga gtaggtactt gtaaatgttc attgaataag tacctgatta atagaattta   6720
attcaagaag aatgtattga tgggcctgtg tggtcaccac agtactgaga tgtaggtggg   6780
agctggctga agggggaggc acctaaacag gagtgcagac agcggcacct acggatgatg   6840
gcccgctcca tcccaccgca gcgaaattgt cccagacctc tgcagcttcc cccacaccta   6900
gactgagaga gagctcttct tccttctgta gggagcaggt gtttcctcca gatgtccaat   6960
atgtacctcc cattacagcg gtgttaggaa ggtgagggct gccgctgaaa gggtccccctt 7020
cataatcatc actagatttg gggtatatta tggattaaat agaattttta taagatgacc   7080
tgaggatcta tttaaataaa atcctctttc tttctgcaag atcatggatt taaattcaac   7140
acaactgact tcatagggaa ggggtatggt gaaagggaag tgagtgggc agcactgata   7200
tttaacaagg tgagggtcct tctcctgctc tgactgtcac attaaaatat tcccaggaga   7260
aattggagaa aactcagatg aaatatcgtc tgtgttccag gaggcaggac tcatcggaat   7320
gcttttattt tgctccattt taagagattt gcagataaag aggagtgaag atttctattc   7380
agatttactt gctttatatt ttaacttata gaccacaagc caactttcga aagagcatca   7440
ttttgaatag taagagttag gaaggcaaat acagaaggac taatggcttc caagattatg   7500
agcttcatag gaatggttg agatgaggct atagtaaagt agattattga agttccccca   7560
ccccctttca tttttcattt ttcattttta agagtgagcg aggccaggcg tggaggctca   7620
cacctgtaat cccagcactt tgggaggccg aggtgggcag atcacaaggt caggagtttg   7680
agaccagcct ggccatcatg gtgaaaccct gtctctacta aatgtacaaa aattagccag   7740
gcttggtatc aggtgcctgt aatcccagct actcaggagg ctgaggcagg aaaattgctt   7800
gaacccagga gtcggaggtt gcagtgagct gagatcgcac cactgcacat ctcagaaaaa   7860
```

```
aaaagagtga ggcccccaagt tttttttgcat ttgtttgtaa ctgaatacgt ctgaagttat   7920
gtgataacca cgccaaggtg acaaattgcc aagtttcagt aaaagagacc cagttattta   7980
gaggttgaca cgtggatatg tcccttcta  agaagttcgt ggtcagcttt acatgagtat   8040
ttaaatgcgt gtttataatt cagcaatatg gcttgtaaaa tacagattgc caatcaagtg   8100
acatgcaaat cttgatgatc tgaaacaagt ttccttctgt tatctatgga agaaatggta   8160
atagggatat ttaagtggga tgaattttt  gaagcattt  caggcagttt tccacatgga   8220
acaaaataac attgagtggg ctgctaacat gaggaacata ttgccctctg cctaggatta   8280
tgagtaaatt tgataaattc tagactgcag tctcatttta gctcatttta tgaggcagct   8340
tgacaactgg gatagtgtct ctttttttg  tcggggtgt  tgaggctgga gtctcgctct   8400
gctgcccagg ctggagtgca ctggcgtgat ctcggctcac tgcaacctct gcctccgggg   8460
ttccagtggt tctcctacct cagcctcctg agaagctggg attgtaggca tgtgccacca   8520
cgcccggcta atttttgtat ttttagtgg  agacgggctt tcaccatgtt ggccaggctg   8580
ggtctcaaac tcctgacctg aagtgatctg cccgcctcag ccaccctaag tactgggatt   8640
acaggcatga gccaccacac ctggcttctg ttctatctgt gcattgggga tgaaattaac   8700
acaaatgatg tttaaagaaa aaaatgctca gagaagttag aaatgtgctt taaattggaa   8760
tcatctctta gtatgtaaaa gttttttgta atagaaacaa gcagggcagt atttgacctg   8820
ttgacagtgt ccttggactt tacaaattgt gaagcagcgt attttgcttg agttgtacga   8880
ttgtcgtttt ttcccccca  cttttgacaac tgttacagaa cctgtcacca gatacaggca   8940
agggaggttg ggcttcccat ctctgcacgg cttccctgtg attcacaagc aagcaatcag   9000
aagtgcacaa aagtttagaa cgcgattttc attctcttct ttccttagaa aaactcgctt   9060
tgttagcctt ttcagaaaag gaaggcactc aattgttgta atactcaaat cataaaaga   9120
agcctagtct agtctattca gcaaggtgtt ctgaaagagg gaattttta  agttcaatta   9180
tgcgaagatc ttgaaggtgg gactcaaagg agagggctat cctgggaaga aggctttgga   9240
aaatgagagg catgaagggg agagggtatt taaatgtgtt tgaagccaag gatccttgag   9300
agaaaaagct ggcactaaca gcgttcaaag aacttgcgtg acaagtgatg actaatgaca   9360
ctgagggtgg gttgtgggtg cctagtgaat tcctccgaga ccaagagaga ggtttccaga   9420
cccagggaag aagtgtgta  cacccagaag tagtgtaggg acagagattc cgatcacaag   9480
ctgtgactga aagacgccga ccaccactgc agcagcctga aaaccacagt cttgaaccgc   9540
cagcgaaggg ctgggaagtg cggatccagg gctggtgcac tgaacccaga ggagcaggct   9600
cccattccca gctaagggtg cagcttggcg gggatctttc cagcagaaga ctgtaagtgg   9660
aagctttcaa ttcagagcag tagcaatgcc ttcaaagtcc caggcttcac gtgggaacag   9720
agaatgtgaa gagtatttag caggatgcca atataagaaa tctatattgg tgttcgtttg   9780
tttgttttg  agatggagtc tcgctctgtc acccaggccg gagtgcagtg gtgcgatctc   9840
agctcactgc aatctctgcc tcctgggttc aagcgattct cctgcctcag cctcctacat   9900
agctggtact acaggcacgc gccaccatgc ctggctaaat tgttgtattt ttagtagaga   9960
tggggtttca ccacgttggc caggctggtc tcaaactccc ggcctcatga tccgccctct  10020
gcagcctccc aaagtgctgg gattacaggc gtgagccacc gcacctggcc caatattgtt  10080
tgtttattta tttcttgaca ggatctcact ctgtcaccag gctggagtgc agtggtgtga  10140
tctcagctca ctgcaacctc cacctctctg gctcaagcaa tcctccctcc tcagcctcct  10200
gagcagctgg gactcaggt  gcacaccacc acacccaact agattttgtg ttttttgtag  10260
agatgggtt  tagccatgtt cagctagtct caaactcctg ggctcaagtg atctgtccgc  10320
cttggcctcc caaagtgttg ggattacagg tgtgattcat gatgtccagc ccagtatttt  10380
tctttcactc tggaaaccaa aaatattgg  ctttttttt  tgttgcattc cctttactta  10440
gatgaatcta gcaaggttgg ctgttagtgt ctaggtcaga agtctaagtg aaagtgaata  10500
tttaaccaca ctcaagcaca gctgatgatc tttaatacta atagaggtat aagacttaaa  10560
agaaacaaga acccagaggg aaaatatggc catggactca gagaaaacca cggcagcttc  10620
catggactca taaaaagagc tcaaaaccta ggaagtggat ggagactctt tttggaatga  10680
atgaattcaa atgtgggctt tcttagtaga ttaaatcatt ttctagaagg aatttccagaa  10740
ggatgtgtgc ccaattatgg tatcaggtct gttgtagact cttcaaggag gaagcctctg  10800
aaagacaaga aggaacaatt aaaaattaga attcaggtga gtggatcacg aggtcaagag  10860
atcgagacca gcctggccaa catggtgaaa ccccgtctct actaaaaata caaaatttag  10920
ctgggcatgg tatggctgta gtcccagcta ctcgggaggc tgaggcagga gaatcacttg  10980
aacccgggag gcggaggctg cagtgaacca agattgtgcc actgcactcc agcctggcaa  11040
cagcgagact ccatctcaaa aataataagt aaataaataa ataaataaaa attagaactc  11100
agaaaaggaa ttaatttctt ctgagagaga aaaagatgag attctagcct aaggtgtaac  11160
acatccatcc accaggtatc attttttatac acgtgaagtt aaatcaccaa aggaccaggt  11220
gagcagatgt ggactttccg actgtgtgtg tgcgactttcc tcagagccct cagtggcgtt  11280
ccctttttccg cgctagcgtt tggtccctgc gcttttctgg atgcccccac cccctctggc  11340
tccacgagcc ccccgtacg  tcaccatcac cttttgtgagc ttgaaacctg tcacccaccc  11400
gccttccaga tgtcacctgg gccctcccgg aggcccctcgc cctcagtgtg tctgattctg  11460
agctgtcctg cgtttttcccc tcccctcacc ctggcgaccc ttttcggtct cagttgccag  11520
cctcctgcta gggctgggtg ggggacatca aaggcaggac aaggtgtagg gtcctcaccc  11580
accacttagc agctctcaga tgcagacaga ttttcagct  ggcctgtggc tcagttccc  11640
tcagctacaa gagggtgca  tgctaggtt  tctctggatt gctgcacctg gcaggtagtg  11700
tgagcttggt aggtgcttcc ttgcttatca ttgcctctcc catcttaatg ttgtcccatc  11760
catccaatgt ttatgggatg agaggttgat aggagggcat ggccctgaca ttccagggac  11820
tgaccgcacac gctgtctaca caaacccctt ctggttcttc tcgtgcactg ggcgtgccgg  11880
agacacactc ccttaccctc ataccccgcc gcaccccctgt gacctctacc tttgagacct  11940
cagcttaaac tcactcttag ggaaggctcc ctgaaccacc tgctgggggtt gtatgctgat  12000
gcaggtactt gtaacacctg gtgctttttcc tttcgtgcac tcaggcagtg tttattcaag  12060
tgatggcttg gtgacagtgg ctctccctga gaccccgtga ggcagagtc  cttggctcat  12120
cactcatggt tgaacccgga gcctcttgct ggtaggtgct tcaggactgg ctctgggagc  12180
ctgtggcctcc tgccgggtac ccaccggttg agatacctca agttttaaaat gccacctcct  12240
tcctgaagcc ttcctctg  tccccccaaa ctagaggcag gagttttgtc cttcagataa  12300
cctatggcat ttgagtcact ctgatttgat gaattctgcc ttcacttgag cagctattag  12360
gggcatatgt cagtcattca ttcctcagtt catgtattta ttcagcaaat atttactgag  12420
cacgtactgc gtgccaggca ctgtcctgct gtggaaaaca gcaggcatga ttccctgcca  12480
ctaccaacca ctgcatcgca taactggcag actcccagct tcaaggagag gcacggaggg  12540
aaactgagag cagcctgcag aggggaaaga gcggggacag agggtcacgg aggtcgcagg  12600
```

```
ggcgtgtgtg cagcacctgc cagtgaacgg aatgtgcggc tccagatgtc gttgtcttta  12660
aacttcggaa tttcctttca ctaaagaacc aagtccaggg ggaggaaaga gtgaatacaa  12720
attatccaag aaactcaaga gctcatttta gttctcctga ttatgatctt aaaggcatta  12780
agcgctcaag ttaaactcct tgtgacccac ataggttagc agaatttaaa tcctaggtga  12840
ttattaactc taatcataca tctaatgacc tatattgaag atacactgcc tgcttagttg  12900
tggcttcagc ctttgctccg tcactgatag ttctagcctg aaaagcaaat gagccctcat  12960
gctcacgatt tcaccacagt cacataagcg ggaagagcag gctcctggct gtggcgagct  13020
tgactccatt tggtttgata gaaatgagag gtagatgatt ccctagacaa atgcaggcct  13080
ttctcgaagc ccctttccca ggacgacgtg acatgagtgg tctgtgcctt ccagggcagc  13140
cacgtcatgc tttgcccagc cagggcggtg gggagggaga cagccacatc ctgcccgggg  13200
ctcctgggcc ccgctgcatc aagtgaaagc agggctggct ccctgatgtc cttggagaag  13260
tcgcccacac tgctttcccc catgggagtg acaaggatgt gtcccgccag ccttccacga  13320
cggaccccc  actctctatt aattcccaag aaaccaggcc atggaggtgg gtttgagggt  13380
ttgtattggt gtttttaaa gtcaggttga ccgagtgcgg tggctcacgc ttgtaatccc  13440
agcactttgg gaggctgagg cgggcggatc acatgaggtc aggagttcaa gaccagcctg  13500
gccaacatgg tgaaaccttg tctctactaa aactacaaaa aaaattacct gggcgtggtg  13560
gtgggcgcct gtaatcccag ctactcagga ggctgaggca ggagaaaccc ttgaactagg  13620
gaggctgcag tgagccgaga tcgcgccact ccagcctggc gacaagagt gagattctgc  13680
ctcaaaataa ataaagtcgg gtttattaag atataaattta catacagtaa ttttttttt  13740
ttttgagaca gagtttcact cttgttgccc aggctggagt gcaatggcac gatctcagct  13800
cactgcaacc tccgcttcca gggttcaagc cattctactg cctcagcctc ctgagtagct  13860
gagattacag gtgtccacca ccatgccttg ctaattttttg tatttttagt agagacaggt  13920
tttcgctatg ttggccaagc tggtcttgaa ctcctgacct caggtgatcc gccagcctcg  13980
gcctcccaaa gtgctgggat tacaggcatg agccactgca cccggccagt acatgctttc  14040
ttgatttgtc tgtttcccac ctgtctcccc tccctagaat ggcagctcca tgacgacaga  14100
ggtgtttctc tgttttctcc atggctgcac cctcagctgc tagaaggtgg cccagcatag  14160
gaggtatttta atgaagcctt cctctccact taaatctaca cccttgtgct tattaaaagg  14220
tgacagtttt ctgtttgaaa attttattag tgttttaatg agaaagttat tatttgggta  14280
atgcctgaat atgaggaaaa cattaagggt agaaatgtaa ttgttttcct atttcattca  14340
gtctatggat tttattgaag attacagaat tacttctttg tagctatgga agtaaaaaaa  14400
taataagacg agtagctatt tcaaaacgta gggctgataa atttgggatg gtttgagaac  14460
gttaagttgg ggaactccat ttcttttttt acatttttat ttattttcat ttgtttattt  14520
atttatttga gacagagttt cgctctgttg cccaggctag agtgcaatgc catgatctcg  14580
gctcactgca acctctgcct ccggggtata agtgattctc ccatatcgc tccccgagga  14640
gctgggacta caggcgcctg ccaccacacc tggctaattt ttgtattttt agtagagatg  14700
ggatttggcc atgtcagcca ggctggcctc aaactcctga ccgcaggtga tccgcctgcc  14760
cttggcctcc caaagtgctg ggattacagg tgtgagccac cgcgcccagc cagggaactg  14820
catttctgac agtggctcag tagttggaa gttaactggc aaaggtggac agaatcttta  14880
aacatatgtg aggaattgg agagtttaca agatagtgaa gaactgccag gccatggtct  14940
ggagaagatg gaaacttgat gttttgggcc attgtgtccc tggggtgttg gccaatttat  15000
gaaagaagca gttaagagcc tgagtggcac ttttgagggg ctagaaggga agaccctggt  15060
aaacatccca aactttggat tgggacccaa aaaagctcca tccaggagt acaggtgacc  15120
tggaaacgga tcagcgtaat cgaggactga agtccagttc tagctacgcc cagtccttga  15180
gactggatta aggtgatctc agattgcaag gacctcaaat gcctggcaga agcaagtgaa  15240
tatccttctg gaggaacaga gcctcatcct aggcctctaa ttattttttaa ggacaatttt  15300
tcaaatgcag gctttcctcc ctttgcacag ttcccttatg cataaatttc agtcagtggc  15360
cagctgcagt ggctcatgca tgtaatccca gcgctttggg aggccaaggc gggtgaattg  15420
cttgagtctg ggagtggag accggcctgg gcaacataga accccatctc tattttttaaa  15480
aataaaatat taattatcac tgcttagtta aattatagtg gtctcccaac aatacagatc  15540
agatcccagc tccatggta tatacactgt gagtgctgta taaagtacaa gctctgccgc  15600
cagttctcca gcctacaaat cacagtatag ataacagatg tgcatgatga tcactggcca  15660
attgcgtcac ttctctcaaa gtcagtctgt gattggtccc tgagcatctg tcggtcagtt  15720
tcatgcacag actgcaaagc atatggtttt gtctactctt tgtctctcag tgataaaccc  15780
acatggcatt ttgtaaaagt ggatacatca ggccaggtgt ggtggctcat gcctgtaatc  15840
ccagcacttt gggaggctga ggcaggtgga tcatttggga tcaggagttt gagaccagcc  15900
tggccaacat ggtgaaaccc catctctact aaaaatacaa aaattagctg gatgtggtgg  15960
caggcgcctg taatcccagt tactgggag gctgaggcag gagaattgct tgaacccagg  16020
aggcagagct tgcagtgagc cgagatcatg ccactgcact ctagcctggg tgacagagca  16080
agactaccat ctcaaaaaa aaaaaacaaa aaacagtaat caagcatgaa aattatgaaa  16140
tgctcagaga taaaatgcgc gaggcctgta cactgtaatc tacaaaacac tgctgagaga  16200
aatttttaaaa gacctaaata aatggcaagt tataacatgc tcttgaatca gaagactcag  16260
tatcttagga tggcgacttt tcccaaaatg atctacagat tcaaagcaat cggaatcaga  16320
cctcagcatg cctacttgta gaatttgata acctgattct aaagtttata tggaaatgtt  16380
aggaacccag agttgctaaa ataactttga aaaagaacaa cagtatggg ggacttagac  16440
tacatgattt caagaattat tataaagcta cagtaatcaa gacagtatgg tattgatatg  16500
aaaatagacc attagatgaa tggaacagaa tagcaagtcc agaaatagat ccacacatat  16560
atggtcaatt gattttcagc aaagtgccaa gtcatttaag tggggaaaag ataatctttt  16620
caacaaatga taccggaaca actggatagc catatgcaaa agaacctcaa ccttcagctc  16680
acagcactac aaactcataa tttattatcat tattattac tattatgtaa taatagtata  16740
tatcatgtta catattatat tatgtaatat atattatatg atactgttat gtcatataat  16800
tattattgaa atgggtcata gatctaattg taagagttaa aaccatccag gtacagtggc  16860
tcatgcctgt catcttgcac tttgagaggc caaggcgggt ggatcacttg ccccaggag  16920
ttacaagacc atcctgggca acatagcgaa acaccgtctc tacaaaaaaa tgaaaaaatt  16980
acatagctga gatgacactg ctagtgccag ccagctgcac gatagtctga ggtgggagga  17040
tcacctgagc ccagagaggt caaggttgca gtgagccatg attgcaccac tgcactccag  17100
actgggtgac agagaccg tgtgttaaaa aagagttaa aactataaaa ccttcagaag  17160
aaaacatatg agaaaattct agtgatttgg ggtttgcaa agattccttg aacatgatt  17220
aaaaagcatt aactaggcca ggtatgctgg cttacacctg tcattccaat gctttggggg  17280
accgaggtga gaggatagct tgaggccagg agtccgagag cagcctgggc aacataacaa  17340
```

```
gagtgggtct ttaccaaaaa aaaaaaataa aaagcctgtg ccaggcacag tggcacatgt  17400
ctgtagtcct agctactcac gaagctgagg caggaggatc acttgagccc aggagttgaa  17460
gcttgcagtg aattatgacc atgccactgc actccagcct gggccacaga gtaagactaa  17520
gactcagtct cttaaagaag aaagcgaccg ggcgcagtgg ctcacgcctg taatcccagc  17580
actttgggag gctgaagcag gtggatcaca agggcaggag atgaagacca tcctggctaa  17640
cacggtgaaa ccccatctct actaaaaata caaaaaatta gccggacgtg gtggtaggcg  17700
cctgtagtcc tagctactcg ggaggctgag gcaggagaat ggcgtgaacc tgggaggcgg  17760
agcttgcagt gagccaagat cgtaccactg cactccagcc tggacaacag agcgagactc  17820
catctcaaaa aaaaaaaaaa aaaaaaaaaa aaagaagaaa gcataaacta taaaagaaaa  17880
aattaataaa ttagtcatcc tcaaaattag aaacttttac tcatcagaaa acacttaata  17940
aaatgaaaag tcaagccata gacttagaga aaatatttac aaaacatata tctgacaaag  18000
gacttggata tggattatat aaagaactat tgtaattcaa taagatgtca aacaacccaa  18060
ttaaaaatgg gtgaaagatg aactaactct tcaacaatgg gcatgtcatt tgaatggatg  18120
gtaagcaagc acatgaaaag atgttcatgt gcctttccct cattagtcac tagggaaatg  18180
caagttcata gacatctctc ttcgtagaaa gatatcacta cacacccaca agagtggctg  18240
taattaagca gtctgaccaa gtatgcgtaa gaatgtggaa taagaactct catacactgc  18300
tgatgggaat gtaaaatgat agccacttg gaaaacattt tggcaaataa taccacttac  18360
attattatcg aaaatattgt atacctgaaa gaactcaaga tgaaaaagct atatactgtc  18420
tgcttccaag gctacacatt atgggaaagg caaaactatg aagacagtaa aaagatgcgc  18480
cagtggttgc caggggctca tgggaggga aagaggaatg aataggtgga acacagggca  18540
tgtttagggc agtgaaacta ttctgtatgg taccgtaacg atgaatacat gttattaggc  18600
atttgtcaat acccataaaa tgtacaacac aaagagtgaa aatgaaaact gtgggcttca  18660
gttagcaata atatgtcaac attggctcat cagtggcaac aaatgtacct caccaatgca  18720
agatgtttgt tgttgtttg tttgttttgt gacggagggg gtgcagtggc gcaatctcgg  18780
ctcactgcaa gctccgcctc ccgggttcac gccaatctcc tgcttcagcc tccggagtag  18840
ctgggactac aggcgcccgc caccacgccc ggctaatttt ttgtattttt agtagagacg  18900
gggtttcacc atgctagcca ggatggtctt gatctcctgc tgtcgtgatc tgcccgcctc  18960
ggcctcccaa agtgctggga ttacaggcat gagccatcac gcccggccac caatgcaaga  19020
tgttaataac agggaaactg tggtgggagt gaggtggtat atgagacctc tctgtacttt  19080
ccactcaatt tttctgtaag cccaaaactt ctctaaataa gaaagttttat taattaaaag  19140
ttactttttat agtgtatcta tatctaggaa taaatctgaa aaagatatat aagatctcta  19200
ctcagaaaac tgattatgtt attaagagag cttaaatata gcccaaataa atagatggat  19260
atactatgtt catggaaggg acagctcagt attaggaagg tgtcagtcat cttaagaaaa  19320
gcctcatgtg tcacacaagg gatactgaca tctgacacca agcacatgta ggcatcctga  19380
ctacgtttac ttgaatgatg tggactttac agagctgact atagacagtt caaatggcct  19440
gaaaactgtt caatgcactc cctcccaggc tgtcatggga tgcacttcag gaactttact  19500
ttttaacaag aaaattcagt tttcctctta aacagctggc ttctgttcca ttagcattct  19560
tgtcactttta agttgcattc atctttgttt tttttttta gaaaaacatt tgttctgcaa  19620
ccagtcttgt cctttaaata cttgtactgt atacaggctc tttttcatag gtccattact  19680
taaaatgatg taagtgtgtt tttggtggca ggggggtggg agttgtttgt tttgttttgt  19740
tgagacacgg tcttactctg tcacccaggc tggagtgcag tggtgtgatc ttggctcact  19800
cctggcctca agtgatccac ccacctcagc ctcctaagta gctgggacca caggtgtgta  19860
ccaccacacc cagctaattt tttttttttt tttttttttt tttgtaggg acggggtttt  19920
gtcatatcac ccaggctggt ctcaaactcc tggactcaag ggatcagcct gtctcagcct  19980
cccaaagtgc tgggattaca ggtgtgagcc actgcaccgg tcctgatttg agttttgta  20040
agacaggaa caatgttcag aatttagcac caatgtcaga ctcattctgt aaattttat  20100
tgaacgtctg cctggtgtag gagaggaaga tgacagacaa gaattcttcc tccaagagtt  20160
acaggtcagt tgagcagaaa aggcatacat caataccac aatgagagtt gtcgtgattc  20220
agaggaggga caaagtcctt cccctggagg gatcctgagc actttggaga ggaaaggcat  20280
ctgtactgcc ccccaaatgt gtagaatggg atgcattcct ggcagaaaga agtaggataa  20340
agtacagagg ccagggctgg gtgcagtggt tcacgcctgt aatcccagca ctttgggagg  20400
ccgagacagc agatcacctg aggtcaggag ttcgagacca gcctggtcaa catggcaaaa  20460
ccctctctct actaaaaata caaaaattag ccaggcacaa tggcaggtac ctgtaatccc  20520
agctacttgg gaggctgagg caggagaatt gcttgagccc aggaggcaga gatcgcagtg  20580
agccaagact gcgccactgc actccagcct gggcaacaga gcaagactct gtctcataaa  20640
aaaagaaaaa aaaaagtac agagtccagg aagcctgggg tggggctggc agatgccgag  20700
tcatctattt tggccagagt tcaaggcttg ctagggaca tgaagagaag attcgtgcat  20760
tctagttcaa actccaccag atatttgagc tccttctctg taccaggcat tgttctaaga  20820
tacgtaagtg aacaaaaccc atgacacct cgtctatgga agctgatcct ctggccaggga  20880
cagacaggtc atgagtggag tgatggagca gctggctgg tgacttagcc gccttcaggt  20940
acagtaggag gagcaagccc aggacaggtg agtgggtcaa gggtgccaga aggggtgagg  21000
gcaccaggaa gctggtccag tttggcttcc ctgaggtggt gaccaggacc tagcatctga  21060
ggaagggctg aagcaggtg agagcaggtg gagcagacat caggatggga gcatcctgac  21120
aggagggca cagggtggg ctcatgagg gaacagccag gaagtgtgac tcgagcagtg  21180
tcctggagag gaggaggagg agaaagaggt caggaggtcc caggggagag gcaggaccag  21240
tctcgtggag gtcggggccg ttgtgaggac tctggtttgt gttgtgtgtg aaaggccatg  21300
ggatggggac cagcgagggc ttcttagggg actggatatg ctctgatcta gctgctaaaa  21360
agcccccttg ggcagcttgc agggcccggg cagaagctat aggtggttct gaggtttgca  21420
gagggcctg aaggggtggg gcccggccaa gcaaggtggc taagtgggaa aggctccacc  21480
gcgttgggtg taggaagacc ttgacccttag ctccagccca gccactgagc agccgtgtcg  21540
ccttgggtga tacctgtccc tggtcggttt ccctacctgt gaatctgggt acttggaagc  21600
catgctcgaa aagagcccat ccccaggagg tgatcagggt tctccttcag gtgaggaacc  21660
tggcagccgt gtgtgagaac cttagaaaag ggagagggaa gaggctgtgg caggaagtga  21720
gggggagtt agtgataccc tgggcaggat gccatggagt ggtgaaa ccacaggatg  21780
aatgcaagta attaaaaaaa aaaaaaaaaa aaaacagca ttgggccggg cagtggctca  21840
cgcctgtaat cccagcattt tggaggccga ggtaggtgg atcacctgaa gtcaggagtt  21900
ggagaccagc ctagccaaca tggtgaaact gaaaatgcaa aaattagcca ggcatggtgg  21960
cgtgtgcta tagttccagc tactcaggag gctgagacag gagaatcact tgaacctggg  22020
aggtggatgt tgctgtgagc tgagatcgtg ccactgcatt gcagcctcgg tgagagagca  22080
```

```
aggcccatc tcaaaaaaga aaaaaacaga ctttccgacc aaacgatcga caaaccagac  22140
tgtccaaaca gccataagcc gtaactttgt gcggaggtaa aagaccgagg tcacatcggg  22200
acctgttgga ttcaaggcat gttgacagct gtttccaggc ttcagataga gcctccagct  22260
ggcagggtgg ccacagggct tgttgagtag gaagcctcgt tgctttgaca ggttacttgg  22320
ccccatgagg gacaatccca tagtcagtta cccagaaacg tgactgtctc cttgaaatcc  22380
tcagcatggg gtcttatgaa taaacccttt actagatttcc tgttctgtct tattttttatg  22440
cagagcttta ctttatagca gaaaattcca ttttttaccct taaatggctt gcttctgctc  22500
ccttagtgtt cttgtcactt taagttgcat tcatctttgt ccctttagaa aaggatttgt  22560
cctgcaacca gctcttgcag aaggtacttg gtttattgtt aaccgatgtt tgctaaatgt  22620
ttgaattatg ttgagttgct taaagtcatg ctatcgggta gatgttgtgg ctgttctttt  22680
cactctctta tttggggatt tacaaaacag ttatgttttt agttttcttt tatttgttgt  22740
gttgaatagg aatgtagctc tgggaacctc tagttccaaa taagaaagcc ttggacacat  22800
ttccagttgg caagctggca aaatgaaggg cgtacaagtg gttagagagg ctgggagcct  22860
atttaagcac ccagcttcag gatgggacat gggatatacc tcgagttaga ggttcttatt  22920
aactgtggat tcttctatgc agatatctgt cacaatataa gttactataa gtcagtacta  22980
aggcagctgc tacattctgt ttgccaaggg gaagaagaaa gcttggaaat ggtattcctt  23040
aaaaatgtca gtatcataaa agacaaagaa aagctgcgga aatgtttcag attaaaaagag  23100
agaagacaat aaaatgtaat acctgactct gaacagcatc cagtactgaa ggaggaaaaa  23160
tgctatcaag gacattattg ggtcaattaa caaaatttga atacgaatca tagattgaac  23220
tgtatctgtt aaattaacag aagcgaagtg ttctgtggtg tgtaggagca cactgccatt  23280
cttagcaaac gtgtagttta gtatttagga gaaagggcca tgaggcatgc aactcaccct  23340
caaatacaca cacacataca catatataca tacataccta taaagaaaga aattatgggc  23400
taggtcagt ggctcatgcc tgtaatccca gcactttggg aggccgaggt gggtggattg  23460
tgaggtcagg agatcgagac cctctctact aaaatacaaa gaattagctg ggcgtggtgg  23520
tgcacgtctg tagtcccagc tactcggaag gctgaggcag gagaattgct tgaacccagg  23580
aggcagaggt tacagtgagc cgagattgca ccactgcact ggcctggc aacagagcaa  23640
gactctgtct tgaaagaagg aagaaagaga gagagagaga gagagagaga gaggagaaa  23700
gaaagagaga gagaaagaaa gaaagaagga aggaaggaag gaaggaagga aattatgata  23760
aagcagatgg ttaagttggt aactaccagt gaatatgggt aaagttagga tgttcttttac  23820
tctgtttttgg gggtgcaact tttctataag tgaaagtact tccaaataaa aagttaaaag  23880
gcaagcaaat aaataaaaga gacagttttct atgttatata tcctagctat gtttaccatg  23940
tctggattct gaaagctgca gagcagaaaa cctgaagaac agatcacctg ttcttaaaat  24000
accactgttg gccagacata gtaactcact cctgtaatcc cagcactttg ggaagccgag  24060
gtgggaggat caccctgagct caggagtttg agaaccgcct gggaaacata gtgagaccct  24120
gtctctacaa aaatttaaaa aattatccag gcatcatggt tcgtgcctgt agtcctagct  24180
actcaggagg ctgaggtagg aggattgctt gagcctggga gttcgaggct gcagtgaacc  24240
atgatcacac taaagcactc tagcctgggc aacagagcaa gaccctgtat caaaaaaaca  24300
atcaaacaaa aaatcactcc taattttcct ccctttttagt acttttaaaa attaacttaa  24360
aacatttttt ggataattgt agtttttttt actttttttt ttttgagaca gagtctcatt  24420
ctgtcaccca ggctggagtg tactggtgca atctcaggtg actgcaacct ctgtctcctg  24480
gattcaagtg attctcctgc ctcagcctcc tgagtagctg ggttcatagg cgtgcaccac  24540
acctggctcg ttttttatatt tttagtagag atgggggttc accttgttgg ccaggctggt  24600
ctcagattcc tgacttcaag tgatctgccc gccttggcct cacgtgcagt tttaggaaat  24660
aatacagaga tccccagcac tcttttccagt tttccccaag ggtaacatct tgcaaagtga  24720
gaggacgata tcacagtcag gatactgaca ttgataccat caagatacat aatgtttcca  24780
tcaccaatca gtggtcatgg tgccttttat agccaaaccc acttctctcc taccttccca  24840
tccctttttt aattttgcca gtcattaatc tgttgcccat ttctgtcatt ttatgaaatgt  24900
cacataggcc gggcgcggtg gctcacgcct gtaatcccag cactttggga ggccgaggca  24960
ggcggatcac gaggtcagga gatcgagacc atctggcta acatggtgaa accccatctc  25020
tactaaaaaa tacaaaaaat tagccaagcg tggtggcggg cgcctgtagt cccagctact  25080
cggggagctg aggcaggaga atggtgtgga cccgggagga ggagcttgta gtgagctgaa  25140
atcacaccac tgcactccag actgggtgac aaagcgagac tccatcttaa aaaaaaaaaa  25200
aaaagaatgt cacataatga atcatatggc atataaccgt ttgagactca gggtaattct  25260
catgagactc atccagcttg ttggtgcatc aacagtttat tccttttttat tgctgagtaa  25320
tttcatggt atggagggaac catggtttaa ctattcaacc attggaggac atctaggttg  25380
tttccagctt ggagttatta tgaataaagc tgctgtgaac attttgtgtac aggtttcttg  25440
gttttctggt ttgttttaaa cagttctagc caggcacggt ggctcacacc tgtaatccta  25500
acacttggaa ggctgaggta ggaggactgc ttgatcctag gaggcagagg ttgcaaggag  25560
ccgaaattgt gccactgtac tccagcctgg gcaacataggc aagaccctgt cattcataggg  25620
taggtggatg gatggatgga cggacggaca gatagatagg tagaaatgta aattacaggg  25680
ctacgctcag tggctcatgc ctgtaatctc agcactttgg gaggcgaagg cgggcggatc  25740
accagagggtc agcagtttga gaccagcctg gccaacatgg caaaacccca tctctactaa  25800
aaatacaaaa attagccaag catgctggca tgtgcctgca atcccagcta ctttggaggc  25860
tgaggcagga gaatcacttg aacccaggag gcggaggtta caatgagcca agatcagcc  25920
actgcactcc agcctgggcc acagagtgag actccgtatc agtactttct ttttattgtt  25980
tttctgttat tatagtttaa gttcattgtt attagattat atactctgta tggcttcaat  26040
tctttttaaat ttgttgaggt tgttttaatg gtcaaagaca tggtctgtct aggtgaatgt  26100
tccatgggct tttagggaaa aaagtatatt ctagtgttgt tgaatggtat cttagtccat  26160
tcaagctgct ataacaaaat accgtaaact gggtgattta taaacaacag aaattttttct  26220
ctcacagttc tggaggctgg gaagttcaag atcaaagtgc cagcagattc agtgtcatgt  26280
gaggacgtgc ttcctgcttc atagataaga ggtacataca cgtttaggag catcgtgtct  26340
tcctggtgga tgaattctgt tatcattagg tgatcctttg agcactttta aaagaatct  26400
gttggccggg cgcagtggct cacgcctgta atcccaggac tttggggggc caaggcgggc  26460
agatcacgag gttaggagat tgagaccatc ctggctaaca cagtgctctac  26520
tacaaataca aaaaaattag ccgggcatgg tggcaggcgc ctgtagtccc agctactcag  26580
gaggctgagg caggagaatg gcgtgaacac aggaggcaga gcttgcagtg agccaagatc  26640
acgccactgc actccagcct gggcaacaaa gtgagaccct gtctcaaaaa ataaaataaa  26700
ataaaataaa aataatctgt ttaatagcct actagtgttc ttcctttact attttattga  26760
gcattaatta atcccaacat tatgtctatg tcaggactga tgacaatatt tggtataaaa  26820
```

```
atttgatagt ctcagaggct gaggcaggag aatgcttgaa tccaggaggc agaggttgca   26880
gtgagctgag accgtgccac tgcactccag cctgggcaac agaacaagac tccatctcaa   26940
aaaaaaaaaa aaaaaaatcg atagtatcat atcctccagg attcaaagtg aacttcaaac   27000
agtcttatgt agtctaaatt ttggaatgca tcccagtatt gagttgcagc agggatttga   27060
gttttttgtga agagagagag gtatatcaga atcttgggta taaactaagg agccatgtca   27120
gaacctcagg tgtatgccaa tgagatagat cagaacctca ggcatgtacc cgatgagaca   27180
gatcagaacc tcaggcgtgt acccggtgag acaggtcaga acctcaagcg tgtacctgtt   27240
gagacaggtc agaacctcag gcgtgtagcc agtgagacag gtcagaacct caggtgtgta   27300
cccagtgaga cagatgagaa cctcaggtgt gtaaccagtg agatatatca gaatcttggg   27360
tatttaccca aagaggtata gcagagtctc aggtatatac tcaagaaggc atatcttgag   27420
gctttaagta tctagctaag gatttatatc aggatctcag gtttataccc agggaggtat   27480
agcagaattt ggggtataga tctaaggagg tctatcagtc tagagcatat agccaaggaa   27540
ctatatcaga acctcaggca cctacccaaa gaggcatttt aggactcgta aggaggggt    27600
agatttcaaa agtgtagtct aacagtttat ctactttgaa atttaaaaca atattaaagg   27660
aaaacatgaa atatttctat ctgtcagaag gtgacatgaa ttttaaacaa ttaagaaata   27720
tactggctgt ggccttgtaa ccaaattatt atgcctatag aaattacaga ctccatttc    27780
caggatagaa taacagggac tgacttacct tctcatctga gataacaaaa cctccataca   27840
aatacatgaa acaatgttct tcaagatgct ggacatcaga cagtgaaggg cactgatggt   27900
tgtaagacaa ggtgagaggt gtggcttgag agagtttcca ggttgcagtg cagggagagg   27960
ggaaactgag gcagatcttg gcagacttcc tcagttgaca aaatagagct gagagtccag   28020
ggagaccatg gtgtatagat tatccaaagc aaagtatgag aggtgcaagc catatacaga   28080
gggactccag agatcttacca atgtacttct tggtgcatcc atatgagcaa aactacttga   28140
ggccaggaaa agaaccatct gagaggatta gaaggaacag tgcccagtac ttgtgccagc   28200
caggaatggt gcctgatact cacgcagggc caggaacagt gcaggatgt gagtgtttgt    28260
taggagaggg aggtatatca gaatcttggg cataaagaca agaaaccata tcagaacatc   28320
aggtgtgtac caatgagata gatcagaatc tcgggtgtat aacagtgag atagatcaga   28380
atctcagatg tgtacacagt gaagcagatc agaatctcag atgtatacac agtgagatag   28440
attggaatct caggtatgta cccagtgagt ccaagagcat ggtgctggca tccggtgagg   28500
gccttcctgc tggatcgtga catgaagcaa ggcaaagagc ctgtcagctc agggctctct   28560
tcctcttctt ataaagtcac cagtcctatc atgggggccc caccctgatg atcttataat   28620
cctaattacc tcccaaaggc taccttcaaa tgctatcaac atatgaattt ggaaactaag   28680
tttcagcac atgaaatttg ggggatacat caaagtata gcaaatatta catcataacc     28740
agtaggattc atcccaggaa atgccaaatg gcttgataat caaaaattaa tgtaactcat   28800
cgtattaaca ggatgaaaaa gaaaaaccat gtgatcatct tagtagatgc agaaaagcag   28860
ttgattaaat cccacattca tttctaactt aaaaaaacaa ctggattttg acagaggtgc   28920
aaaggcaatt tggtagagaa aggacagtct tttcaataaa tggtgctggt gcaatggtta   28980
tccatatgcc caaaatgaac tttgacccat gcctcatgcc atacacaaaa attaactcaa   29040
aatagatcag agatctgaag gtaaaattta aaactataa acttctagaa gaaaacacag    29100
gagaaaaatc tttgtgacct tggtctaggc aaagatttca tagatatgac accgagaaca   29160
caatctgata aagaaaaaaa tcaataaatt gaacttcatc aaaatgaaac tttttactgtt   29220
caaaagacag ttttaggaga atgaaaacac aagttacaca ttgggaagaa atattcgaaa   29280
agcatttgcc tgataaaggt attgtagctg gaagacagaa aaaattctca aaactcacct   29340
agaagaaaat aacccagttt taaaaatggg caagagatct gaacagatc attgtcaaag    29400
aagatagatg aatagcaagt aagcatgtga aaaattctca atgttatcag tcatcagagc   29460
aatgcagatg aaacctacag tccccatgct aatgttctac aacttacaca gtggtggtat   29520
gataccacta catgcccatt tgaatggcca aaattagaaa ggttgaccat accaaacatt   29580
agccagtata tgcaggaact agaactctca tctttgctga caggaaggta aaatgataca   29640
aacacattga aaaacaggtt ggcagttgct tttttttttt tttgagatgg agtcttgctc   29700
tcccaggctg gagtacagtg gcgcgatctc agctcactgc aacctctgcc tcccaatgaa   29760
ttagaaaaat aataataaag gtaacaatag cagtaataat aatagaaata atgatagttt   29820
ctttaataaa aatgctgttt aggcccagac tgaaaggctt taagtaacca ctccccccaat   29880
gaagttagag ttaagaaaga atattaattt tccttgtgtg aaacattaat cttatctagc   29940
ctccatgtat tttgtaagtt ctgtaaattc ctgtttccc tgcacagctg caagttcaca    30000
aggcagataa gcttaagctg caaaacatgt ttttcttaag atgtaaggca tgtcacaaga   30060
atatcacaag atgataacgg cctttattct cacttctgta tgcctgcttc ctgcctcaca   30120
tatttcctgc ctcaagatgc gtaaaaggta cttgccttct ttgtttggtg ctctgacttt   30180
ctggatgcaa gtccactgag ccagtgtaca ccttaaataa atcctcctga acccatcaa    30240
tcgctccagt tctctgattt cccactacat tttctggggg ctcgtccggg attggagatg   30300
gcagattttc tgtctcccTT gcctgtgaa ctggagcccg ggtcgaggga gacctgggac    30360
ctttggtgcc aatgggagga ctttagcccg gaaaggagat tggctctcct gcatcccgat   30420
gtccttccta gacagcacaa cggaacctat aaaggggttg caggacggtt ccagcagggg   30480
ctggggatgt tgagagtagc tcactgattc agatgacagg gttttgccat gttgcccaga   30540
cccagagggg ctgggacag tgagagtagc tcactgattc agatgaaact tacacccttag   30600
ccgatgcagg acacgagagt ggctcactaa gttggtcagg aaagaaactg aaaatgggaa   30660
gagtggcttc ctgccttgac taaggatcgg gaactgggag cggggaggtg tgtgaaagaa   30720
atggttccgg gagggccgtg atgtgggag acacagatct cttagcacgg actgtgtgct    30780
ctgaggcgag tgtgtgattg accagaacca gggcatcaca tacagctgac aggagctgcc   30840
ccacagctgc agcaggctgt ggcaggaata ggtactctc ctagctaagc agcacctgaa    30900
acttccgtaa taggaccca tctggtcagt ctggaacgaa agtgagagtg agtgtgcatc    30960
acaaagggcg ggatgggagg aaaagcatcg aaacccactc ctctggggtg catgttaaag   31020
aattttaaga aaggttttgc tggagattat ggaattaagt tgtcccccc aaagattgag    31080
ggttctgtgt gaagtggaat ggccttcttt taatgtcggg tggccagccg agggtacaat   31140
aaataggaa atgattggtc atatattag ggtagtgact ggggttggag gacacccctgg   31200
gcatccagat cagttcccat acatcaattc ctggatgatc gaacactaga catgcccaaa   31260
atggttacag ccttgtctgg caacttactg taagactcta gtgacctgag ccgaacctaa   31320
ggcagttaga gggccccctt caccagacac ctcaggtgga aagaaaagc cacaggaaaa    31380
ttaggaaaga cctgttctac ttcactggga tcaagtgatt ctcctgcctc agcctcctga   31440
gtagctggga gtacgggtgt gcaccaccac gcctggctaa ttttttttaaa ttttatttt    31500
agtagagacg gggttttgcc acattggcca ggctggtctt gaactcctga cctcagacag   31560
```

```
tctgcctgcc ttggcctccc aaagtgctgg gattacaggt gtgaaccacc atgcccagcc   31620
agcagtttct tataaagtta aaccaatgcc taccatgaga tctggcaatc ccactcctaa   31680
gtatttggcc aagaaaaaag aaagcatata ttccatacag agtctagtcc tgaatgtcta   31740
tagctgcttt atttataata gctcagactt ggaaaccatt cagatgccat taataggtga   31800
atatattctc aaactgtggt tatccataca atggagtatt actttgcaat caaaaggaat   31860
ggcctatgaa tacccataac aacatggatg aatgctgaaa taattgtgct gagtaaaaga   31920
agacaggaaa aataagtata atacatactg cttgattcta tttgtataaa actagaaagt   31980
acaaactaat ctgtaatgac aggaagcaga ccagtgacag tgggcatgga ggggcaagag   32040
ggagagatta gatgggcaca ggagagcttt gaggatgagg ggtctgcgta ctgtctcggc   32100
tatgatagtg gtttcacagg ttgatacata cggcaaaaaa taccaaattt gtacacttta   32160
aatatgtaca gattattgta tgccagttac atgtccataa agctttcttt tgttgttttg   32220
tttttatttt attttttgag acagagtctc gctccatcgt ccaggctgga gtgcaatggc   32280
accgtctcag agcactgtaa cctccgcctc ccggggttcca gcgattctca tgcctcagcc   32340
tcccaagtag ctgagactac aggcatacgc caccatgccc agctaatttt tctattttta   32400
gtaaagacag ggtttcgcca tgattgccag gctggtcttg aactcctgac ctcaggtgat   32460
ccacccacct cggcctccca aagtgttggg attataggca tgagccacag caccgggccc   32520
ataaagctgt cttttaaatg aaaaaaagtt gtcttgaaat aagcattaga actgtggctt   32580
tggctctgaa atcctcatct gaggacccac actcgggtgc cccaatgtgg cggtgcttac   32640
agaaatgact ccatctgcta aatgagtaaa tgggtaattc tccactgaac acacactcgt   32700
ttagcagcat aagcagcaag agttcaggta atcctcacat tgcaatttgt cattagttta   32760
aacttccagt cttttgtttta aaaacacatt agaataatac tacattttcc ctcatctcta   32820
aacttgactg aagactccaa gagagagtaa tattcatcaa aggatcatc tactcaacac   32880
agataaactg ggaagaaaaa ataacttgtg agtaattcag aatctggatt atcaggtcag   32940
gctcaatggc tcacgccagt agtcccagca ctttgcgggg cccaggaggg cagatcactt   33000
gagttcagga gtttgagacc agcctgggca acatggcgaa accctgtcta tacaaaaaat   33060
agaaaaatta gccaggcatg gtggcatgtg cctgtagtcc cagttacccg ggaggctgga   33120
gtgggaggat cacttgagcc tgggaggtcg atattgcagt gagctgtaat tgcaccatgc   33180
actccagcct gggtgaaaga aggaaactct gtgtccaaaa caaaacaaaa caaaacaaaa   33240
aaagctaaat tatcaaatgt ctagatcgtt gatggttgga agtaaagttg agaaatgttc   33300
acactgggag atgacacaca gtaaaccaca cagagggttc taacgtgggtt gttagaagca   33360
gaaactagag gcttgctgcc tgaggtcaaa ccccggtccc ggtggttctg tgccccagcg   33420
catgttgtgg tagcctctct gtacttcagt ttcctcatct gtaaagtaaa cataatgata   33480
atgcctgcct catggggttg ctgttaccag gaagtgagtt aatgcacatt aggttcttat   33540
ttatgacagt gcctggcata ggataagggc tcaaaaagtg ttagctggaa ctatctcat   33600
tatcaacatc tctaatttat tgcagggttg gatctgaaaa atggctgatg atgatttgat   33660
gatgacttca tttttataaa acaataatat tgcagtgcaa attaaacaca agcaacctgc   33720
aacacgccac tgcaagttgg atgtctgaaa aaggtgccat gagttacctt ctaaaacatc   33780
ataagaaacc atgttcacca ataattacca taataggaga gaagtaccaa gtaccatggg   33840
gagacagagt ccagaatctc agagagagac acagttacct tttagttaca ctaatgggga   33900
aaacaggagc tttgctaccc ttgcacctga tggagggctt ctctgaatat agggctatgg   33960
ggtcagaagc cagtttcctc ccatatttag aaggtttcca actgttatct ttcacttccc   34020
atgttgctgt tggaaaatcc aaaagtattc tatttggcca ggcacagtgg ctcacacctg   34080
taatcccagc aatttgggag gccgagatta cctgaggtcg gaagttcaag accagcctgg   34140
ccaatatggc aaaaccctctt ctctacaaaa aatacaaaaa ttagccaggc gtggtggcgc   34200
acgcctgtag taccagctat tcgggaggct gaggcacgag aattgcttta acctgggagg   34260
tggaggttgc agtgagctga gattgtgtca ctgcactcca gcctacgcga cagagcaaga   34320
ctccgtctca aaaaacaaaa aaagtattct gttggatcgt ttgtgtgcga cgtgttttc   34380
cctctcagaa agctcgtagg gtcttctctt tgtctccagc atggtctgga atttcccagt   34440
gagtgaccat ctgtgtgtgt gtattcatcc atttccatgga gtccctgctg ggcccttgca   34500
atctggaaat tcatgccat catttctgag aagttatcct gaacgtactg gttggtggtt   34560
tcctgtgctc catgttcttg cttcctgctc ttcggagctc ctgttatttg gttgagtttt   34620
gtctcctgga ctggtcctct cttacttctc ttgcttctcc catgttccat ctgttttcac   34680
tctactttct gtgagatcag gcccttttat ttccaaccct tctattaggt ttgcaattga   34740
gtttgtaatt ccctagaaaa gttcttattc tctgaatatc cctttgata gcatactctt   34800
cctttttcat gagtgcagtg ttttcgcatg gctctcatca gaacatgcta gtgtctccca   34860
tttctcataa cttttctagag tgaggaccat ttgaacttgg agtgccctca ttttaaaact   34920
ctgtggttga ccttgttccc ctcttttgct gctgcttttc accagacttt gaagaagcag   34980
aagtacattc agaacttgtc tgctctggca aagacaata ctgttggctt aatctaaaaa   35040
ttgaagaaga aagctcaagg agagaagttt aaaaaatatac cacctctggc tgggcgcggt   35100
ggctcacatc tgtaattcca gcactttggg aggctgaggc aggtggatca cctgaggtca   35160
ggagttcaag accagcctgg ccaacatggt gaaaccccgt ctctactaaa aatacaaaaa   35220
ttagccaggt atggtggcag ccgcctgtaa ttccagctac tcgggaggct gaggcaggag   35280
aatcacttga acccaggagg cagaggttgt ggtgagccaa gatcacgcca ctacactaca   35340
gcctgggtga caaagtgaga ctccgtctcc aaaaaaaaaa aaaaaaaaa aaatatata   35400
tatatatata tatatatata tatatatata tatatatata cacacacact aaccttcagc   35460
atataggact attgcagaag ggattatctt tctacttggt tggttcctct tggtcttgag   35520
caaatttga cttccctgag ttggcccta aaagttaaag ggaaagggcc ttttctcttt   35580
cctttaaaac caatatggca tatttgctga gaacttagat accacaggat tggcagtgta   35640
gacttacatt catgaccgg atgccatcag ccaaccttga gtaatttgca gcacactgca   35700
tcattttatt taagtaatgc gaagtccttg acatgtctca gacattgtct tggttacttg   35760
taaggtctca cataaatcta attttcctct ttctctgccc tttctggttc agctcagttt   35820
attcaagggt gtatttgtgc aacacacttg aataaggtgt ggtcccgcct ttgtagatgt   35880
tatagtttgg gaagaccagc cgggcagaga gaagagcatg attcaaggat gaaggcgtgg   35940
gctgggggcc gagggagcaa ggattcccag taacgaggga gaaggagca gcaccatgtg   36000
cccattactc tatagacatc tcgaaccacc tggccatgta gctgtcatta acctaaattt   36060
acagttattg aaactgaggt tcagccaggc gtagtggctc acgcctgaac acaggaggcg   36120
gaggttgcag tgaccgagat tcacgccact gcactccagg ctaggtgaga gagcgagact   36180
ctgtctcaaa aaaataaat aaataaaga aagaacaaa actgaggttc aaagaaatgt   36240
acagtgctcc cccccttatc caaagaggat acactccaag cccccacagt ggataccgta   36300
```

-continued

```
agcctcagat agtatcaagc cctatatatg ctatgttttt tccctgtata tgcataccta   36360
tgataaagtt tataaattag gcacagtagg agactaacaa caatgataat aaaatggaac   36420
aattataaca tacactgtaa caaaagggtc tcttcctctc tctctcagaa tatcttattg   36480
tactgtactg ggggtaacta aaaccaagga aagtgaaacc atggataagg gatatctact   36540
gtataaggtg gagttttcaa ggtcatagca ctgccttccc ctgaggttgg ccttgcagcc   36600
tctctaggca ctgctgctgc tgctaagaac ccctgtgagg tgaacactgt aagcatcatc   36660
attgcttctc agaagaggag acctggctta cagaggtcaa gcctcaggta ccttaaacac   36720
catttttaaa ctgaactcat ggccaggtgc attggctcat gcctgtaatc ccttctctcc   36780
atgctcaaaa cctgccctcc ttgtctttat attccaaatt tcgtgggtgc cacctcctcc   36840
gcccagtgac ttaagccaga gcatacattc atcctagact ctgtcccagg tccctggtcc   36900
aggcagctgc cagttgtcag gatcagctct ttatctcgca gtcctcctgc ctcttgtgtc   36960
attacccagg gctgtcacca tctttttcttg ggacagttac aacagccccg taaggagttg   37020
tgctgcttct agtcttgttc cctttgaatc tggattcctt cttgccatca agacatcct    37080
gatacaaatc tgatcacgtc acacttccct tcaatagtct tccatgctc cttattgttt    37140
taggatgaaa tccaaactcc taaacatggg gattaacaat gtgccatgat tggcactgct   37200
ggcctctcct acctctgcag actcacctct tgccacttct cccttgaggt agatcaaaaa   37260
tggtcacaag ttcttgagg ctcttccat caagaggtag agtttatttc cccacctctt    37320
ggatctggct tgccttgtga cttgctttga cccacagaac gtaacagaaa ggacactgcc   37380
taacttacaa atgaggtcta ccttaagagg ctttgcagat tccacattca acctcttgga   37440
atgctgccac catctgagaa gcctgaggtg cctctgtga ggatgaaaga cttcatggtg    37500
agaaatacct agcgaacagc ctggcaccag ctaccaggca tgtgactgag gccatccagc   37560
catagctgag ccacaaaatg accacagcta tgtgaattat cccaggtcag accagtagaa   37620
gagccacctg gctgagctca gcccaatttg ctgacccata gaattgtgaa caaataaaat   37680
ggttgtagtt ataagccatt aagtttcaga gtttgttaca cggtaacatg taactgatac   37740
aactcttgga gccagttgtt cagccattct caaccactta ttcaatgatg ttttgggcca   37800
tatatgcaga tatgctgttc cctttcctt gaaatgccc ttaccctcct ttctgttggg    37860
ttttcctatg gaatatccag tcagcccttta ggattcatct tgggtgtccc ttcctgtatg   37920
taggctccct ggcctccag gattcccca gtaacagccc tcatcatgct gccttttgcaa   37980
ccatttgttt atttgtacct ctcacctgct agttgggcaa gttactcact tctctcaacc   38040
tctgcatttt tcttctttat aaatgggacc aataatacct accctgccct ggcgtggata   38100
gattaaagaa aaaaaatca tgcagctgcc attgagggcc tggcccacgt gtgatgttca    38160
ataatattat ttctccttgt tttccttccc gtgccagtgc cacaccccc tgtcccagtg    38220
cactggggct gtggatccct tcaaagctga gattgcctgt ctgtggtctc cagcgttaag   38280
cacagtcatt agctcaggtg cgtactcatg tgttccacga gttcaagcct cagccctgta   38340
aagtttgcct gccgtgtatc tgatatattt ctgctaaaac ccattaggcc tttcttgctc   38400
tgaaatgtca tcgttagttg tgtgtcactt cagttttgta actggccagg ccactgcgcc   38460
caggctgctt cctcgtcatc tggctgctaa atgcttcaac cttacctgcc ttgctatgcg   38520
tcccatcctg tatcaggtca gagctcttga gtggtgaata caaatttcat ttcagttgac   38580
ttgattct tgtggcaggc ctctcggcct actctaattt gattgcaacg gacacaaaat     38640
gtgtccaaac ttgcagcttt tcttctctta ttttgatatc accatccaca aaggtaagat   38700
atttaaagc aataactaca aactttctga aaattatgaa gaagtgctgg gttttaaatg    38760
gaagtcatat agtgtgaact ttgtgtaaag tccgtaggga gttttcttgg aaatggctgg   38820
gaacattctt tttgcacctt tgaagataaa ggtaggtgga ggagctcaca gctcttgtgc   38880
catgttgggc ttgtcactct tgttttatgtg ccaaattctt ttgattacaa aattttaagt   38940
ttaatgcttt aggtattgtt gggcaagatc tagatgtatc tagttaaatg taggtgatat   39000
gcaaactatt tatgatgtat ttgatttaaa ttcattaaga tagagtgtct ttaccaccat   39060
tatagtctgg tccttttcct tctgtttttaa atgtgtttcc attggcattt tctaaactga   39120
ctttgttagc gtgttaatca tttggcactg gtaatgatta atctttttctt tctttctatt   39180
tttttttcttt ttttttttttg agacagagtc ttgctctgtc accaggctgg agtgcagtgg   39240
cgcagtctca gctcactgca acctccgcct cccaggttca agtgattctc ctgcctcagc    39300
ctcccaagta gctagggact acaggcacgt gccaccacgc ccagctaatt tttgtatttt   39360
taatagagat gggggtttcac catgttggcc aggatgctct cagcctcttg acctcgtgat   39420
ccgcccacct cggcctccca aagtgctggg attacaggca tgagcgactg cgcccagccg   39480
tgttcatcta tttctgtgaa ccgatgctag gtgaaggtac agagggcttt ctagcttctg    39540
ggtttgttta ttctgaaatg ttatttttaaa tcttagccca acaaattgag cgaaaagact   39600
tctagatgtt aaaatatgata ttcaaaaaat ataaagacaa ggtgataaat tagaattggt   39660
gggaaagaga aaaatctgtc ttctgatggt cacctgcccc agcaacacta ctcgtttgag   39720
aagacttcca tcctttaccc tcaaagtgtt ccatgaggtt ggatcagaca tcatttagca   39780
aagaaagatg taaatagatt tctgtagggt ggcattatta agcatattaa gtggttacaa   39840
tacagtaaat tagagggagt agtacagaag cataagcagt caaaaaagtg aaagtctaac   39900
gttcgtaatt attgttctgg aggctttttgt atcacatata agttccaggc tgggtatgat   39960
ggctcacacc agtaatccca acacttagag gccaagccgc gtggatcgct tgagcccagg   40020
agttcgagac caggctgggc aacatagtga aacctatctc tacaaaaata caaaaattag   40080
ctgggggtgg tggcagcgcc tgtagtccaa accacttggg agctgaggt gagaggatca    40140
cctgggcccg ggagatcaag gctgcggtga gccatgatct tgccattgca ctccagcctg   40200
agtgacagag agagactctg tctcaaaaat aaaaaagttt tgagtgtgaa aattcaagct   40260
caattccatt tgttggttgt cttgagtgtc tgatcacata gaatataaag atgttttgat   40320
agttgggaca gtattcagct acctgctatt taatacatta tttcagaaaa tatttacaaa   40380
gggggctggg cacagtggct catgcctgta atcccagcac tttgggaggc cgagtgggc    40440
ggattacctg aggtcaggtg ttcaaaacca gcctggccaa acatggtgaa accacatctc   40500
tactaaaatat acaaaaaatt agccgggcgt ggtggtgtgt gcctgtagtc ccagctactc   40560
aggaggctga ggcacgagaa tcgcttgaac ccggaggcg tggggttgca gtgagccgag    40620
attgcacaac tgcactccag cctgggtgac agagtgagac tgcatctata aaaacaacaa   40680
caaaaaagaa aattatttgca aaggaccttc tgggtccaag aacctcatgt ccaataacag   40740
ggtgcacacg tgggtgagac acggcagctg ctctccagaa gcccacagtg gaggggtttc   40800
ccttcggtct ccttttattc caagcaagtg gcaaaactac tttactctta atacaaacca   40860
cttcctttta tcacaggacg cttcccaagc tctgcaactg ttgctcctga ggaagggagt   40920
ggaactgata atctgttcct cccctattgtg ttcagtatgg ttttttttttt ttttttcctt   40980
ttgctggctt tgttttcctg tccctgtgat gattaaaatt cactctgcaa attagatcac   41040
```

```
ctttcccacg cagagtccct ttgacttctg ttctagatat ccattacatt tttgtagtct  41100
tcggacacac tgtgtgtgcc gctttgccct ctgggtgaca gcaggctgtg gctgcgcga   41160
cagagctgag gtgaattctc acagaccatc actgggttac tcctggagta agtaattccc  41220
aagagctcct tctgtgcaga tcgttagaaa tagatattga ggccaggcgc ggtggctcat  41280
gcctgtaatc ccagcacttt gggaggctga ggcgggcaga tcacgaggtc aagagatcaa  41340
gaccatcctg gccaacatgg tgaaaccttg tctctactaa aaatacaaaa gtagccgggc  41400
gtggtggcgc acgccgtag tcccagctac tcaggaggct gaggcaggag aatcacttga   41460
acccgtgaaa cggaagttgc ggtgagccga gatcacgcca ctgtactcca gcctggtgac  41520
agagtgagac tccatctcaa aaaaaagaga aagaaagaat tagacattga acacctgcta  41580
cacagcaggg attgtgctag aagtatggat gcaaagatta ggtgaatatg ttccctagcc  41640
tcacaaagca tacagtctag taggagagac agacacgtaa aaagtttcaa cagcacagat  41700
aatcagggct acaccagaat tgggcccaag atgctgcagg aatctatagg tgaatgggtt  41760
tcatgaagga agagcttctt ctcccattta taactcattt tagcctaatc ttccaaacag  41820
tcacgcatct aagagcaggt gatgcagaaa ataccccgt gttagttatg aattaccgtt   41880
ggaatccttc cagtgtttgc acctgccctg tgctcgggta acataaaaca gtgatataat  41940
ttgatgctca cttcctcttg tatttgtctg tttttaagtg ttctacaatt ttcatatact  42000
ctgtttcatc gttctcaaag gaatattttg attgataaat gtttagttag taagacctaa  42060
aaactgaatc tcagtagttt gagcttatga tatacaagat gcaactctaa cattttaaatt 42120
ggaagggaaa tgtcaaaaag ataccctgac tcttgtttgt tgcaacactg tttacaatag  42180
ctaagatttg gaagcaacct aagtgtccat caccagacaa atagataaag gaaatgtgat  42240
atatatacac aatggagtac tattcagcca taaaaaagaa tgagatcctg tcatttacaa  42300
caacatgggt ggaactggag atcattatgt taagtgaaat aatccaggca cagaaagaca  42360
aacttcacat gttctcactt atttgtgggc tctaaaaatc aaatcacttg aactcagaga  42420
gattagaagg atggttacca gaggctggga agggtggtga ggggtgggg gcagtgaaga    42480
tggttaacag gtacaaaaaa ctagaaagaa tgaataagac ccactaggtt ttttgttgtt  42540
ttgttgttgt tgttgttttg agacagagtc tcactctgtc acccaggctg gagtgcagtg  42600
gcatgatctc ggctcactgc aacctccacc tcctggggtc aagcgatcct cctgcctcag  42660
cctcccaaat agctgggatt atgggcacgc gccaccacac ctggctaatg tttgtatttt  42720
tagtagggac cgggtttcac caggttgaac aggctggtct caaactcctg acctcaagtg  42780
atccactcgc cttggcctcc caaatgctca gattacaggc gtgagccacc gcacctggcc  42840
actgtttgat agcataatag ggcgactata gtcaataata acttaatgat atatttttaa  42900
ataacttaaa gagtataatt ggattgttgt aactgaaagg atcaatgctt gagggcacag  42960
ctaccccatt ccccatgacg tgtttagttc acattacatg cctatgtcaa agcatctcat  43020
gtacccata aatatataca ctgaagtatat accacaaata tttttaaataa tttttaaaat 43080
aaaaaaataa attgtaaggg aaagaaaatt atgaatttag aaatgtaaaa ggtctcaggt  43140
aaggaaggaa tgagaggatc atgcagaacc tcccatcatt gctgggactg gaacagaagc  43200
cctacctttt cccaacaccc tatccacctg tccctcacct ctcagctttt gtgagactct  43260
gtctgtgcta tgaaactgaa gatctaattc agtgctgttt gcattgtctt gcctcctgga  43320
ccagaggttg cagttgttga gaaaagggat ggttggttat gccttgatcc ccccagagc   43380
atttggggca taggacacgg gaactggcca gcctggttca ctcttctcga ttagctggac  43440
agcggcatgt catgtgggta ataggaaggg gtggggactt ccccgggata ttctgctcct  43500
gatcagaagc gccagtgatg tgggggagc cccagcacca gagcatgctg ggagggcgtg    43560
cagggtgggg caggtgcccg tttggcctct gctgtctatc tggggatgc atccaaaggc   43620
aactgttcct tatctgctct tgttgggagc aaggaagggc caatttgttc aatgatccgt  43680
atacagccag tccctctggc cagagttcaa gacagtattg cctcactcta tatagagatt  43740
gtatcttggt tagctcttca ttcatagcaa gaccaatgtt tctgtaaatt aatcctggta  43800
ttgtttaaaa gcaactaaaa atgatgaaat tgtaaaactt tgaaactcc tgaatataac   43860
gacaagcaaa ctaacattgt tttattggtc gatgctcctg gccagaagag agaattattag 43920
cagggataaa aggcataggc cacatgcatt ttccacccca gtgctgagaa cacgatgggc  43980
gaaaaggga ggtggccaca gcccatccat cacacagtc ctgcccatct acttgctttt     44040
tccttttttt ttttttttt tttgtgaca gagtctcgct ttgtcaccca gactgagggg    44100
cagtggtgca atctcagctc attgcaactt ctacctccca ggttcaagcg attctcctgc  44160
ctcagcctcc cgagtagctg ggattacagg cacctgccac caagcccagc taatttgttt  44220
gtattttag tagagacggg gtttcaccat gttggccagg ctggttttga actcctgacc    44280
ttaagtgatc agcccacctc agcctcccaa agtgctggga ttacaggtgc gagccaccac  44340
gcctggcccc agctacctgt tttctttctt ttttttttt tttttctttt ttttgagaca  44400
aagtcttgct cttgtccccc aggctggagt gcaattgcat gatctcagct cactgcaacc  44460
tccacctcct gggttcaagc gattctcttg cctcagtctc ctgagtagct gggattacag  44520
gcgcctacca ccacgcccgg ctaatttttg tattttagt agagacgggg tttcaccctg    44580
ttggccaggc tggtttcgaa ctcctgacct taagtgatct gcccgcctca gcctcccaaa  44640
gtgctgggat tacaggtgtg agccaccatg cccggcccca gctacttgct ttctattggg  44700
atgaacctca tggttaatac agttagttag tgactgcaac ttttgaactt tttgttcata  44760
gtgaaaaata ttttaagtaa tgcttacccc attatgtttc ttgtcatttg aaaaaaaatc  44820
tcccttcaga cagaaatgcag aataaaatac tacagacagg tcccagcctg              44880
acttatgcta gtaggttaca gagaaagaaa gtcttctaaa ccctatgaaa ggttaacagt   44940
tctcttattt ttccctgtgt gctatttgat gatttccctg tgaactttga tgatttattg   45000
ccagaattcc aaacataata tgtgaatttc acaaaaatgg atgaaatgta tctatttttc  45060
attggtagaa gaagccaaaa catcccttcc tcaccgcact aaaagctgtt gtttacatga  45120
agcaaacctc aaatgtgaac atatttttac gcaaatgcat ttaatgggtg aatatttgct  45180
ttgggacggt attctttact ctatctggag agtctggcgt tccgtaatca ccatgtgatg  45240
acggctgccc tgacagtggc tggtagcagc acatacccccc gagcctctcc gtggtgtgcg 45300
ccgtgggcac catgtgacca ttttcagaaa ggaagacagt tctggaagct aaaggtcacc  45360
tagtcagcct cgttgggtga ttgatgactc agctgggttc agggaggtgg acccgaggca  45420
gagcctctag aaggcagcgg tgggcagggc ggttcaggca ggcagcacct gggcaaaggt  45480
gcagacgtgg aatcctgaaa gcaattctca gcgctgctgc gtttccagga ggtagaagaa  45540
cagtgacaag tgcacagtcg ggtagggaca aatgtgaaag ggctgggaac agtgtgttca  45600
ggagactggg cttcaatctg gaggtctcag gaagtggttt aggatgttc agcgagagca   45660
tgatacagac taacccagga agaaccgctg ctttgtcact tataccccta tggaaatgcc  45720
gttcgctttg ctagttgaaa tagcctacca ttgtctggga ctcacccagt tagatttgtt  45780
```

```
tggactccac aaagtattct tgaccataca atcatggtcg aggacccccct acatgagctg   45840
ccttcatggc tacagggaga gcacaccaaa gtggatgtca cacccagcac acatgccacc   45900
ggcttggccc tgcgcccgc agcctgagcc acactggctg cctgttcctg aatgtgcca    45960
acatgtttca gtcctggagc ctttgcactt ggtgttctct tcgctggaac attctccccc   46020
aagacattta cacagcttgc cccctcattc cctgaggtta tctcctgccc cctaatcagt   46080
gaggccttcc ctggcctcac cccggacact ccacacgtgc attcatttcg ttgttcacca   46140
tctgtgtccc agttacaagg gaggctccct gagagcaggg atctgatttt tgttagttgt   46200
tgttgttgct gttttgaggt ggagtcttgc tttgtcgccc aggctggtgt gcagtggtgc   46260
gacctcagct caccgcaacc tccgcctccc atgttcaagc ggttctcctg cctcaacctg   46320
ctgagtagct gggattacag ggcctgcca ccatgcccag ctaattttttg tatttttagt    46380
agagacagag tttcatcatg ttggtcaagc tgccctccaa ctcctgacct cgtgatctgc   46440
ccacctgggc ctcccaaagt gctgggatta caggcatgag ccactgcacc cgaccctgtt   46500
ttttgtttgg ttttggtttt ggtttggttt tggtttttt ttgagacacg gtctcactct    46560
gtcgccccgg ctagagtgtg gtggccacat ctcggctcac tgcaacctcc acctcccagg   46620
ttcaagtgat tctcctgcct cagcctcctg agtagctggg attacaggca catgccacca   46680
cacccagcta atttttgtat ttttagtaga gatgggtttt gccatgttg gccagtctgg    46740
tctcaaactc ctgacctcaa gtgatccgcc cgcctcggcc tcccaaagtg ctgggattac   46800
aggtgtgagc cactgtgccc ggcccaggga tctgtttttg tctccgctgt gtccccagca   46860
cctcaaacat attgtacgga gctgcgacga ctgcgcagtc agtgatgact gagagattcc   46920
tggccccgtg ggcatggct ccttcaacag tttgttgttt aaaggttctt cactttctca    46980
gcgtgctgat caagagacaa gcctggagga gaggctcagt ggtgctcctg tgtagatgat   47040
gaattcaggt gtatcttgga tggtaaatga cgttgcattt aaaaccaagc aagtggccag   47100
gcgcagtggc tcacacctgt gatcaaagca ctttagaagg ccgaggcggg cggatcacct   47160
gaagtcagga gtttgagacc agcctggcca gcatggtaaa aacccgtctc tactaataat   47220
acaaaaaaac tagctgggcg tggtggcggg cacctgtaat cccaaccact cagaaggctg   47280
aggcaggaga attgcttgaa cccgggaggt ggaggttgca gtgagctgag atcgcaccac   47340
tgtactccag cctgggcgac aagagcaaga ctctatctca aaaataaaaa aaattaaaaa   47400
ttaaaattta aaattaaaac aaacagccgg acgcagtggc tcactcctgt aatcgcagca   47460
ctttgcgagg ctgaggcgag cggaatacga gctcaggaga tcgagaccac cctggctaac   47520
acagtgaaac ccgtctctac taaaaaaaaa aaaatacaaa aaattagcca ggcgtggtgg   47580
caggcgcctg tagtcccagc tactcaggag actgaggcag gagaatggtg tgaacccggg   47640
aggcggagct tgcagtgagc cgagattgtg cccctgcact ccagcctggg caacagactg   47700
agactctgtc tcaaaaaaaa aaaaaaaga ataaataaat aaataataaa aataaaaac     47760
aaacaagtga acgttgttat acgtcagtct taccaattgt tcctctttcc tcccagtagc   47820
ttggagctcg gcggcacaac cagcaccatc tggtcgcgat ggtggacacg gaaagccac    47880
tctgccccct ctcccactc gaggccggcg atctagagag cccgttatct gaagagttcc    47940
tgcaagaaat gggaaacatc caagagattt cgcaatccat cggcgaggat agttctggaa   48000
gctttggctt tacggaatac cagtatttag gaagctgtcc tggctcagat ggctcggtca   48060
tcacgggtaa gtgtgccgtt tcctagaaag ttttatttag aaatgtttct tcctccaaga   48120
aaactgttct ctctttttttt tttttttttt tttgagacgg agtctcgctc tgtcgcccag   48180
gctggagtgc aatggctcga tctcggctca ctgcaggctc cacctcctgg gttcacacca   48240
ttctcctgcc tcagcctccc gagtagctgg gactacaggt gccgccacc acgcccagct    48300
aattttttgta ttttttaatag agacggggtt tcactgtgtt agccaggatg gtctccatct   48360
cctgacctca tgatctgccc gcctcggcct cctaaagtgc tgggattata ggcgtgagcc   48420
accgcgcccg gccgaaaact gttctcttta gctggaaaag aagtcacact tttttgcaaa   48480
gaaagcttca gacgtggtaa agcatgacct ccagtgcccc tgggccctgg aaggcgcgtg   48540
tcacggctca cggtgccccc tctttgtgaaa gccatgcaca catcaaacag tgcttgagat   48600
tcagtcacgg ggaacagcta aagtacacag acccctaaccc cagcaagccc gcgggggcda   48660
gctagacatt tttaagagga gacgtgtgca agggtctgca tagaggtact gttggtaaga   48720
gggaaggatg ggaaacaagc tgtacatgcg tcaaagggaa acagataaat tgggatgcat   48780
ttatacagtg gtatatactt catagcaatt taaaagaaca gactaggcta ggcgcggtgg   48840
ctcacgccta taatcccagc actttggaag gccgaggcaa gtggatcact gaggtcagg    48900
agcttgagac cagcctgacc aacatggtga ggccccatct atacaaaaaa atttaaaat    48960
taaaaaaaat tagccaggca tggtggtgca tgcatgtggt cctagctact caggatgctg   49020
agggaggagg accacttgag cccaggaggc cgaggctgca atgagctatg actgccactg   49080
cactccagcc tgggtgacag tgagaccctg tctttaaaaa aaatttttt taagcaacat    49140
tgaatgaaaa taaacaagct taatgaatat ttttatgatc caattaatgt aaaatctttt   49200
attttttatt ttttgagaca gagttttgct cttgttgccc aggctggagt gcagtggtat   49260
gatctcagcc cactacaacg tccatcttcc gagctcaagc agttctcctg cctcagcctc   49320
cctagtagct aggattacag gcacccgtca ccatgcccgg ctaattttttg tatttttagt   49380
agagatgggg tttcaccgtg ttggccaggc tggtctcaaa ctcctgacgt caggtggtcc   49440
gcctgcctca gcctcccaaa gtgcaggat cacaggcatg agccactgca cccggcccaa    49500
ttaaaatctt taacactaaa caatctagta catcactggt ggaaacagac atacacctat   49560
tgcaaaggc atctcagctt taaggactca gtcacctcct agcaagatg gaggggaac     49620
tggggagggg tcccatgggg actgtaattc tctctaggtt gtatatttt aaaagacttc    49680
agcagtgtga taaacctggg tggtgtgtac atgggtatta cagtcatgtt gcttaatgac   49740
agggacaggt tgtgagaaat gcatccttag gtgatttcat cattgtgtga aagtcataga   49800
gtacacttaa acccagatgg tagagcctgc tgcacaccgg ggctctgcgg tgcagcctgt   49860
tgctccaagg cacgcaccctg tacagcgtgt tactgtactg aacggcgtag gcccctgtga   49920
cacaatggta agtatttgtg cgtctaaaca taccaaaaca tatagtagaa aaggttacag   49980
caaaaataca gtattatcat cttatgggac catgatacca cagttgaact tatggtctat   50040
tgttgaccaa aatgtcactg tgcagtgtgt gactatacag aaataagctc agagaaatta   50100
agtaacttgg ctgggcgcag tggctcacgc ctgtaatccc aacactttgg gaggctgagg   50160
caggcggatc acctgaggtc aggagttcaa gaccaactga ccaaacacgag aaaaccacca   50220
tctctactaa agaatacaaa acattagctg ggagtggtgg caggtgcctg taatcccagc   50280
tactctactc aggaggctga ggcagggaga attgcttgaa cccaggaggc agaggttgca   50340
gtgagcagag atcatgccac tgtactctag cttgggcgac agggtgagac tccatctcaa   50400
aaaaaagttg gggcgtggtg gctcatgcct gtaatcccag cactttggga ggctgaggcg   50460
ggcggatcac ttgaggtcag gagttaaaga ccagcctggt caacatggtg aaaccccatc   50520
```

-continued

```
tctactgaaa atacaaaaat tagccaagca tggtggtaca cacctgtaat gcctgggcaa   50580
cagagcaaga ttccgtctca aaaaaaaaaa aaaaaaagt aagtaacctg ccacggttca    50640
tacagccaga aagacacaga gccgggcctg accccgcct ctcagcttgc tctagagggc    50700
tattctctgc atgctggcat gatcgcgcct tgtaaaaggt ggcagtgttc tcagcttagt   50760
caatcaggaa ttgcaagagg caagtgagcc cctgaggact ctgggggcc tttgtgaccg    50820
agcagctttg ggagtgaccc tgacagacct ttacaggtgg tgcaagtttt gactcccttt   50880
ctcctggcgc gttaagcaga ggataagcgc tgtggaagga gtgaaggtgt agggagatca   50940
tggcccccag agcagtgggg aaggggacag ggaggctgga ggagagcaag gaaaaggctc   51000
cgtgtcaggt ggcgccttga gtggcctggg taggttgtct tgcagtgaac ccgggttaat   51060
ggccttgaca atgaccgcat tgtttcctga gcactgcagg ctgcccacac acctcacacc   51120
tcggcttgcc taagcccaga gcagccttgt gaggtcgttg ttatgtttat ttaaggaagg   51180
aggaaaggag gcaggtccca ggacatcctg acgtgctgga gatcaccagc ccagaaccca   51240
gctcttaacc ccacaatgtg ggaccttct tcacccatca cagacacacc ccatgctggt    51300
tcaccgtttt cctataatga ctatttgtgc tatttattag aaaaatcttt tccttatgga   51360
tttgaaaaga tttatcttgc tttgtttt ctttttgcc tttctttttt aaggcaggca      51420
ggctcccgca gccccacccc cagggtgaaa aatatagttc attgtctagt aaaagagttc   51480
agagatacac ttttttctt gggtaagata tactctagag cttgttctga aatatggaat    51540
ttgtgtgagc tgcgggagtg ggtgggtgtg tggctctagc tctggaaagt tcttttcctgg  51600
cagtggccag gagggctgcc cagccccctc ctgcctcctc tggcagctta aacacaggac   51660
cccttattct gtgctctctc ctgacccctg gtcctcatgc aggagggaac cctgctcttc   51720
tagggtcctt ttcaaaagt agtgtctttt aggtcattgt caagaactat aatctaaaat    51780
gtatttttaa ctcatctgga aattctgaca gaggtaaggc ttgaaatttt cctgcatact   51840
agccttgtgg tctatataat ccattaaaag ccacatttaa cccaattcca cagactgaac   51900
tgtgcttccc atctaaataa attaaaagca ggccgggcac ggtggtcacg tgtgtaatcc   51960
cagcactttg ggaggtcgag gcgggtggat cacctgaggt caggagttcg agaccaacct   52020
ggcaaacatg gtggaacctc atctctacta aaaatacaaa aaattagctg ggcgtggagg   52080
cgtgcacctc ttaagcttaa ggacatattt cttatgatcc aattaatgta aaatatttta   52140
ttttttattt atttttgag acagagtttc actcttgctg cccaggctgg agtgcagtgg   52200
tgcgatcttg gcctgtaatc ccggctactc aggaggctga ggcaggacag tcgcttgaat   52260
ccaggaggcg gaggttgcag tgagccaaga tcacaccact gcactccagc ctgggcaaca   52320
gagtgagact ctgtctttaa ataaataaat aaataaatag cgagggttca gggcaggaga   52380
aaaagggttc caaatttgtt ctgaaccaat tccaaggaac tttatggcac aaagaaaaaa   52440
aaggggaact tacaaaaagt gaccacactg aagcgtcctg gtcacccatc cctggttttg   52500
accaccagcc tttaaagtgg caagcgggtg ataacccatt tcttatttcc ccctcagcat   52560
ttcctcactg ttattcatac atgtggtcat ttgtactcat ctcacaattg ttaaaacctc   52620
tttcctccct tccaggtttt actgaactgt tactgcgaag tctcagagat gaggtcattt   52680
aagattattt cttatttgta aattagatcg ttcatatttg tacctaatct gatcttttgg   52740
gtaatattcc tagttatgta gactggtctc tcagaagagc cggatattaa atgcagtact   52800
ttaaactta cacccaggag accggatggg tgaggctgga tcactcggcc aaagtaccat    52860
tttatctctg cttttttcttc ccggcttat tgccataatt gacatacaat aaactgcatg   52920
tatttaaagt gtacaatctg ttgggtgtac acacacacgc atctgtgaaa ccatcatcac   52980
actcaaaata gtgatgtaga aattttgctc cttagttcga ctaaatctgg gttcttgtgt   53040
catgaccagg aaaaattagg cacgtggaca cgttgaaggg tagtgtattg agtattgggc   53100
gaaaaggaaa aaagaaaaaa actctcagca aagctagagg ggatcctgcc aatgagttcc   53160
cagctcacag actgattagc aggccaccac acatgagctg gaggcaggc tcctcccgct    53220
gcgcaaggtg agaacttccc gtggctccac cccattctcc caatgccag gtgggtccc     53280
gtccctgcg ggcctgtcca gacaaggga cctgggcag gttccctct ctacacaaaa       53340
gcacctgagg taaacacttg tggggcaggt tgcagattct ctggggacgc cccccttctc   53400
tgcctcctgc atcatcagt agtgcctctg tctgtcaccc ctaaagttta cttgtgctgt    53460
ttctaattcc tctttcccca gccccgtgcc tccctgcctc cctccccag taaaccatga    53520
atccactttc tatcattcta ggttgcttta tatttcctag aattttatat aaatggaatc   53580
atacagcacg tactcttct aggctggctt ctttcactct gcagaatggc tgtgagactc    53640
atctgcattg cagcaagcat caatagttca ttcttcatcc atcatgtgga catagcacag   53700
tttgctgatt cacgcacctg ttgatgagca tttaggttgt ttctagctta tggctattac   53760
aaataaagct gctatgaaca ttcacgtaca agtctctgta caaccctctg ctttcatttc   53820
ttttgaataa ataccctagga gtatgacggc tggaacagat ggcaggtgtt tgtgtaactt   53880
tttaagaaac tgccaaaatc ttttccagca tttcagaaaa atcttagaaa atgctatact   53940
atgttatatt cccactggca gtatatgggg gagttccagt tcctccatac cctcatcaac   54000
atgaggcatg atcagtcttt ttaatttaa ccatgtcagt aggtgtgtga tggtctctca    54060
ctgtggtgat ttttatttgc acttcccctgg tgatttgag catcttttcg tatgcttatt   54120
tgccatatat cttctttggt gatatttctg ttcaaagcct ttgctcattt tttaattgag   54180
ttgcttttct actattcact attgaacact atttatatat tttgaataca aatactttat   54240
cagacatgtg atctacaaat attttcccca gtgtgtggtt tgtcttttctt ttctttctac  54300
tgatagtatc ttaaaaaaaa aaagaaaaa agatttgttttg ttttgttttt tttttttt    54360
gagataggt ctcaatctat tgcccaggct agagtcagt ggtgcgatca tggcttactg     54420
cagccttgac ctcttgggct caggaaaccc tccgacctca gcctcccaag tagctgggac   54480
cacaggtgtg taccaccatg cttggctaat tttttttttt tagatacaga gactcgttat   54540
gttgccaggg gtggtcttga actcctggac tcaagcgacc ctcccacttc ggcctcccaa   54600
agtgctggga ttacaggtgt gagccatcat gcccgaccag ttcttcattt tgatgaagtc   54660
caatttatca atgtccttt tttatggata cttcatttat ttatttattt gagagagggt    54720
ctcaccctga gcccaggctg gagttcagtg gcatgatctc agctcactgc agcctcaacc   54780
tcccaggccc aggtaatcct cctacttcag cctcccaagt agctgagact acaggtacct   54840
gccaccatgc ccgggtaagt ttttttgtatt tatttgtaga gacgggggttt cgccatgttg    54900
ccaggtttgg tctcaaactc ctgggctcaa gtgatctgcc catctcagcc tcccaaagtg   54960
ttgggattac aggcgtgagc caccatgccc agcatatat atatatatat atatatatat    55020
atatatatat ttttttttt tttttttt tttttttg agacagagtc tcactctgtt          55080
gcccaggctg gagtgcagtg gtgcaatctt agctcactgc aacctccttc tctgaggttc    55140
aagtaattct catgcctcag cctctttagt agctgggatt acaggcatgt gctaccaggc   55200
ccggctaatt accagcctta tattttgaa ctctgtttaa aacatttagg tgcataaaca    55260
```

```
ttcaggcttg ttatattctg ttgatgaact gaacctttta ttattatgaa attgctgttg    55320
taatccgtgg taaaattatt tgttctgaac actactttgt ctgttattga tgtagccact    55380
gcagctttct tttgattggt gttaacatgg tatatctttt cccattcttt ttcttttaac    55440
tggtttgtgt ctttatacta tggtttgatt taaatctatt atctcacaat ttgttctctt    55500
tggtacatct ttgttttgtt ccctttcct cttttatgc cttctgttga attaattgag    55560
tctttttgt tttgtttcat ttaatttgt ttttgagac ggagtctctc tctgtctcca    55620
ggctggagtg caatgcgct atctcggctc actgcaacct ctgcctcctg ggttcaagca    55680
attctcctgc ctcatcctcc tgagtagcta ggatcagagg catgcaccac cacgcccggc    55740
taatttgtgt gtgtgtgtgt gtgtgtattt ttactagaga cggggtttca tatgttggtc    55800
aggctggtct caaactcgtg accttgtgat ctgcctgcct tggcctccca aaatgctgga    55860
attataggcg tgagccaccg cacccagcct aattgagtca ttttttaagat tccactttat    55920
ctcctttgtt ggcttattat ttataacacc ttctggtgtt attttagtag ttgctttagg    55980
gtttatagtg tatctctcta atgtctccca gtctaccttc cagtggtatc attctatctt    56040
acagatatta taagaacttt atgacagtat acttcattt ttcccttcat gcatttgtgt    56100
taatgtttca cataatttta tttatttacc tacattataa atattacaat atgttattgt    56160
tttacataga cagccggtta tctttttaag atagtagtaa gaaaaatttt ttacatttac    56220
ccacataatt acctttctta gtgctatata cctttgtata aatccagatt tccatctgct    56280
atcattttcc ttctgcctga aagacttcct gtgatattat ctataatatg gctctactgg    56340
taacgaatta ctagctttg tatgtctgaa aaagtcttca tataaccttc attctagaaa    56400
gtatgtgatt caaagggccg ggcacagtgg ttcacgcctg taatcccagc actttgggag    56460
gccgaggcgg gtggatcacc tgaggtcagg agttcaagac cagcctgacc aataaggtga    56520
aaccctgtct ttactaaaaa tacaaaaatt agctgggcat ggtggctcac gcctatagtc    56580
cctgctactt gggaggctga gacaggagaa ttgcttgaac ccaggaggca gaggttgcag    56640
tgagccaaga tcacgccact gcacaccagc ctgggtgaca gagcaagact ccatccccct    56700
gcaaaaaaaa agaaaagaa aagaaaaaa gtatgtgatt ctacattggc aattttttt    56760
tttttttttt ttttgagaca gagtctcgct ctatcaccca ggctggagtg cggtggtgcc    56820
atcttggctc actgcacgct ccgcctccca ggttcacacc attctcctgc cccagcctcc    56880
caagtagctg agattacagg cacccaccac cacacccggc taattttttt gtatttttta    56940
gtagagatgg ggtttcacca tgttagccag gatggtctca atctcctgac ctcatgatcc    57000
gcccacctcg gcctcccaaa gtgctgggat tacaggcatg agccaccgg cctggccact    57060
tttttcttt aaatgctttt aagatgttcc tactatcttc ttgttttaa ttaattaatt    57120
tattattatt attattatta ttattattat tattttttt ttttttttt ttttagaga    57180
cagggtcttg cgctgatgcc gaggctggag tgtgctagtg ccatcgtagc tcactgcagt    57240
ctcaaacacc tggtctcaag caatcgtcct gcctcagcct cctgaggaac taggactaga    57300
ggtatatact accatgccca gccaatttta aaaattttt gtagaggtgg agactcgcta    57360
tgttgaccag gctcctctcg aactcctggc ctcaagcaat cctcctacct ctgcctcccg    57420
aagtgttggg attacaggga ttacaagtgt gagccactgt gccagtcccc actgtcttct    57480
ggcttgcatc gtttctaaaa gaaacttggt gtcatcctta tttttgttc tctacatgtt    57540
atatgtcctc tttatctggt tgctttaact ttatttatta atttttagtt aattttaat    57600
tgacaaataa taattgtatt tttatggggc acaatgtgat gttttggtct atgtttacat    57660
tgtggaatgt gtaaatcaag ctagtgaaca tatccaccac ctcacacact taccattttt    57720
tgtgtgtggt gagaacatgt aaaggctgct ccttgaggcc aggcccaatc ccagcacttt    57780
gggaggccga ggcgagtgga tcacttgagg tcaggagttc aagactagcc tggccaacat    57840
ggtgaaaccc cgtccctact aaaaacacaa aaatcagcca ggcgcggtgg tacacgccta    57900
tagtcctagc tacttgggag gctgaggcag gagaatcact tgaacccaag aggcagaggc    57960
tgcagtgagc caagatcatg ctactgcact ccagcctggg caacagagca agactccatc    58020
tcaaaaaaaa aaaaaaaaag tctattcctt gagcaatttt gaaatacaca atacatcatt    58080
gttaattatg gtcaccatag tgggtagtag atcactaaat cttattcttc ctgtctaact    58140
aaaacttttt tccttttgac caacatctcc ccattccctc cctcaacctc agcccctgat    58200
aaccaccatt ccactctcta ctgctatgag tttgacctt ttagatttca catatgagat    58260
cacatggtat ttgtcttct gtgcctggct tcttttactt agcataatac cttccagatt    58320
tacccatgtt gttgcaaatg gaatttcctt cttttttaag gctgaatagt attcgtgtgt    58380
gtgtgtgtgt gcgtgtgtgt gtgtgtgtgt atcacatttt ctttatctct tcgttcatta    58440
atgatcattt aggatgattc cacatcaggc tactgtgtat agtgctgcag taaacatgga    58500
agtgtagaca tctcttcagc atactgcttc caatctctta ggatatataaac ccagaagttg    58560
gattgctgga tcatatgtag tgctatttt gtttttttga ggaacctcca tacttatttt    58620
gcataatgct attctaattc acaatactac caacagtgga catgggttct ttttttctcta    58680
catgcttgcc aaccacttgt tatcttttat ctttttatat atctggctgc ttctaaattt    58740
ttttcttct taccaattct gaaccatttg atggtttctt cctttatgct ccttgtgctt    58800
gaggttcatt gagcatctgg gatcagtgca cttattgttt tcatcaaatt cagaagatta    58860
ggccattatt tcttcaaact ttttttgtcgt tctctgtcta cctttgagag ctccaattat    58920
acatacatta ggccacttga agttgtcatt acagttcact aatgctaagt tcttttta    58980
agtcttgttt ctgtgtttca ttttggacac tttctattgc tacatcttca aatttactaa    59040
ttttttcttc tgcaatatct aatcctatc cagtgtattt tccatattag    59100
atattgtagt tttcataact agaagcatga tttggttctg ttttcaccca tgtatctata    59160
taacatgtcc agtctttcac tcagcttctt aaacatttag aatatggtca gaataacttt    59220
ttttgctgtt ttgtttaga dacagggtct cactttgtta ctcaggctgg agcgcagtgg    59280
catgatcaca agctcactgca gccccaacct cctcgtctca aggaatcctc ccacctcagc    59340
ctcctatgta gctgggacca caggtacaca ccaccacacc tggctaattt ttaaattttt    59400
tgaagagacg ggtctcactt tgttgccccag actggtctca aactcctggg ttcaaacaat    59460
cctcagcct tggcctccca acgtgttggg attacaggca tgagccactg tacccagccc    59520
agaataactt tttaaaaatg tcttgaggcc gaggttggga aataatctga ggtcgggagt    59580
tcgagaccag cctgaccaac atggagaaac cccgtctcta caaaaatac aaaattagcc    59640
aggcacagtg gcacatgcct gtaatcccag ctactgggag gctgaggca ggagaattgc    59700
ttgaacccgg gaggcagagg ttgtggtgag ccgagatcac accattggac tccagcctgg    59760
gcaacaagag cgaaactcca tctcaaaaaa aaaaaaaaa aaaactctta gccacaattt    59820
ctatcatctg tgtcacttct gagtccttt ctattcagtt attttctcc ttgtcatggg    59880
tcatattttt ctgattcttc atgtgtcctg taattttctt ttcttttttt tttggagat    59940
ggagtcttac tctctcaccc aggctgtagt gcgatggcac aatcttggct cactgcaacc    60000
```

```
tccacctcct gggttcaagt gattctcctg cctcagcctc ccaggtagct gggattacag   60060
gtgctcacca ccatgcccag ataatttttt gtatttttag cagagacggg gtttcaccat   60120
gatggccaag ctggttttga actcttgacc tcaagtgatc cgcccacctc ggcctcccaa   60180
agtgctagga ttacaggcat gagccaccgt gcctggccag ttgttctcat tggatgtcat   60240
atgttgggaa cttttattgg tgatggatat ttttgatttc ctataaatat tcttgaactt   60300
tgttctggga tgcaattaag ttacttggaa aatctttgat cctttcaggt cctgtttctc   60360
agcttcatta gatgggacta tcacagtgtt tgtttagag ataactttgc cccactgctg    60420
aggcaaaacc actttgagct tcacctgatg ccccatgact tcagtgatct tccactgtgg   60480
gaggcgagag caggactata tccagctcca tgtgggcccc aggcagcgtt cactatcatc   60540
atttcaggtt gctactgaag tatccctttt tcaggctctc agctggcaga gcaaatacat   60600
atatgtatac atactaacct atgtctatac aggaatctat cggtatttct gtctgtggcc   60660
atctgtagct gtatgaagcc aaacatgagt gtgtgctgat gtctccagcc ctcatctgtt   60720
accagatgga tcgttctagc ctcctccact tgccctacctg tcaattcacc attccttgag  60780
ttcatggttc atttttcagta tacctgcaca gtggtatcag aactgttaac ccacacccg   60840
tgggaaaaaa actccatcag ctagagcaca gtgtttacag ccagatcctt ttgcctttag   60900
tcttacagat tccaatcatt ccaaattatt cggtgcagcg cctttccgca cctgcaccca   60960
cttttttccc tgagattgtt tcctacattc gtagcacagt tagattgttt tgttacattc   61020
tgcatttcac cctgggatcc tccaacctcc taagttattt ttgttttatt tgcacacatt   61080
aggttcaatc tgaactataa agttctgtgg gttttcacaa atgcgtagtg tcatgtatcc   61140
accactacat tttccttctc tctctttctt gctttctcgc cttcttgtct tgctctgtca   61200
cccaggctgg agtgcagtgg cacaatctcg gctcactaca acctccgtct cctgggttca   61260
agcattctg ctgcctcagc ttcccgagta gctgggacta caggcacgca ccaccaccc    61320
tggctaactt tttgtatttt tacaaaatac aaaagacgat gtttcactat gtgggccagg   61380
ctggtctcga actcctgacc ttgtgatcca cctacctcgg cctcccaaag tgtgggatt    61440
acaggcgtga gccaccacac ccggtctctc tccttccttt cctttcctct cctttccttt   61500
tctttcttc tcttccctc tcctctcttc tcctctcctc tcctttgatg gaggtctcac    61560
tgtgacaccc aggctggagt acagtggcag cataatctca gctcactgta gcctcagcct   61620
cccagggctc aggtgatcct cccacctcag cctcccaagt agctgggatt acaggtgcac   61680
accgctgagc cagcaaatt tttgtatttt ttgtaaagat agggtttcac catgttgccc    61740
aggctggtct caaactcctg agctcaagtt atctgccagc ctcggcctcc caagtgctg    61800
ggatgacagg catgagctac cgtgcccaga ccactgttag atttcatat gaatagtttc    61860
accacatcaa aaaccccat gctcaccta ttcaaccctg cctctcccac cccagccag     61920
ctcagaaatg gttcttttta ccattgctat aatttttgcct tttccagaac gccatgaatt   61980
tgaaatcata tagtatgtag ccttttcaga ctgacttctt tcatagcaat atgcatttaa   62040
gagtcatcca tgtctttcca tggcttgata tctcatttct tttacactg aatgagttcc    62100
cactgtctgt ttgtaccaca gtttgtatat ctattcacct atctaagggc atcttggttg   62160
cttccaattt ttggcaatta ataaagctgg ccatgcacag tggctcacac ctgtaatccc   62220
agcattttgg gaggccaagg cgggcagatc acttgaggtc aggagtttga gaccagcctg   62280
gccaacatgg tgaaacgctg tctctactaa aaatacaaaa attagccggg cgtggtaatg   62340
ggcacctgta atcccagcta cttggaaggc tgaggcagga gaatcacttg aacctggagg   62400
cagaggttgc agtgagctga gatcgtgcca ctccactcca gcctgggtga cagagtgaga   62460
ctctgtccca aaaagaaaaa gaataaactg ctgtatacat gtgtaggttt tgtgtggaca   62520
gaagttttca aatcagttgg acaaatacct aagagtgtga ttccatcata cagtaaaact   62580
gctttgcttt gtcagaaact gccagaatgt cctccaaggg ggctgtctca tgttgcattc   62640
ccaccagcaa tgaatggggg ttcctgttgc tccacatcct caccagattt gatgatgtca   62700
gttttgtgga ttttagtcat cctagtaggt gtgtggtgac accacattgt tgttctcatt   62760
ctcagtgccc cgatgacata tcatgctgag cattgtttca tatgcttact tgccatctgt   62820
atatcgtcct tgctgaagtg actgttcaga tgttcagatc ttttgcccat tttctttctt   62880
tttttttttt tttttccttt tgatacgag tcttgctctg tcgccaggct ggagtgcagt    62940
ggcacaatct cagctcacta caaccttgc ctccgggtc caagcgattc ccctgcctca     63000
gcctcccaag tagctgggac tacaggcacg caccaccatg ccaagctaac ttttttcttt   63060
ttttttcttt tctttttttt ttgagatgaa gtctcgctct gtcacccagg ctggagtgca   63120
ttggtgcgat cttggctcac tgcaagctcc gcctcctggg ttcacgccat tctcctgcct   63180
cagcctcccg agtagctggg actacaggcg ccccaccac gccggctaa ttttttttgtg    63240
tttttagtag agacggagtt tcaccgtgtt agccaggatg gtcttgatct cctgacctcg   63300
tgatccgctt gctccggcct cccaaagtgc tgggattaca ggcgtgagcc accgcctta    63360
gcccccattt ttcaattgag ttgtttgttt taagacctct ttgtatatta ccacatgtgt   63420
attgaaaata ttttctccca gtctgtggct tgtcttaat ttcttagca atgtcttttg     63480
cagagcagaa ggtttcatta gctttcatag attccaactt atattttctc tttcatggat   63540
tgtgcatttg gtgttgccca cacagatttt tatactgtat tctggtgcca tttactgagt   63600
taacaattgc ggaagaactg gaagaaagga agcaaacaaa acgagttctg cgtggcactg   63660
tcagtgcggg ggcatgggga gtcctgcagg gtgaggtatg ggcggtatgg caaggcgcgg   63720
gcccatagat gtgcaggtct ggagatgtgt gcagcggaga tgtgcgggcc cgagatgtgc   63780
gggtccgatg tgtgggtccg gagatgtgcg cgtacccaga ggcagatc ggaaatgtg     63840
gggtccggag gaaatgtgcg gatcaggaga agtgccagtc ccgagatgtg cggatcggag   63900
atgtggaggg ctaggagatg cgtggtccg gagatgcgca gatcaggaga tgggcgaatc    63960
ggagatgcgc gggtccggaa atgtgcagag cggagatgtg tggatcagga gatgttgggg   64020
ggtcaggaga tgcgggggtc cagagatgtg ggggtccgga gatgtcgggt ctggagatg    64080
tgcagacag agcaaagatg agctgatcgg agatgccgag gtccggggat ccacgggtcc   64140
ggagacgcgc gggtccggag atgcgtgggc ccagagatgt gcgggtccaa agatgtgcaa   64200
atctgaagat gtgtggatgg gagatgtgca ggtccggaga tgcgcgggc ggagatgtgt    64260
ggatcggaga tgctcagatc gaagatgtgg gaatgaggag atgtgcgggg cgggatgtgt   64320
ggatgggaga cgcgcgggcc cggagatatg cggggcggag atgtgcgggt ccaggatgt    64380
gtgatctgag gtgtgtgggt ccggagctcg tgctcagctc agcagcagtg agagcgagca   64440
tgctggcttt gggagcacag cacaatggca gctgtaggag tgcaagaggg tgtgacccag   64500
aggcagggcc cggccccgca tgggtgttct gaggtttatg cctcagcact agaagcctcg   64560
tatgcgaaat cacatcctca tagacccggt tcagacacag gatagtgatg cctggactat   64620
tcatccgtct ctcctctttt tccccagaca cgctttcacc agcttcgagc ccctcctcgg   64680
tgacttatcc tgtggtcccc ggcagcgtgg acgagtctcc cagtggagca ttgaacatcg   64740
```

```
aatgtagaat ctgcggggac aaggcctcag gctatcatta cggagtccac gcgtgtgaag   64800
gctgcaaggt agaggggagc tggaacaggg cctggtggcc gccaccatca actacttatg   64860
gtcactttta tagcaaatgg cagtcattac tgagagattg cagaaagtcc cggataagaa   64920
actgacttca ggccaggcgc ggtatctcat gcctataatt ccagcacttt gggagaccga   64980
gatgggtgga tcacctgaga tcaggagttc gataccagcc tggccaacat gatgaaaccc   65040
tgtctctact aaaaatacca aaaaaaatta gccaggcgtg gtggtgggcg cctgtaagcc   65100
cagctactcg agaggcaaag acaggagaat tgcttgaacc caggagccag aggttgcagt   65160
gagccaagat tgcgccactg cactccagcc tgggcaacaa gagtgagact ccatcttaaa   65220
aaaaaagaaa gaaaaaaaga aaaagaaaaa gaaactgacc tcagtgatag attagcctct   65280
ctttatagca cagaacccct gagagcgtaa gccctgttgt gaactgcgta tttgaggaat   65340
ctagcttgta cgccccttat gagaatctaa tacttgatgt tccaaggtgg aacactttca   65400
tcctgaaact atccctcccc acccccatct gtggaaaaat tgtcttccat gaaaccggtc   65460
cctggtggca aaaaggttgg ggattgctgc tttagagagt ctaggacaaa tggttcctct   65520
gtgctttgta aatacttaga gaagtgcatt ctttaaaaga aaataagtca cattggaccg   65580
ggtgcagtgg ctcacgccta taatctcagc actttgggag gccgaggcgg ctggatcacc   65640
tgaggtcagg agttcaagac cagcctggcc aacatggtga aaccctgtct ctactaaaaa   65700
tacaaaaatt agccaggtgt ggtggtgggt gcctgtaatc ccagctactt gggaggctga   65760
agcaggagaa ttgcttgaac tcaggaggcg gaggttgcag tgagctgaga tcgagccatt   65820
tcactccagc ctaggcgaca agagtaaaac ttcatctcaa aaaaaaaaaa aagagagaaa   65880
agaaaataag ccacattaag aacatcactt cattcgaata caagacagag agctgttacc   65940
gttgatctct ggagcctccc tgaaggccag gtggggcagg tgttctcatg ctcctgccag   66000
ggaaattggc catcagagac acagaatatc ttgcttaagg tcccacagcc ccagcagca   66060
gggactggaa ccagagactg gctgctcctg ctccccagca gttccttcct gcacatcagg   66120
ggcttctcca cctgattcaa gcgacaggaa cccctgtgc atcttcatcc tcctgctggc   66180
tcagcctgcc ctaaacagat gtgacctggg ccaggagtgc atgaaggcag gccctgttgt   66240
cctgcatgct gccagtctga ctggtggccc ttccgtgttt gtcagcgtgg tgatgaggag   66300
agctcctgta gcagcgtccc tttagggttg cacagacgtg ctcaagtctg gcgccttatg   66360
tacgtgatat gtgggagatc atcatctgaa tgtttggttt gaatcagaaa tcccttctca   66420
cggtgcacgc tgcaggtgtt cactaacttg gaaaatgcca ccgcctttct ggcacaatgt   66480
accatcttgg aacaccagca ttctgccctg agccaggcct ggcctcagag gcctgggcca   66540
cagggagaac ctcacagcca ggacactgtg gcactctgct gtctagaagc ctgtctcccc   66600
acccttccca ttctaacccc atgcgttcct cagcctcccc actgtgcaag cctaggtaag   66660
gacattatga agacgtcagc ctgcctctca cattccctg cacactgctg tccctctccc   66720
gcgggccaag cagacccact gtggcaaaaa tatagaagaa tgacttaaaa gcaaagagaa   66780
aaaagaaccc aaagcaaaaa tgaactcctt cgcatgtttt ctaaccatat accttgaaa   66840
aagctcctta taaagtggcc ttttccttag ggccatgatt aattattcat ttagttttgt   66900
tttttatgga ctatttagta acattgtttc ttgctgggta gagtttaaga tgcttttaca   66960
aagcaagaaa attgtttaca aacagctggc ttcctttttat tataattttt gtctttgagg   67020
gagttaatat actcttacaa aaattcttag aaagtgtcac gtcacaaata tggaaatgtc   67080
acaatgctgg ggatagttac attcatatac attgtaacaa ggctgagtaa ctctttggaa   67140
aactataatt gtgttttccc aagtcagatg agggcatttt gaaatgactt cgaatgctgc   67200
ctcattttat tgttttttcac attaaatgta acgcacttta aagttctgta tttgtcctaa   67260
tcattccaga cttcttagaa gaactatttc tttctttttt ttttttttt tttttttttt   67320
tttgagatgg agtctcactc tgtcgcgcag gctggagtgc agtggcacaa tctcagctca   67380
ctgcaacctc cgcctcctgg gttcaagtga ttgtcctacc tcagcctcct gagtagctgg   67440
gactacagac ttacatcacc atgcccggct aatttttgta ttttагtag acagggtt     67500
gcaccatgtt ggctaggctg gtctcgaact cctgaccitca ggtgatccac ccgcctcagc   67560
ctcctaaagt gctgggatta caggcatgat caccatgcct ggcctggaat aacttttctc   67620
taaattttgt tcatttaaaa agaaacaata aatgagcaac aaaaaaggtg agtaaagcaa   67680
gtgcgctggt ttctcagtgg cccaggtctt taaatccact gtgtattacc ctcacagggc   67740
ttctttcggc gaacgattcg actcaagctg gtgtatgaca agtcgacag cagctgcaa    67800
atccagaaaa agaacagaaa caaatgccaa tattgtcgat ttcacaagtg cctttctgtc   67860
gggatgtcac acaacggtag gtaaggtggc cctgcacatt ttcccagttc gttcctcagt   67920
tccccttcct tgctccaagg gaacagatca agctatggat gaatgtgctt caacatttca   67980
cacccaagtc attttgtaat cagagtggcc taagaaaata aagtcgccc aggcgcggtg    68040
gttcacgcct gtaatcccag cactttggga ggctgaggtg ggtggatcac ctcaggtcag   68100
gagtttgaga ccagcctggc caatatggtg aaaccccgtc tctactaaga atgcaaaat    68160
tagctgggtg tggtggcaca tgcctgtagt cccagctact cgggaggctg aggcagaaga   68220
atcgcttgaa cccgggaggc ggaggttgca gtgagccgag attgcgccac tgcactccag   68280
cctgggcgac agagggagat tccgtctcac aaaaaaaaaa aaaagaaaaa gaaagaaaga   68340
aagaaaataa aagtctccca ggtgcggtgg ttcacacctg taatcccagc actttggagg   68400
ccgaggcggg tggatcactt gaggtcagga gtttgagacc agcctggcga catggcaaa    68460
accccgtctc taataaaaat acaaaaatta gctgggcatg gtagtgcaca cctgtaatcc   68520
cagctacttg ggaggatgag acaggagaat agcttgaacc cgggaggcgg aggttgcagt   68580
gagctgagat cgcaccactg cactccagcc tgggcgacag agtgcgactc cgtctcaaaa   68640
aaaaagaaaa aaaaagaaaa agtctcaaat agctgagatt cagtcggtgca ttggactcgc   68700
tgttagaaac ttcagtggta agactttgat acagaatcga aaaccaagt ggaaggcacc    68760
aaaatgacag aatgttcacc tcgtccatag gaagggtgta ccacctcaaa catctcacca   68820
cgttatgaat ttccttctag ccaatcatttt aatagtttca gaacatgcta attgtgatgt   68880
gaatgtaagt cgttcataag agttgcatgt ctacctctgt gaaaagaag cagttattat    68940
ataaactcat cccgaagccc cgttcacctc cttcactcaa aggttgatga tgcacctgat   69000
agtggtgtgc accctactaa tgagacgaac gatggtgtca ccttcagcct gcacctgtta   69060
acgatggtgt caccttcagc ctgcacctgt ttaaacatct acagtgtatg gagtttgagt   69120
ttttcatctc tccatagtgg aaagcgaat agtaatgaag atgtggtctg aactgcctgt     69180
gaattttcat tcctggttta aagtcctggg ggagccctc gtccagccct gtccgcgcag   69240
tcatgacctc actgctcatg cctgtgtttc ccctccaaa cctagcgat tcgtttttgga    69300
cgaatgccaa gatctgagaa agcaaaactg aaagcagaaa ttcttacctg tgaacatgac   69360
atagaagatt ctgaaactgc agatctcaaa tctctgccaa agagaatcta cgaggcctac   69420
ttgaagaact tcaacatgaa caaggtcaaa gcccgggtca tcctctcagg aaaggccagt   69480
```

```
aacaatccag taggtgtttg cggctgttct gggttctctt ggcaacatgg aaccagtgtc   69540
gtagaggacg attaaggaca catgtgttga atgttgagaa aatttatattt atcccacagt   69600
taagcaaagg acagcgaaga tggaaacagt tcattctgag actctgagct gtagcttaac   69660
aacaactcct ttcttcttgc ttggagccac ctcaaagctc ttagcaacta agttattata   69720
ctggctatgt aattaataca cttaaaaaaa accttaatag cttaccaagt actaagatga   69780
tttcttagga gcatttttc ttaaatagag ataggttctt gctctgttgc ccaggctgga   69840
atgcagtggt gcaatcatag ttcactgcag ccttgaactc ctgggctcaa gcaatcctcc   69900
tgcctcagcc tcccaaggag ctgggactac aggtgtgcac caccacacct ggctatgttt   69960
gatgttgttg ttgttttgtt ttgttttttgt ttttttggtag agatgagatg tttcccaggc   70020
tggtctcaaa ctcctggcct caagtgatct tcccacctcg gcctcccaaa gcactggcat   70080
tacaggtgtg agtcatggca cccagcatta actggattta aaaaaaaaaa aactgaccag   70140
gcaagatggg tcatgcctgt aatcctggca ctctggggag gccaaggtgg gcagattgct   70200
tgagtccagg agtttgatac cagcctggcc aacatggaga aacccaact ctactaaaga    70260
tacaaaaatt agctgagcag ggtggcacac acctgtaatt ccagctactt gggtggctta    70320
ggcatgagaa ttgcttcaac ccgggaggca gaggttacag caagctgaga tcatgccact    70380
gcactccagc ctgggtgaca gatcgagacc ctatctcaaa aaaaaaatag aataataaaa    70440
taaatcccta ctttgaggtg tattagtctg ctataaagaa atccctgaga cctggtaatt    70500
tataaagaaa agaggtttaa ttggctcgtg gcccacaagg ctgtacagga agcttctgct    70560
tctggggagg cctcagggaa tttgactcat agcagaaggt gaagtgggag taggcgtctt    70620
gcatggcagg agcaaaaaca agagacacac acttttcacc catcagatct tgtgagaacg    70680
ctatcactag agtagcacca agaggatggt gctaaaccat tcatgaagga tcaccccat     70740
gatccagtcc ctcccgccag gcctcacctc caccactggg gattacagtt caccatgaga   70800
tttgggtggg gacacagagc caaaccatat cataaggcta gaaaaggaaa ccacttactt   70860
cccactcaaa atgtgctctt ggtcctttct cctaaaacta ctccctccct ctcagacaaa   70920
catgcctaca ttcttttttcc gccttcagtg aaaagacagt gacatcttgg ggcttagaaa   70980
gggccacttg taagccaggc gtggtggctc acgcctgtca tcccagcact ttgggaggcc   71040
aagacaggcg gatcacgagg tcaggagatc aagaccatcc tggctaacat ggtgaaacac   71100
catctccact aaaaatacaa aaaattagcc gggcgtggtg gcgggcgcct gtagtctcag   71160
ctacttggga agctgaggca ggagaatggc gtgaacccag gaggcagagc ttgcagtgag   71220
ccgagatcgt gccactgcac ttccagcctg ggcgacaagg ccagctgtgt ctgggcgcgg   71280
tggctcatgt ctgtaatccc agcactttgg gaggctgagg tgggtggatc acttgaggtc   71340
aggagtttga gaccaccctg gccaacatgg tgaaacccca tctctattaa aaatacaaaa   71400
aattagctgg gcatggtagc ggttgcctgt aatcccagct acttgggagg ctgaggcagg   71460
agaattgctt gaacctggga gctggaggtt gcagtgagct gagatcgcac cactgcactc   71520
cagcttgggc aacagagtga gactctgtct caaaaaaaaa aagaaggaa aagaaggac     71580
cacttgttat agaaagcctg tcttttaagg tagctctgga cctttcaga ggcagccaaa     71640
ttgccctcta tggttcgtcc cccacatccc cgcctgcctg gctaagtcc tccttccccc     71700
tccccaacag ttaaataagt ctttgtctcc attacaaaac aaatctcaga gctaccttca   71760
aagaagagcc agccctcagt tggtgaatga agatactttg acattttcct atgagcatgg   71820
tgaaacaggt ttaatttgta ttaaatagct tgaagcaatc cttattggga attcaaggt    71880
ggaattttag tcacaggaaa ataaagcatt tcacaagcta cttactttca tgaacaaacc   71940
aaacctcttc tttactgagt cctttaattc ttcagtgaat tctccaatta aataggccga   72000
gacattttag aagtttccag cagacaccca cactaggcag ctccagaggc ttgtcccaat   72060
tagaactttc ctggattacg agagtgaaag aaaaaggtaac ttttagcttc gagtctctat   72120
cctggatatg attagtacag cccaaaattg ggatggctaa aacttttgtt tgccagctta   72180
tatttctccc ttggatttca gaattgaaag caggctgggc acagtggctc acactgtaat   72240
cccagcactt tggggaggctg aggcgggagg atcacttgag gcaatccaag agtttgagac   72300
caggcaacac aaggagacct cgtctctaca aaaaatgatt tttttaaaaa ctagctgggc   72360
atggtggcat gtgcctgtgg tcccaggtac ttgggaagct gagatgggag gatggcttga   72420
gcccaggagt tcaaaaccaa cctgggcaac atggcaagac cacatctcta caaaaaataa   72480
aaacattatc caggcatggt ggcacatgcc tatagtcccc gcgacttggg aggttgagga   72540
ggatgccttg aggccaggag ttcaaggctg cagcgagcca cgatcgcgcc actgcactcc   72600
agcctaggcg acaaagcgag actctctaaa aaaaattcga agcagagtta agttgtcttt   72660
cttcctaaca acctgccccc accatggggt gcgaatggga ctcctggagt cctcctgcac   72720
ctcccctttgg agaccaccaa gctctaggaa ccccatcacc ctcagctgag ggtcacatgc   72780
agcaactagc aggcgggaat ctgtttgcat tttggcctta agaaaataaa taataggcca   72840
ggcgcggtgg ctcatgcctg taatcccagc actttgggag gctgaggcag gtggatcac    72900
tgaggtcagg agttggagac cagcctgacc aatatggtga aacccgtct ctactaaaaa    72960
tacaaaaatt agctaggcat ggtcgtgggc acctgtaatc ccaactaccc aggaggctga   73020
ggcaggagaa ttgcttgaac ctggaaggca gaggttgcag tgagccgaga tcacaccact   73080
gcactccagc ctgggtgaca gagcgagact ccatctcaaa aaaaaaaaa aaagagggcc    73140
aggcgtggtt gctcatgctt atgcctgtaa tcccagcact gtgggaggca gaggagggcg   73200
gattacctga gctcaggagt tcgagaccag cctgggcaac atggtaaaac cccatctcta   73260
ctaaaataca aaaaattagc cgggcatggc agtgcgcac agtgtccca tcctattcggg    73320
aggctgaggc aggagaatgg cgtgaacctg ggaggtggag gttgcaggga gccgagatca   73380
caccggtgca ctccagcctg ggtgacagag tgagactcca tctcaaaaaa aaaaaaaaag   73440
aaagaaatga tagatgaata gtttaggatt ggggttcaca atttggtttt ctgtagaaaa   73500
agagaaccgg gcactcttcc gagagtcaga tgccctcttc cacccacacc cacaaagcca   73560
gagcaccgca ggtaccagtt ttcaaggcaa cctccaacca tcatgtgact cttgtgttt    73620
gatcacactg tttgctccaa gccagggttg cgtccacccc catgtccttg tctgcgcacg   73680
ggacgctgga ggcacggccc cctcctccct gcctagcctg ctgacgggct ttccagagct   73740
ggctccttca ggtgcaggat accctctctg cttagtctgg gaaaaggccc cgttggcagg   73800
atgcccacca ccaggccaca ctgcctgaat ctattggcag agctctggtt ttgtggcaa    73860
ggtgggtagt ggaagaccat agcctgtgtc ccttacacat ctcagaaagc aacccccatct   73920
gtgggcaagc aatctgttag ggagaccaag cagcggcctg gaaacacctt gatctctgcc   73980
cagtggccca catgcggtcg ccgtttcatc agtttccagc ctgggtgacc tcacagcccc   74040
agccacgccc cacagagcct caggaaggca cactgacctc agggcggcg gctgacttca   74100
tttctgttt gggatgagag gcggcacagt aaactgtcca ggccagtaaa ctaatggatt   74160
catacgaacc gtaatgaacg tgggctgtgt gctggggaag gcaggctcgc ctcctccctg   74220
```

```
caggggctgc tgggggtgaaa gcaaccctga aatgttcaaa gccttgatgg ggaagcacgg    74280
gggatggata gattttaatt tcaaagcagc cctctggttt gctataagcg ggggactgaa    74340
tttctctttg cagtggccaa tgcctttctt ctgtcaagat cagctcgtgg ccttcagatc    74400
agatgacgca aagcccatg  gctgagctgg aacaggctag aatgctgggg gggggcctga    74460
aaccggtggg ggagttgtgg gaggcctaga atcagccagg aggcttgggt cggggttgga    74520
accggccagg gtgcacggag gaggctgtgg gggcagggggg aggccgctgc atggagccgc    74580
atagatgcca ttgcttgagg aaaggtgggc tttagctgag ggaaggagtg aggggtggat    74640
ggagaatgtc tgtgtccatc tggacactgg gactgtttga gccctgaga  tttcagaacc    74700
gtgggccaga aaatggtcag ggcccttggt gatggggaag ggcgccctg  gggaactcac    74760
tgccccttga tttgagggta acagggatgg aagcagagtc aggggggctga gggaggcaat    74820
aaaaatgggt gcttttcaac agtgtctaaa aacataagat gttgacctgt caggggttga    74880
gaatgtcgtc agaagacttt ggaggaagca acagaaaatg agactgaggg gcttgggcag    74940
agtcagtgcc ttctgtgtga tgcacgctca tgcacaaatg cacgcacata cccacactca    75000
cacatccgtg cacacacggg tacacacaca tacacgtgca catgcacata tgctcacaca    75060
catgcaccca cagtcacaca tccatgcatg catgtgtaca caaacacacc cacacataca    75120
catgcaccca cacgtgtaca cagatgcacc tccaccccca tacatgcaca tggacacaca    75180
catgcaccca cacgcacaca agcatccatg ctcacatggg tacacactca cacatccatg    75240
catgcacgtg taaacacaca caccccccaca catacacgtg caccacaca tgcacacaga    75300
cgcacctcca cccccacaca cgcacacaca cacatgcacc cacacatgga tacacgcaca    75360
ctcacacatg tacccacacc tgtgtgtaca cacacatg   catgctcaca cacatgcacc    75420
caggcacaca caaatccaca ttcacccata cagtcacaca catgcataca cacacataca    75480
aacacatgca ttcacacaga tgcatacaca cacacactta caaactacac atgtgcttat    75540
acatgctcac atgcatgtat atgcacacac atacccctcac cttatgcaca catgtaccca    75600
cacacgtacc cacacatata caagcatgca cacatatata tatatacaca tgctcacacg    75660
catcccaca  ctcacatgtg tgcacatatg ctcacacaca cgtgcacaca catgctcaca    75720
cacacactta ctgttgctca ggcttagctg ctttgggctt aagaagcaaa ctgcaccttc    75780
caaaaaatga gtgtggtgtt cagttaaaca accaaataat tctttagcac tgaatatgtg    75840
gactttagaa attcaaacta taaggtgata ataacgttgt cctgctactt tttaatctaa    75900
caaacatatc agaactgaca ctcagttcaa atgaagaaag taggaattgg gcgtgccgtg    75960
ttatttttttc aaagattctc ctattgctcc aaattgttgg ggattatctt aaagtcttttg    76020
aatagcttca gttatggaag atttttaccct ctgagaataa aactgaattt tagacaaacc    76080
atgagtccat tgtagctaga ctggcatgca agttgggatt aaacagagta aaacgtcttg    76140
tttaaaaaaa taagaaaggc cggcttgggc aacatagtga gacctcctct atgaaaagtt    76200
agctgggcat ggtggtgtgc gcctgtggtt ccagccgctc aggaggccga ggcaggagga    76260
tggaggtcaa gactgcagtg gactgtggtt gcgccactgt actccagcct ggtgacaca    76320
gcaagacccc gtctcaaaaa aagaaaacag aaaaaagaaa aaaaagttg  agcaaggaga    76380
ctaatttgtg acatgcagct gaacatggtt tttaagacca gttttgaaag aggaattcca    76440
acattattct taacatttca gaagcctggg cataaggggtg acctccaggg tgccgtgtta    76500
taacaggact gctcctttca acagctatga ccttataca  tgtcttgggg tgttgcctgc    76560
cgtgtgacag tccaatatta tacctactac ttaagttttc tttagattaa aaaatgtgct    76620
tcatattta  tgccatttct acaaatgtat agtaaaacat aaccaagaga gcttattaaa    76680
taatttcatc caaagcagtt ctaccagtgc ttcacattta tttttattt  atttatttat    76740
ttttgagact gagtctcact ctcttgccca ggctggagtg cagtggcgca atctcagctc    76800
actgcaacct cccctcctg  ggttcaagcg attctcctgc ctcagcctcc taagtagctg    76860
ggattacagg tgccagccac cacacccgac taattttttgt attttttagta gacacgggct    76920
tttgccatgt tggccgggct ggtctcgaaa tcctgacctc aggtcatcca cctaccttgg    76980
cctcccaaag tgctgccatt gcgggcatga gctactgccg ctggtccaca tttaatttttt    77040
tgcaaaaaga tgacagctgc taacagagat gaattctcat gagtgatatc attgagcttc    77100
gtaggccaca tgagtgtgtg ccgggaccag tgtggcagca agcggggcgt tctgctctcg    77160
gcatggagtg attgggaaa  atctaggcag cttcctgcct cacgctgttt aaaaccttta    77220
taatgtgctt tatttcattt attttgaaatg actgcctgtc gtgtcagata tattcatagt    77280
caagcttgag tataaaaggc atattccaaa gttaaatata agctgctgca tagattttttt    77340
tgtaaaatga tctcaccaag aatgtttatc cataaagttt agcgaatttg caagtgtgtt    77400
tttcaacagc atttctcttt agctttaata aacattggtt tcttcatggt accactcatt    77460
ttgaattcag tggtctccag ttctccctgc taaatgaggc ccacttttct aaaccaaagt    77520
gataattta  taaaaatgaa atgagatatt tgttaccaca gaagtcctca tttacgagag    77580
tacatcccca tagaactagt ccacggtgag cctcaggggc atgcaagctg tttaacgatg    77640
ccccccagcct agaaaggccc aggcttgggt gttcatgctc cgctgttgcc ttcttgaaat    77700
tcataatcat ctttgaacaa ggggtcccgc agtgtgtggt ggctcacgcc tgtaatccca    77760
acactctggg aggctgaagc gggtggatca cctgaggtcg ggagtttgag accagcctga    77820
ccaacatggt gaaaccccat ctctactaaa aatacagaaa ttaaccaggc gtggttggtg    77880
ggtgcctgta atcccagcta ctcaggaggc tgaggcagga gaatcactca aacctgggag    77940
gtggaggttg cagtgagtcg agatcacgcc actgcactcc agcctgggca acagagcgag    78000
actccgtctc aaaaagaaa  aaccaagggg tcccacattt gcattttttgc tctgggtcct    78060
gtaaattacg tagccaggcc tgcatttgtc ctgggagatg ctctaccaaa aaacaataaa    78120
taacaccaag cattctgtaa tcaaacactg taggaacccc tgcttatcct agcctcattc    78180
tcattctgga agactgcaca tttatcatgt taaagactca gctagggagg cccaacttca    78240
ttcaactcag tgtttcttat ttttttaaaa cagaactcat tttttaaaaa aattattggc    78300
tgggcgtggt ggctcacgcc tgtaatccca gcactttggg aggccgaggt gggcggatca    78360
cgaggtcagg agatcgagac catcctggct aacacggtga aaccccgtct ctactaaaaa    78420
tacaaaaaaa aatgagctgg gcatggtggc gggcgcctgt agtcccagct actgggggagg    78480
ctgaggcagg agaatggcat gaacccggga ggcggagctt gctgtgagcc aagatcacgc    78540
cactgcactc cagcctgggc aacagagcga gactccatct caaaaaaaaa aaaaattat    78600
ttaaccctt tattttctgct gaatgtactt tagaaagatt gagtgatttg aataaagtga    78660
cggtggccta agagtctatt ttctggaatt gagggaatac tgccatcgat ccttgaaaaa    78720
tatttattta gttcctccta gaggccgggc acagtggctc acgcatgtaa tcctggcctg    78780
cactttggaa ggctgaggtg gacagattgc ctgagctcag gagttcaaga ccagcctggg    78840
taacaaggta aaacccgtct ctactaaaat acaaaaaatt agctgggcgt ggtgatgtgt    78900
gcttgtaatc ccagctactc gggaggctga ggcaggagaa ttgcttgaac tcaggaggcg    78960
```

```
gaggcagagg ttgcaatgag ctgggattgc accactgcac tccagcctgg gcaacagagc   79020
aagactctgt ctcaaaaaaa aaaaaaaatt atctagcccc tcctagaaat gttaattcct   79080
taaatctgag cttcagcttt ctgtgaagca gaattatctc caaactttaa caaacaatgg   79140
tcagaactgt ttttaaggtc ttggagagag atcattttca gtctttatta atcggacttg   79200
agattattta gaaacttggc tctgaatatt gtattcagaa tgttttcact catttgtgag   79260
taatttttta aatatcccct ttcctcagat gcagaatcag ggcttttttgt ccagcattat   79320
gttgcaagtc ctggttctgt tgaaacattc cataccatct gtgtgatggt tatcggcacc   79380
tccaccggtg ccctgaagac agttttgtgc tgtgagtcca gaaacaggaa acacttcagg   79440
ctgtgtgtca gaagcattgt cagtggttgt gttttgccca ctggcagggg gcattctttta   79500
aatcctggga tgcttctgcg ctttgggctc cactgttcca gcagtgatta gaaataacgc   79560
tgtaggccgg gcgcggtggc tcaccccgtg aatcccagca ctttgggagg ctgaggtggg   79620
cagattacct gaggtcagga gtgcgacacc agcctgacca acatggtgta accccgtctc   79680
tactaaaaat acaaaattag ctgggcgtgg tggcgcatgc ctgtaatccc agctactcag   79740
aaggctgagg cgggagaatc gcttgaacct gggaggccga ggttgcagtg agccgagatt   79800
gtgccattgc actccagcct gggcaacaag agcaaaactc tgtctcaaaa aaaaaagaaa   79860
taacaccctta gcccactgca ttattgacct gtgtctgcat gagctgtgga ccacattata   79920
atcagagaga tctctcagat gttgtcactt tcctgctcta cccgcagatg taaatttcag   79980
ccaacagcag tgtttgtgct cattttcccc ggctctccaca cacatgtaat ccttctgag   80040
catgttggct tcaaataata tggccagcca cctcttccac cacgagatct tcaggaaatg   80100
gcaggccact gggtttacat gcagatggca tgggagcaca caaggcacgg ctgtggggag   80160
ttggcacttg ctccagaata tggagcaccg agtgaaggtt tcagtttcct gcactgagag   80220
aaacaagggc attccgaggc ttttccactt tatccctaaa gagtttcaca acgcttgttt   80280
gccgatttct acatagatgc cacctttctg agttgtatgt atttacatgc caatgtatt   80340
cattgagcag cgttaaataa tggtgttcac ccctaaagtg catatactgg taaaattaag   80400
aatgatcgta ttaagcctc ttgcaatagt cattagttca gagaatattt aagaatatta   80460
aaggtgcttt gctaatgtcc tcgttagttt tgttttgaca aaatcagtac ttcagtttct   80520
tgtttctttt ttttttgaga cggagtcttg ctctcgctct gtcgcccaga ctggagactg   80580
gagtgcagtg gcacgatctt ggctcactgc aacgtccacc tcccaggttc aagcgattct   80640
cctgcctcag cctcccagt agctgggtt acaggcacac actatgcctg gctaattttt   80700
tttttttttt tgagacggag tctcgctctg tcacccagg tggagtgcag tggcgcaatg   80760
tcggctcact gcaagctctg cctcctggg tcacgccatt ctcctgcctc agcctcccga   80820
gtagctggga ctacaggcgc ccgccaccac acccagctaa ttttttttgta ttttttagtag   80880
agacggggt tcaccatgct ggccaggctg gtctcgaact cttgacctca ggtaaaccac   80940
ccacctcagc ctcccaaagt tctgggatta caggcgtgag ccaccatgcc cagcccagta   81000
cttcagtttc ttagcgatga aatccaccca atgtcaggcg atgactatta ttatttact   81060
gatttatact gtttgttctc tattaatgtc ttatttccc caaccgattt tgaagttgag   81120
taaggactat gttccgcggg tatcttgagt cctctgaggc actgagcttg gtgatttgga   81180
cgcaggagct gctcattagt gagctgatag ctgggagcat agcgcatccc acatccactg   81240
acttaccttg gtgtcctcct ttgtagcctt ttgtcataca tgatatggag acactgtgta   81300
tggctgagaa gacgctggtg gccaagctgg tggccaatgg catccagaac aaggaggcgg   81360
aggtccgcat ctttcactgc tgccagtgca cgtcagtgga gaccgtcacg gagctcacgg   81420
aattcgccaa ggccatccca ggcttcgcaa acttggacct gaacgatcaa gtgacattgc   81480
taaaatacgg agtttatgag gccatattcg ccatgctgtc ttctgtgatg aacaagacg   81540
ggatgctggt agcgtatgga aatgggttta taactcgtga attcctaaaa agcctaagga   81600
aaccgttctg tgatatcatg gaacccaagt ttgattttgc catgaagttc aatgcactgg   81660
aactggatga cagtgatatc tccctttttg tggctgctat catttgctgt ggaggtgagt   81720
ggttgattta atctgctggt atcatgtcac tgacaggctc ctgtcttgaa aaatttgaca   81780
atgggaaatc cagtaccagc ctgagctgtt ccagtggagg ggacactcac atggtgggaa   81840
gacgtctgac ccccagtcac tgctgagaat tcagtgggaa ttataacaat attgtataat   81900
attatagtat atattgttat tatctataaa tacatattta atattatgta aatgtatgac   81960
attttaatca taattattagc caggtgtggg ggtgcacacc tttagtccca gctacttact   82020
cagtagactg aggcaaaagg atctcttgag cccaggagtt caggttgcaa tgagttatga   82080
atgcaccact gcactctagc ctgggcaaca gaacaagacc tatttcttta aaaaaaaatt   82140
atatatttgg cacaaatata tatatagaga aaaagaggtc ggacatgggc ctgtaatccc   82200
agcccttttgg gaggctgagg tgggtggatc acttgagccc aggaggttga gaccagcctg   82260
ggcaacatgt caagacccc tctctacaaa aaaaaaaata gaaaaaatta gtcaagtatg   82320
gtggcatgta cctgtagtcc cagctacttg agaggctgag gtgggaggat cacttaagcc   82380
caggagacaa aggttgcagt gagccaaggt cacgccacca cactccagcc tgggcgacga   82440
agaatgaccc tgtctcaaaa aaaaaaaaaa aaaaaattat acacacacac acacacacac   82500
atttcgttta tattatatct aatattataa acagatataa tttatatatt atgatattcc   82560
tgtatatatt ataatgat gttgtattca tattatagac aatattgtat gaagtgctat   82620
acagatgtca gtagttgc tgtcacagtt ggttatgttg atgaaaagta tatttcctaa   82680
tgcaaaatat aatatcagtc agcagccaag tggcagtgac tgcaaggttt gctttgcccg   82740
aggaagcaga tcccagggaa ggccgatctg gtcctctctg tggaagctgg ctctgcaatg   82800
tccacatttt tggctcggtg tcacgttcct ttaaatagcc ccatctcagg tctaggaagg   82860
tcatccacct actgcaaact cggctgacct tacccagggt tggtggagac agatggggtc   82920
tcccacactg cctgcagcca tactgcgcct gggggattga ctcactgtca gcatggagct   82980
gactcagcc taccagccgt gcccgttact gtgtggctgg cacaagtca gatgaaggaa   83040
gtccttgcgc tctggcataa agtgtacaaa gacaaagcag tatgcataaa tttgtcctt   83100
agtatggtca ggatgtagca ttgtgggtaa aatgcagttg cagaactatt tatatgtagc   83160
atgatcacag ttttataaag gaaattaaaa tcctatatca atcctatgta tatagaaaaa   83220
tgtccagtga gatatatgtt aaacctatta tggtgggatt aaaattatga gggggatttt   83280
ctatttttca aaagattcct ccttttttttt tttttgaga cagagtctcc gtctgtcacc   83340
ctggctggag tgcagtggca cactcaag tcactgcaac ttccgcctcc tgggttcaag   83400
tgattcgcct gcctcagcct cctgagtagc tgagattaca ggaacatgcc agcacacctg   83460
gctaattttt gtatttttag taaagatggg gtttcaccat attggccagg ctggtctcaa   83520
actcctgacc ccgggtgacc cacccacctc ggcctcccaa agtgctggga ttacaggcat   83580
gagccactgc acccggcaat aattcctctc tttagagact taatagttat agccccagcc   83640
actctggagg ccgaggcagg aggattgctt gagcctagga gttccagtcc agcctaagca   83700
```

```
acagagcaag accccatcac taaaacaata caaaaacaag aatttagaa ataaaaactt   83760
aataattaca tttacaacca aaaacaatga agatgtttaa atcctcatca ctagcaaccc   83820
tgttaagaat catagtaatg actgggtctg taagggagca ccgcctgctg aacatggctc   83880
agggcagtat tttctggacc aagaatcagg tctcatgctt tgagactgtc ccaggatgtc   83940
tagtgccagc taccccaggc aggtcatctg gtgtgaatgt tgactcttcc tgcaccaagt   84000
ctcagacctg ccccacccte ctccccacte tgggtctect gatcttggct cactgcaate   84060
tccgtctccc aggttcaagc gattctccca cctcagcctc ccgagtatct gggattacag   84120
gcgtgagcca ccgtgcctgg cctacaaaac ctagttctaa cacaatcact ccttaaatat   84180
ggtggaacac ttgaagcttg atatctagtt tggattcaaa agcttcattt cccatattat   84240
gcaaaactgg tggttgtgat ctccagaatg tactgttcct cctactagct ctaattttc    84300
tccctgacag gtggtcatca ggtaaatcac aagtgaaaag gccgcaccat aaggtgtact   84360
tagggcacta ttgccgccta gtagtatgaa tatttaggaa agagtactgg tcctgtctgt   84420
ccctacttca cctattgact ttggaaaaac ctatgtctat cttccagtca agttgacaat   84480
atctaaaggc agctcagttt ttttctaaga aaggccacat aaaataggca tgtttggttc   84540
ctgaaactga taagcagttc ttgggtgatt atcacactca aacctctctc tcttcttcg    84600
agactagatc gtcctggcct tctaaacgta ggacacattg aaaaaatgca ggagggtatt   84660
gtacatgtgc tcagactcca cctgcagagc aaccacccgg acgatatctt tctcttccca   84720
aaacttcttc aaaaaatggc agacctccgg cagctggtga cggagcatgc gcagctggtg   84780
cagatcatca agaagacgga gtcggatgct gcgctgcacc cgctactgca ggagatctac   84840
agggacatgt actgagttcc ttcagatcag ccacaccttt tccaggagtt ctgaagctga   84900
cagcactaca aaggagacgg gggagcagca cgattttgca caaatatcca ccactttaac   84960
cttagagctt ggacagtcta agctgtaggt aaccggcata ttattccata tcttgtttt   85020
aaccagtact tctaagagca tagaactcaa atgctggggg taggtggcta atctcaggac   85080
tgggaagatt acgcgaatt atgctcaatg gtctgatttt aactcacccg atgttaatca    85140
atgcacattg ctttagatca cattcgtgat ttaccattta attaactggt aacctcaaaa   85200
ttcgtggcct gtcttcccat tcaccccgct tttgactatt gtgctccttt ataattctga   85260
aaactaatca gcactttta acaatgttta taatcctata agtctagatg tatccaaagg   85320
tgaagtatgt aaaaagcagc aaaatattta tttcaaagac ttcacttctg tttcctgaat   85380
ctaaagaaag acaacatgct gcttttaat cataggatgg agaattttaa agaactgttt    85440
gggccaggca cagtcgctca tacttgtaat cccagcactt tgggaggccg aggcgggtgg   85500
atcacaaggt cagcagatcg agaccatcct ggccaacatg gtgaaaccct gtctctacta   85560
aaaatacaaa aattagccgg gtgtggtggc acatgcctgt aatcccagct actcgggaag   85620
ctgaggcagg agaattgctt gaaccaggga gttggaggtt gcagtgagct aagactgcac   85680
cactgcacte cagcctggtg acagaacgag actctgtctt aaaaacaaac aaacaaaaa    85740
aaaatctgtt agataagcta tcaaaatgca gctgttgttt tgttttggc tcactgtttt    85800
cgtggttgta actaatatgt ggaaaggcc atttccaggt ttgcgtagaa gagcccagaa    85860
aacagagtct caagaccccc gctctggact gtcataagct agcacccgtg gtaagcggga   85920
cgagacaagc tcccgaagcc cgccagcttc ctgctccact cagtccgtc cagtcaacct    85980
gaacccaccc agtccagctg tctgtggaa tggtggtgtt cttagggaca gactgacacc    86040
ttacttgtca gtgttcctcc gggcccatt tggcagctcc cgtatctttt gttatgttgc    86100
ttttaaagat atgatgtttt attgtttaa ctcttggtga cagtagatgc tctctggagc    86160
gcagacgagg cacatgtgtc ttcatagcct gggctgggtg ggagccagtc accctgcgga   86220
tcgagaggg gggtagagtc ttcttcaaat ggcagttta cttcaaatgg cagatttcac    86280
aagagttggt tatttttac aatgggttag gttgttaagt ctcctttgta tgtaaggtag    86340
tttttttcaac atctaaaatt tttgttttag cctttcaaaac caacttacca acctcagtcc   86400
agctgggaag gcagcgttga ttatggtagt ttgtcaagaa tatatggacc tggaaacact   86460
ttctctctct gtccacctgg tagataaatt gtcctgttga gaatttttag atctggactg   86520
gaactgccag gaccaccgcc tccagggagt cgctgggcac ctggaggtat cgtcgatgcc   86580
tctcccccat ctttagaaaa tttggctctt ctgaggtcat tattatttta agaatgatta   86640
ggattgataa gggtcccatg accagcatta tgaaaatgcg agagtgggaa ggacacagtg   86700
tgagacttcc actagaaaaa agtgaaagtt aggtttagga catcctttt taaaaattac    86760
aaatttagtc cgttttggtt tttgtaatca ggctaggcac agtggctcac acatggaatc   86820
ccagcacttt gggaggccga ggtgggagga tcacttgagc ccaggagttc gagaccagcc   86880
taggcaacat agcaagaccc tgtctgtaca caaaatttaa aaattagttc atcggggtgg   86940
cacacatcag tagtcccagc tactctgcag gctgaggtgg gaggattgct tgaacccagg   87000
aggtcgaggc tgcagtgagc tgtgatctca ccactgcatt ccagcctggg tgacagagtt    87060
agattccacc ctctcccacc ccggcaaaaa aaaaaaaaaa agatgcaatc aaaggggctg    87120
ttggccagca atggcagcag cagcggcggg cagtctgccc aagtgtctta ggaaccaaaa    87180
gcaaataaaa gtgtttccat atatgccacc agccaagtgg ccatcctaat tcagaaagaa    87240
gctagccttt gagtgtctgt catggtgcat ccgtttcagt attatttcct aaaatgaaga    87300
gccctgtgt caacaagatc caggggctgg agcccaatgc caagcctgtg ttgtccccag    87360
cgaccctgca gctgctcgct ctgatgtacc ctgtgccatt caaggagatg tggtccagga    87420
aagtgagcct catggttttc agagaagtca ttgttctgtt tacattttca taaaaacctgt   87480
ttaaaatagc tccccgtctc aggctttcag cagtaacagt gagctgactg gcaagttgca    87540
tgttagctcc cgggacactc agcagcgatg tgagcatttt tggtttcctt aaggcccagc    87600
aagacttcca gggacatctc tggtgaagcc agaatggaga cacccgtgac ctcaggctga    87660
aagtcactcg acattggtct cttgtgttga tagggaagga aatcaggcat tcctatttct    87720
ttaaataaca aaaccactaa ttgccactca atgctggaat attttgggtc acctaatcat    87780
agatttctca gggcatcaat actcaaatat aggctgatta tgccccagtt caaatgggaa    87840
ctattaacag agtgcatttc ttgcttgctg ggtttcaaca gacatcagcc aaaagaacaa    87900
aagagatgtc aggacagatt ccaggagtgt cggagcacat gtgtggcacc cgctccctct    87960
ggcagcgaat gtaggaagtc gccaaattta cccactcttc aacaagtcat tgtttaaaca    88020
cggttttca tttctcaac ttaatagc aaaagtgcc aaagtcctca gagacctaac      88080
agccttgctc taccgtgctg acaggtgtga aggcacggtg agggactcct ccagacgtg     88140
cctcttgtgt gccagctggc tgtggctcgg gagcagacgc aggcctctcc attgtccagg    88200
ggagcctggc ggcgcatccc tcctctccca cctcctggca cttccagctg ggtgtccac     88260
atgttggatt ccgtccccac cacacttcca gagaccggag aactgtgcag ggcctaaggc    88320
cgtttggatg aattgtcaaa acaagatgct tccagttaca gcggcaggag cgggactggg    88380
agcacgggct gacggctgct ggtgcctttc ttcccacctc gcttgcctgt ttccgcttga    88440
```

```
cccttcctcc agctccgatg agaagagtat aaagcatctt cctaacgggt gtgtttgcta   88500
tacgaacata atggacgtga agtggggcag aaacccagaa ctcagcattc aaggatgccc   88560
aggagagctg tccctgtttt aaagagctgt gttttgtttt gtttcgcatt tagagagcag   88620
acaaggcacc cttctgctgc gctgatacgt ttcttacact gggccatttt agaccccag    88680
ggaaacagcc ttcctggagc gttgtctgga ggttccaggg acagggcagc ctcccagagc   88740
cgagcaagag ctcaaggtac aaatgagaga tttgctatac cgtgagaagt caacaactta   88800
gccaccactt ccccgcaatg gaccatgtaa caaatacctc agcaggccct gcaaaaggcc   88860
atgctagagc tgaggcgcac agcctgtggc ctctgtagtt agggcaggtg ggatggagac   88920
tccttgagtg cacacacctg agcctgccca cacacagggg agcagcatct cgtatgacgt   88980
ctggaaggaa cttcggttgt gtaaagggag ccttgaagat acgtgcaaaa ggtgctaccc   89040
caatttggtg aaactgacat tgggcacgtc ttgggcttag gagaagcggc cgatggtccc   89100
ggcctgcagt gacaaacccc cctcccgca ccgcccccag caccccctct cctcttcacc    89160
tcttcctgct ggccacgagg aagccacttc ctcagagaga ccctaccaga tgcggatgga   89220
aacagatgca ccaaagcaag ccctgatgaa accgcgactt cctaaggtct gtctcctctg   89280
aacttgcacc tgggcctctc tgtgtttggt tccaagcact tcccacctca aactcccatt   89340
ttcaaaccac tgtatctctg cgcacatctg ctacttacca gccgcataca tgatggaggg   89400
ttttttggtc ctgatccagt ggccacacct gtctttgaaa tgtctcactg aactccagtt   89460
ttaaaataga ttcattgctt caacacagca agccagctac acccagctaa gactggcttg   89520
accgacagcc tggcctttgg tggggggctt cctgggcct ggggaaagct ggccaccttc    89580
aacagctggt acctcttcaa cagtgtggcc tttcaaaatg cagatgccac caggagaaca   89640
tgcccacagc tcaccaccta tggatgccat ggctctgggc agctttcaaa gcaggttcct   89700
gtggtctcct cagctgtttg aggggtaac agcaaatcag cctccatttt aaaatgaaaa    89760
caccagcctc cagatgtagg gcctgctggg tgttgctagc cgctggtccc caggcacggt   89820
gcactttctc cacctcctgc agcctccctg ttgtttctag actcttgcac ctggtgagtg   89880
caaggatagg tgacccaggg gcctgcagcc ttgtcctcag ctcccatctc ctggactgcc   89940
agcctcaccc tctgcagtta gcatggttgg cctgatgcag ggatcccgag ggattacttt   90000
ttagaccttc tttcacattc agaaaagtag tatagattca ggagaggcaa gaaaattatg   90060
ctgtccatag aagtcaccca tgaagactga tgccaccacc tgaaggctca tgattgttaa   90120
aaatgtccac gggaacctct cgtccacagg aggtttgtct caacacttcc catttttacg   90180
gcattggcat tgccaagcat ggggaagtat ctgctcttct catgttaaaa gtggcccagc   90240
ttttcttaac tcagtccaag ctgacttgtt tagctgcact ggaatttctt accaaccaaa   90300
tatttgcatc gagcaaaggg ggctgtgtgc acctccctaa tggcagcgat gatggctgct   90360
gtcattcaag cccatcttca gacgtcacag tctggaagtg aaatgtccac aaacatctgt   90420
ggcagaaaag gctatacgga ccacccagtt gtgctgcagc tttacagagc aaggaagggt   90480
tgtggcaaat aaatgattaa cctgcctcga ctgtgctgag ggcaacaaag gccatctcac   90540
caaaggatta ttcgatgcca ttaaatcatc ccgtgacctt cctgcttccg agtccatggc   90600
ctttgcccag ggcatgtact cccctgagag gccttctgcc tagaaagatc tatgactggg   90660
ttccaaagtt gaggcctagg tttttgctgg gattagata ttttcaggca ccattttgac    90720
agcattcagg aaaacggtta ttgaccccat agactaggt aagaataaag gcaataaatt    90780
tggtctgact cagaatatag gagatccata tatttctctg gaaaccacag tgtacactaa   90840
aatgtgaaat tgaaggtttt gttaaaaaga aaaagataat gagcttcatg ctttgtttaa   90900
ttacataatg atttccatta cgctatttct gtgaaatgca gcaggttctt aaacgttatt   90960
tcagtggcat gggctggaag cttatcacaa aaagccatgt gtgtggcctt atcagaacag   91020
aaagagacag gctggtgccc aaggctgctg cctgctccac cttttgccag ctctggacat   91080
ctgaggacgt cccggcagat ctggaatggg gccctcaact gaccatttgc ttctcagaat   91140
ttcagtttga gacatgagag gtataatcag ttactttcct ccccccagag aaaccctttt   91200
gtgaggggag aggagctatg gtatgtggtt cagctgaaac acatacaact gcatcctttt   91260
ggagtccttt gccaacaaaa acagaccaac agaccagatg gtgtccatgt tcaatatcat   91320
gtcttgatgg acgcagctga tgacctcaaa tacttgagtg gtctcatggc tgttagatgg   91380
attatttgaa aaaaaaaaa aaaaagaga gaaaaaataa ttgattttta catcagagat    91440
agcaaactaa gacctgggga gggggttcag ctttttatttt attttatttt ttttaagttt   91500
gctagttggg tcaaatgtga ggaggaggga gtctacctgc cacctcttct cttgcccctc   91560
ttctgcccac acatccagca tccaaaatcc attcatttaa tgaattgata aagtgccgtg   91620
caaactggtg cacaaacagg cccccagtcc acgcagcctg gctcctagga aaagtggtga   91680
ccggggctgg gggggcatgc cgcagccctg ggacacagtc gggcaccttc cccggacccc   91740
caggccttgg ctgtgcctca agtcagagag ggtcagcctt caggcccgg agacgagtcg    91800
ctggccgatc atttcacaat aaaatcactc acttttggca acttcacttt ttttaaggca   91860
cagtcagttc cttttctcat gtacctcaca aaagatgaag accatgtagt actctttttg   91920
gtaaagttac agtgttcatg ttaaaatatca ctttttttca cattgtgtgg taaaaagaac   91980
tacgttaata gctatatctt aaatactgtg atttgacttt tgaaaaata tcctaataca    92040
aatatttac taacttacaa tcactcattt aataagaaac atttggattc ttttgaaatc    92100
agtgttaatt gactcatatt cttaaaagcc tggctcttga cccattgga aacacaaagg    92160
aagctgaaat caaacatcta aaatacactg cgtacacgtg tgcgtgcaca cacacacaca   92220
cacacacaca cacacagtc ttcatttctc ctgagccatg cagaatttac tttcaatgtg    92280
gaaatctgtt ccctttacca cactgtatat gcacagagca caagagaggc tatctctagt   92340
cacttccacc agcgaggcct tagactccgt attagaggcc accgatttca tacaacagtg   92400
tttcgctaaa gaccccttcac tattcttgtt tagtaaaatag ctgtctgctc ttcagggaac   92460
tgttacctat gggttattac caaagaacgc tggcaattgg aaatgtcctg atggaaattc   92520
tttgcacgtg ccggttctct ggcatcctcc aggtggccca accaaagca gaaagcagaa    92580
accacagacc ccgtgagtct ccccatacct tgtttccaat aacttggcaa aacttcttgg   92640
tgcatattgg ttacaccctc tgggattcat aatgccatta ggctaaaacc ctaagagaga   92700
gggttgcacag aaacacacgc gagaatgagg cagatcccag agcaaggact gggcccgac    92760
tctccacatg tgctctacta gtgagtgcct tatactctca gtattttggg gcttacagct   92820
tcttatttgt gctaaaaagg tgcagttcca aagtaggaac tgccacacag gcccagcat    92880
cctctctcca acttcatacc tctctcctgg tgggggagc gggcatccag gcctccgga    92940
atcaaggat tgcagagaag agcgaaagta attttttctag tcacatgaac tgattggttc   93000
caggcaatta gaaaatggct ataaaataac cttaatttta aaaaaaaatc ttgggtcttc   93060
gttttcctat taggagactg aactgaccac atgtattgat ttatatcctg aatatatggg   93120
aacttctgtg tttgggatgt cctactgtaa gactgatgaa tgtacagagt taatttcagg   93180
```

```
gtacagtttt gccttaatgg tttttaaaaaa taaactatttt tttaaaatttt t              93231
```

| SEQ ID NO: 3 | moltype = DNA   length = 15496 |
|---|---|
| FEATURE | Location/Qualifiers |
| source | 1..15496 |
| | mol_type = other DNA |
| | organism = Homo sapiens |

SEQUENCE: 3
```
ggctccaccc ccaagccagg cgaggcaggt tccgaggttg gaacacctgg cgagtcctcg   60
gtgtcggtgg ccggcagtca tctcgcggcc gttcaggtga gggggttgga ggagtggctc  120
atgagcgagg aaggggggagc aggcgggctc ccacccggtg ctccgtgaga tcgagggggag 180
cgggttctgg gtgcggatgc acgcgctggg cgggacgctg gcagtggtac ccgagacggg  240
gcggaaggag actggagtga aggtgggcct aggctaaggt acgtgctaga aaggatgaaa  300
acggagtgaa attcttaagt gatggaacta ggctagggca tgtttcttgc cctttaaaat  360
gtgttgtctt cgggagacag gacgtagaag atagttgcag cacagggtga taggctggcg  420
aaagttatac aaaagcagga accactagaa ggaggtaaga tgtagtggtgc tttgggagta  480
gtggggttgg gaagggcgtc cgagaggagg ttactgaagg atgactagga gttgaatggg  540
aggacatcac ctgtaaggga acgatatttc cgtgggcaga gaggaatgaa gcagtagcaa  600
ccatgagtga tcagatactg caaaaatgtg aagtgtagga tggcgagaat gtaagaaatg  660
aagagtgaag aagtctggaa gggcctcgtg tgcatcaatc acagcggggc ttgatcttta  720
tgcttagggc aagcactccc ttgaacttttg agtgttttaa ggaggttatc tctgatgttt  780
aaatttatat agatcgtggc attgcatctt agaaataagt tttaggaagg gcaagcttgg  840
aggcagggca agtccagaaa atgaaggagc tggtgaaatc cgtgttaaag tgccaaagga  900
cagagactgg ctgacagcta aacttcaagg tttctgagaa tccacaaata actaaatttta 960
tctagtcaac ctgttccaga acaggcttcc agtcatttag gttgcccaag aatgagtaaa 1020
ggaaaaggaa attcaatttt ccaagacctt gtttccctc tcctctttaa ttccttgttc  1080
ggttagcaac agtatatcca ttccctcgct cctttgtgaa aagtaaattc ctgaatgtta 1140
actaaaccaa gtgtttctaa attgggtaag agttgaaga cttaaggcag cagaatggga  1200
gagacttaaa acgttatgtc tgagaattag gcattaaagg aggcctagta tttgggcggg  1260
ggttgtgagg agcacatact gaacctttgg acctgttgag tgagttcatg tgcctctgaa  1320
ctctctgact ggatatgacc agtaaacttg gataattaga tcctggagtt taggggagag  1380
ggctagagat agagatgatg gatgtcagca tattttaaa acagaaaata gttaagatca  1440
cccaagacaa tctggaatcg ttagaaggga gtaaggaagg cattattggg aaactttcca 1500
gcttcaattc tcatattttt tctaatctcc tggttgagtc tttggagttg ctgttctctg  1560
tatgcaaaac ccctcccttg accctctctc cctcactcta tttttaatt tgtcacctcc  1620
ttctcctgtt ctaggtctca gtttagatag caccttctc tagaagttca tagcactgtg  1680
tattccccc tttattgttc ttatcacata atttttgatg gtttgacac tagttgttat   1740
tcctcactaa attttatgtt ttatgaactc aggggtaagg gcaccagcta gcacaatgaa  1800
tgcacaatac ttgtcagagt gaatgcattt aagttccaag aaccaaggaa aggcggtatt  1860
tcaagaagag aagtatcaaa tcttccagat tagtcaaata aactccaaaa aaaaaaaaaa  1920
aggtttattg gatttggcag ctggagatcc atagcgattt ttttttttt tttttttttt   1980
ttttgagacg gagtctcact ctgtcgccca ggctggaatg cagtgtcgtg atctctgctc  2040
gctgcaacct cagcctcccg ggttcaagca atttctctgc ctcagcctcc ccagtaggtg  2100
gaattacagg catacgccac cacacccggc taattttttt gtattttttt ggtggagatg  2160
tttcaccata ttggccagac tggtctgaa ctcctgacct tgtgatccgc ccacctcagc  2220
ctcccaaagt gctgggatta ccagcgtaag ccaccacacc cagcctcctt agtgatttta  2280
gtaagagtaa gttcagtgca gtgatgacaa tagaatgcag attgcagttg ctagaatata  2340
aacaggaaat aagaagataa agacaactcg tggaatacct tttcatagag cttaggtaaa  2400
ctgtaggaat tattctcctt gtactctaat acttattatg ggttttatt ataattatag   2460
tgtaatataa tggatgagtg catggccttc cccacttagc atttgttaag cattaactta  2520
acattaagca ttagacttttg ggcaagttgc ttaatctttc taaacctcag ttattttatc 2580
tataaaatgg tgataaaata atacctacct cacgaaggtg tggtaaggat taaagtgaaa  2640
atgtagagag caggtagcat gctttgaaca cagttcttgg cacagaaagt gcccaataat  2700
tgttagtttc ttgtagctat tacatgccag gtcctgtgct aactaagcgc tttatatgca  2760
ttgtctcttg gactcattgg aagacctact gttttaattt ttgctgctga taaaactgca  2820
tcacagagag gttacctaat ttgcccaagg tcacaggaca ggactagtaa gtggtcttgg  2880
ttcattattg tcaaatttac taatcacctt gagaaaaatt aagattggat ggttgcctta  2940
ttttacaact tagaagatga ttgaagacat tttggtgcag gtggggagcc agattgcaag  3000
tagctcagtg agttgtgtgg gtgagttaag caacctttt tattcttttt tttgagacg   3060
gagttttgct gttggtgccc aggctagagt gcagtcacag cttactgaaa cctccacctc  3120
ctcatttcaa gcgattcacc tgaactcctg accttaggtg atctgccgc atcagcctcc   3180
ccaaggtgct gggattacag gcgtgagcca ccatgcccag ctgagttaag caatctttat  3240
gtagagctct ccttttgagaa agaagttggt tggtcaaag aaagataaat gggacagtgg   3300
cttggaagag gtaatcgagg ctaggaaggt gtttatcaac aaggaagat gtaggctggg   3360
cgcagtggct cacacctata atccccacac tttgggaggc tgagatggga ggattacttg   3420
agcctaggag tttaagacca gtctgggcaa cataggtga ccctgtctc cacaaaaaat    3480
taaaaaaatt agccaggcgt ggtggcatgt gcctgtggtc ccagctacga ggggctgagg  3540
tgggaggatt gcttgagcct ggggaggtcga ggctgcaatg agccataatt gtgccactgc  3600
actccagctt gggtgacaaa gtgagaccct gtctcaaaaa aaaagaaaaa aaaaaagaaa  3660
agacgtgaat gtgtttttag acctgaagga atgattcca tgaaggggaga aggatgaaag   3720
atgggaaagg ataagtgatg acaagttct tgaggtaaga taagaacaca ggaagactag   3780
tcagtcttag aggaaagaat gaatgagcaa agaaattttaa aggcctgtaa tgacacagga  3840
tggaacacta tagtcactgt ggtgtaagtc atttgagatg agtaggacag aaggaggacg  3900
gcctcaagtg aattcagtg cctgaggag ttggctaagt tctcaattat ccttctgtta     3960
aatgggataa aaggtcagtt tgagaagtgt tggggaaggg gactttaaa gcactattta   4020
gaatgcttct gaggctttaa aatactcatt tttaaatgg tccaaaaat tcataattta    4080
gaagcagcag tggtgaacat ttttaggaaa gtgacccttg agaagtttat tttttggtta  4140
gtgacctatt gagcttatttt attaggtaag tagaacatgc tcatttaaaa agtttaaatt  4200
gtgcaaaaga catatgtcag attttttttt ctgtcttcca taacactatt tcctacccgg   4260
```

```
ccgcgctctg tcttccgtaa cactctcccc tacccgtcg ccactctgtc ttccataaca   4320
ctgtcccta  ctccaccaca ctgtctccta cccgccgag  ctgtcttcca taacactctc   4380
ccctaccccg ccacgctgtc ttcattaaca ctatctcctg ccctgccaca caactctgtt   4440
ttcctagaag tcaccagtgt gaattttttcc ctttatccat atgtacattt tttgtttctg   4500
tgtgtctgtg tatatacata tgcataaaag tgcatagata aaatacatat ccttttcaaa   4560
aaatcttaag tggggctctt gctatgcata ctgttctgta acttgttact tggattaaca   4620
ctgtatctta gacatctttc tatgtagagc gtatagatct tccctgttct tttaaatggc   4680
tgtataattg tctatggaag gacttaattt atttaaccca taccttgttg atggcttatt   4740
tgtgttttgc ttttatttt  tcctcttttgt ttttgctgct acaagcaatg cttccttcca   4800
tcttagcgga tctgtctttg tacccttgaa tgagaaagtt gctggatcaa aggatgtatt   4860
cattttgaat taggtgttgc taattttttcc tccaatgata cactgatgta tccccctgc   4920
ccacagtgtg tggtcatgcc tgttctctca ccctcttacc agtactggac attaataagc   4980
ttttaaagat ttgctactca ggctaaaagt gtctctttgt tttagggtgc atttcctcat   5040
ttaatgaagt gaagattctt ccttgtttag tgaccatttg cctttatttt tctgtgaact   5100
gcttgtgaat ggcatttgtc gttcttctgt tgtctttttta gtctttttttc taaagcacac   5160
tttgtagccc tttgttgtaa aatgttggaa atattttttcc cagtttgtca tttaatcttt   5220
gactttgtct ttctattccc cagtaggagg tacttaattt ttatatactc atatttggca   5280
ggcttttttct ttataggttc ttttggcttt aagtgatact tttaaaccca gctattgctc   5340
atttaaatta gaacctttttc catgagaacc acactgacga tttctttaaa tatagcttga   5400
aaaaatttttt ccctattgt  tcttttagct attgttcttg aaaataatgt gtttttttaaa   5460
ggaatatcta caaatagaaa tggtgatgat atccagcaaa tgttttaaaa tggtgtaaaa   5520
ccatttgtac tcctttagta attttttttggt aaaaaattta tactcccttta gtaattatca   5580
tttttaaaat gatcagagga tgcattttttt aactgttttta ttttttttgaaa gctcattgtt   5640
taacttatta tatatgtatt catttctaca gaattataag gctgtctgca gagatttgaa   5700
aaatggcaac aaatgaaagt gtcagcatct ttagttcagc atccttggct gtggaatatg   5760
tagattcact tttacctgag aatcctctgc aagaaccatt taaaaatgct tggaactata   5820
tgttgaataa ttatacaaag ttccagattg caacatgggg atcccttata gttcatgaag   5880
cccttttattt cttattctgt ttacctggat ttttatttca atttatacct tatatgaaaa   5940
aatacaaaat tcaaaggtg  agtataaggg actagaaata gaatattatc attaatgttg   6000
ctgaatattt taaaagtaca tagggctttg ttttgtgagg ctaaagcagt gatatccaat   6060
agaaatgatga agccacgtat gtaattttaa attttctagt agaatacata gaaaaggtaa   6120
aaagaaataa ggaaattaat ttcataatgt gtatcattta gctcaataaa tgtaaactat   6180
cgctgggtgc agggtccatg cctgtaattc cagcactttg ggaggccaag gcaggaggat   6240
tgcttgaggc caggagttca agaccatcct gggaaacata gcaagaccct gtctctacaa   6300
aaaagataca aaaataccca ggcatggtga tgtaagtcct agctacttat gaggctgaag   6360
cagaaagatt gcagcactat actctagcat aggcgacaga gtgagacctt gtctcaaaaa   6420
aaataagaaa taaatgtaaa ttattattttc aatcagtaat caaattctaa aaaatactta   6480
atgagatatt taatcaagtct ttgcaattcc gtgtgtattt tacattaatt ttagtctatc   6540
tcaatttaga ctagccatgt ttaaagtgtt tggaagccac atgttactag ttgctcctga   6600
attgagcaac acagtcctag gtcattattg ataacatttc aagaatactt tgttaaattg   6660
ggctttaagt agatgtgatg gttatctaac ttaagtttat gaatttttaat gtttaagcta   6720
gctggaaagg aaaggtgtgg tgatttgcgc atattttgca gttcaccca  actctatgtt   6780
ccagtaaatc taagggactg ttaatacact acgaccttga tcagggctat tcaagttttt   6840
tttccctaaaa tatatggtag gtagttctgc agcattcgta tcatcccaaa taaggaggta   6900
atgctcctcg tttctggata tttgcttcat tgcactaaat gttgagaggt cgctatgtac   6960
atgacaaggt gaaatctcat atgtagcctg tgagcttgac gtgagaattt ggagtagctt   7020
attagaaaga tgaattatttt gttagaatttt gtaagctgat gatagtttct agtgtttgct   7080
gtttactttt cataaaaagt cattccaaac taaaactcag gggcacacag tcttggtaga   7140
aagtagacca ttgagagtat tcatctatgg aaagtaattt acattcactt agtacaattg   7200
gccctccata tccatgggtt gttgtatcca tggatccaac caactgcaga tcagaaatat   7260
tcaggggaaa aaaattgtgt ctacactgaa catgtacagt cttttttttttc cttgtcatta   7320
ttcaaaatga caactatttta tagagcattt gcattttatt aagtattata agtgctgtag   7380
agatgattta aagtatacga gaggattcgt gtaggttatg tcaaatacta tgtcatttta   7440
tatcaggcac ttgagcatct tcagatcttg gtatttgcag aaagtcccag aaccaatcct   7500
caaaagatac caaaggacaa ctgtatatat tttggatggc agtctgtaca cattctctgt   7560
tatcattctg ttagtttcac agcctctccc agagtctcac tttaagcagg tattaatatt   7620
agtcctctct ggggataatg cagggggtcag atgactgtgg actccaggcc aaggagaaa    7680
agagcaaagg gtaaaggcga aggaaataaa aaataggagg gccaaaggag agtactctgt   7740
gaccctcaat taaggtcaca gaagctccaa agtgcttttt aggaaagcag ctgctttgaa   7800
aggcagaatt aagtcaggac gtctaagttc taatgcacct ttagggtgat tgtggctgcc   7860
gtgtttcacc cagtgattta tttataggc  ttattcattg taattcattg tatggctggc   7920
caggcaaaag catcctttttt ctccttcact gcagtttgta actgactcac tggttagaag   7980
tagtaacctt tgcagagaga caaaggactt tctcaggcaa gggtatatga gcagctttaa   8040
aatataatgt ggcaaaggaa agaataagct gtagtctagt tggtcagagc tagttgttta   8100
tgaacagatt gtaaggctgg ataatttgac ttcaagtctg tactcagcaa gtctttatgt   8160
ttcataacca ttaaagtcca tgctttgagc attttttgata aaaaatgtga ttttaaacca   8220
ggactagttt tcacaagtta aaggagtttt aaaagaaacc aaaatattgg tacaaattaa   8280
ttacaggttt atgcatttcg aaggcagata ccctgattaa cattgagggt atcaattgtt   8340
taagataaaa tatttgagaa ttatatttaa catatgcaat aaatgttttt attcttaaaa   8400
ttgtcgaaaa gaatgaagaa agttggtggt ggtgatgaaa tagtactaaa gactttctgc   8460
tttcaaacag aacagacaac tggagagcta atgcacatcc ttgctagtta ggcgaaaatt   8520
tcacaggaat gaaaagtaa  agcagacttt gcaggatcta tttctttaaa aaaaaaaaa    8580
acatacatct tagtaattct ccaaaaattt tcctcaaaga taaatgtact aaaaatatta   8640
tttctgaagt tgtgtgggct tgtaaaggta ttccttttata ttaagtacag ttatgcataa   8700
agaaagtaaa atatggtaaa ctttcatatt gcactaggta tgaattcgta ttgctaactg   8760
tctttgtaac taatttatgt atactgtaaa tggtatagca tgtgatttta ttatagttga   8820
ttaactttgt aatttctgta actgcatcga tatcccagtc tacctggaaa attaagtcta   8880
ttaaccatag ttgctgtagg agacagtact attgccaact gaagcctgaa tccttcattt   8940
attttgtccc caattacaga gtggaggttt agaggagtgg ggttagataa tgctcagatt   9000
```

```
agaaatacaa aggcagctgt cagatcctcc cattttattg ttgaagaaac tgagttgtaa  9060
acatcacaag agctagttaa ctggtgagta gcagccctgg tattagagca caagtctctg  9120
gattgattct tagttcagtg cttttcctat ttttgtcagg aagataaccc ttaaagaatt  9180
tcaagaacag agctggatct ggagacctag attttagtta gtccaacttc tgctaataac  9240
tgcgtgtgtg accctgccca agctggttga cctcttttgg cttctgctga tgcgcagtag  9300
ttcccgtact ttggatatcg tggttcaatt aaaagagttt tgttggcgga tacctgaatt  9360
tttcagcagt gacatttaaa acaaagcaat aactgatatt tattgtcacc atcgttttgt  9420
taagcccaaa gcactttttt aagtgcagtc ctataaattg aatacattta gttagtgttt  9480
gttttgtttt gctttgtttt ttataatgac ttgctaagca aatgggtatc ctgatgaggt  9540
cttaacgaac atcccatgtt gatctaactt ttctcatttt gacttgaatc tgtgaactcc  9600
ataatcagga catatctgtg tacttctcaa ctcagagagt ttataattct gtcattggat  9660
ttgaacaaaa gtgcatttat ttgttggaat gaataccact gagtgcctgg aagcatcgac  9720
ttactgtgta aaaggcttcc aatgcttcgt atacaacttc tcaattgtg gacacccaac  9780
agtaatctta gcatattata tttcttcttc tctgaaactt ctggtaaaag aagtgaagtg  9840
aatgatctgt ggcagcaaag actggagaat tattcattcc atagtgtttc ttagttttgtt  9900
tgagatcatc atggctaggc gcatctgtta acagtttctt cacctgaagt agtgatagta  9960
gttgtcaaga atttagaagg caaagattcc tgagtcttag ttatataaag ttaacataac 10020
tgacgtagaa ttaaggtcca acataaacag agaacaaatt aggtcaagtt aaactctgat 10080
agcagagact aatattagat attgtgattt ttcttcgtag gataagccag agacatggga 10140
aaaccaatgg aagtgtttca aagttcttct ctttaatcac ttctgtatcc agctgccttt 10200
gatttgtgga acctattatt ttacagagta tttcaatatt ccttatgatt gggaaagaat 10260
gccaagatgg tacgtagata aaaatttggc ttttacaccc agtgtggct tattcagtta 10320
agttatactt aatgtttacc cgttttctta attttagtta atgtttgttc taaactttgg 10380
aagtaaataa atagtagaaa agtaaaccac agtaaaatct taaaatgttt ccattttac 10440
atcttttaaa tatttattg gaaggtgagc ttctagtatc agaagtttcc ataacgtctt 10500
ttgtatgttt atatacatgt ataagtgctt atgttgacaa aaatatatta cattttaatt 10560
ttaaaatgaa tgaaatatat gagaatcatt tatgaggttt atagaaattg tgtttacatg 10620
aacaaaata tgtatgtgta tatatatata tatatatata tacacacata tatatataca 10680
cacacatata tatactcatg cgtcacttaa cggatatctc ttgagaaaag tgtcatgagg 10740
caagttgtgt gaacattgta atgaaatgaa atttggtctaa tgggcagtct ctttaacctt 10800
atatcaagtt atgtagctgt atctggtggt tttgagaatt tatttatgaa tatatccaat 10860
taggtcaacc tggtaagtgg gtgggtggtt ttatgtaatg tctcaagcag tgatcccaac 10920
taaaagtctg gatagtttaa gtaaaaatta tttcttacac attacaacat ttttatctta 10980
aaggtatttt cttttggcaa gatgcttttg ttgtgcagtc attgaagata cttggcacta 11040
ttttctgcat agactcttac accacaaaag aatatccata tattattcata aagttcatca 11100
tgagtttcag gtatgtgaga gttatattta attcttctg ttagaggcaa aatgtctatt 11160
ttaattgcct gagcattttt ctaaaattgt tggtgacgtt tttattttct tttcctttgg 11220
catgattatt aagaacaata cacacacata caaacaagcc atttctacac attgttttca 11280
ttatttaaat ttcatggtaa attgagatct gaaagaaaaa tattatatga aagttcggac 11340
ttccatcctt gtggacagtg ctacactggc acagctagat cctcacattg ctaactccca 11400
caaaacagt aacttctatg agcactgctt ttttttttt tttttttttt tttgagatag 11460
agttttgctc ttgttgccca ggctggactg caatggcatg atctcagctc actgcaacct 11520
tcacctcctg ggttcaagca attcctctgc ctcagccttt caggtagctg ggattacagg 11580
catgcgtcac cacgcgtggc taatttttgta tttttagtag agacaggatt tcactatgtt 11640
ggtcaggctg gtctcgaact cctgacctca ggtgatccac cgccttgga ctcgcaaagt 11700
gctgggatta caggcgtgag ccaccatgcc cggccaatta gaattgcttt gatgtagctt 11760
tgtcaactgg ttatgtgagt atgttttgca ttgaccgtga ttacatggtg tgccaaatca 11820
agcctctctt tattagaaga acaaatataa atacttaagt caaaattaga gttcaagtca 11880
attatttaat gcctttatct taaaccatca aagcacagcaa gatttatat ccctagactt 11940
ttgatgtgga gtaaggtatt ttattgaga attgctagta ttatttataa gtgtatgact 12000
agataaatca tcactacata tagaatcaat ataacttttgt aaaacttttat gcataaatag 12060
gatatatata ttagtgaagt ctccagtgaa gcagaatcat tggggtatat atatgcagag 12120
agagatttat tttaaggaat cagctcatgc aagtgtgcgg ctgtcaagtc tgaaatctgt 12180
aaagcaggct acagactaga aatccaggta agaattgttg cagccttggg tccaaattcc 12240
atggagcagc aagttggaaa ctcaggcagg gtttcagttg tgcagtctcg agaatccttc 12300
ttcaggaaac ctcagccttt tatcctgaag gccttcaaat gattggatga agcccacccct 12360
cattatgaag ggtaatcacc tttactcagt ctactgattt aaatgttaac aacatctaaa 12420
aaataccttc acaacaacat ctagactggt atttaatcaa acagttggat atcatagcct 12480
agccaagttg acacataaaa ttgaccatca caatagctaa gaaattaaga atttcttatc 12540
tgtttgtctt aggctccatt tggaatgaa gctgaatatg cacatccttt ggagactcta 12600
attcttggaa ctggatttttt cattggaatc gtgcttttgt gtgatcatgt aattcttctt 12660
tgggcatggg tgaccattcg tttattagaa actattgatg tccataggtg agtattaatt 12720
tctgttcagg tataaagcat aatgaaatat atttattttc atggccataa gattatcata 12780
tttctaagga gactaatagg agaagttaat cttcttaatg ttatattaag aaaacataac 12840
tgttggataa aagtttaaat aatagatgtt tttacattct agcctatgct gttataattt 12900
ttatagtgat aatgtgttat tagggcaagt atatattcag gaccagcaat ttccttatcc 12960
ttctgtaata aacctaaact taactcatat ttgaaaaaaa tatcaaagca ttcagccttc 13020
cttgaataag actttctaat ctctactgtt cagcagtcgat aaaggcactt gcaagatgaa 13080
actactactt gtaacacata catatttcaa atgcatcctt tctgttgatt ggaagacatt 13140
ttgtggtaaa ttatttatat tgaatgcctt cttaaatgct tatcctaatt gttcattatt 13200
ttttaattat atgttcattg cattttgact tgggacatac ttctgtactc atgaatgcag 13260
aatatcaaat tctaagaatt attttttaaag tgctaaagta gcaaaattaa tgcttctagt 13320
cctaggcaga gaatattctt ctgtagaaaa attgtaattg acatttctttt ctttttttttt 13380
tctatccatt gtttcttttct gccttcctttc tctcaaggaa gagaaggtta 13440
gagtgattca aataagtata actgatgtc tgattgtaga tatgtagttg gaaataaagg 13500
agcatacttt aaatgggact cttttttgaa gccatttgtc ttctgccaac tatagaaaag 13560
tacactggta ttttgattaa ttgtggtaca tttgattcca acttgtcatt gcctaaaaaa 13620
gtaaatgaag ttgctataca gggattcatg ggcctgccct tttaatact tgatactaat 13680
tttatgtgac ttttcctaaa aaacatattt agtattttgg gctttattta caactgttat 13740
```

```
acatgatggt gagaaagctt cctctaaaac ataaaagaaa attaattctt aaaaatctgt   13800
gtctaaagat tcattactat aatccgtctc ttccatcatt catatatttt atcataaaat   13860
aaatgatttt cttagttttt ttaaggattt tttttcttag agtggtttct agaatataca   13920
ccattttctg tgtttgctgt ttgtgaacac ttagaaataa agtggtctag gcaaagtggc   13980
atgttatcta aattggttaa tgtgaacaca tgattattaa taaaaacaac aatcatttga   14040
gatgtattta ttccttaata atctttatca tttttgtttc agtggttatg atattcctct   14100
caacccttta aatctgatcc ctttctatgc tggttctcgg catcatgatt tccaccacat   14160
gaacttcatt ggaaactatg cttcaacatt tacatggtgg gatcgaattt ttggaacaga   14220
ctctcagtat aatgcctata atgaaaagag gaagaagttt gagaaaaaga ctgaataaat   14280
atctcacgta aaccttcctg aaagataaac gttttcctga attcagaaac tagtagctaa   14340
cattgcttct ggagagcaga aataagcatg tcttctggct actaagtgat aaaaagaaca   14400
ttaacaacct ttaattacct tcctagtggg aactttttct actttaccta caagttctat   14460
atatgtagaa atgaataaat atatatttaa gtacagtttt catgaggaag ttttaaaaga   14520
ccatgttcct aagcttccaa gaaggttttg gatactagaa gtattaatct atggcttttc   14580
tcccagtaaa accataggcc tgaagttcac attgggtctt taaatctttt agatatatac   14640
tggtcatttc agaaaattct tcatagtggt attggcctta tatttaactt tttttttatt   14700
ttttttttga gacaaagcca cactctgtct ccttggctgg agtgtggtgg cacagtctca   14760
gctcactgca acctctgcct cccagttcaa gcaattcttc tgcctcagcc tcccaagtag   14820
ctgggattac aggcacccgc caccacgccc agctaatttt tgtatttttg tagagatggg   14880
gtttcacgat gttggccagg ctggtctcaa acttctgacc tcaagtgatc tgcccacctt   14940
ggcctcccaa agtgctggga ttacaggtgt aagccactgc gcccggcctt tttaacttta   15000
aacatgtttt agaattcacc taaagatcaa aatatcatgg attgaacctc atcaattgat   15060
agcagtgagt gactgaagct tccaaatcaa gaaaagccgg caccaagaac ttccattcta   15120
atctagagct gaccagtttg agctgattct ctctttgaag agtccttctt gattgcagtg   15180
cagtactggc atttctgaat ggatgtaagt ggagtatttt agtctaaagg cttttcaaat   15240
ttgtgaatt ttttttaaaaa ttgaggagct ttatttctat ttacccttcc attttttgtat   15300
atcaaatttc cattgtcatt aaaaactgta tcttgaaact ttgtgaactg acttgctgta   15360
tttgcacttt gagctcttga aataaatgtg attttttgtgt gattatctgg tttccagttt   15420
taaacattaa ctgtcacctt ttattcttaa acttgaaagt acagaaatca ttaaattatt   15480
aagttgtaca ataaaa                                                  15496
```

SKIN CARE COMPOSITION AND METHOD OF USING THE SAME

FIELD

The present disclosure is directed generally to skin care compositions and methods for improving cellular energy levels and renewing the extracellular matrix. More specifically, the present invention is directed to a combination of peptides that synergistically modulate certain genes involved in cellular energy production and extracellular matrix repair.

BACKGROUND

Skin is the first line of defense against environmental insults that would otherwise damage sensitive underlying tissue and organs, and skin plays a key role in a person's physical appearance. The tell-tale signs of skin aging, such as wrinkles and age spots on the skin, are an undesirable reminder of the disappearance of youth. As a result, treating the signs of aging in skin has become a booming business in youth-conscious societies.

Skin is made up of a variety of different cells that function together in a dynamic, complex relationship to maintain the health of the skin. However, as skin cells age or become damaged, they can lose their ability to function at the level needed to maintain young, healthy looking skin. Skin cells can be damaged by a variety of endogenous and exogenous stressors (e.g., ultraviolet radiation, pollution, smoking). In some instances, these stressors can cause the production of reactive oxygen species (ROS), which interfere with normal cellular processes. In response, cells have evolved defenses to combat ROS, but the cell's defenses can be overwhelmed by spikes of stressor-induced ROS, leading to not just acute but also chronic alterations in cellular homeostasis. As ROS accumulate over time, they cause oxidative stress at the cellular level, which can ultimately manifest as visible signs of aging (e.g., fine lines, wrinkles, hyperpigmented spots, thinning skin).

The use of peptides in skin care compositions is generally known. The variety of commercially available peptides and the range of skin care benefits these peptides can provide make them attractive ingredients for skin care compositions. For example, U.S. Pat. No. 9,597,274 describes using peptides derived from growth factors, such as Growth Differentiation Factor 11, for improving the health and/or appearance of skin. In another example, U.S. Pat. No. 10,668,000 describes in skin care compositions that can contain a variety of different peptides that are active in the synthesis of ECM proteins and generally improve the appearance of skin. However, peptides can be expensive, especially those that are known to provide a skin care benefit. As a result, peptides are typically added to skin care compositions in relatively low amounts, and thus it can be important to select peptides that provide good efficacy at low concentrations.

Accordingly, it would be desirable to provide a peptide-containing skin care composition that can improve the health and appearance of human skin, especially skin that exhibits a visible sign of aging. In particular, it would be desirable to provide a peptide-containing skin care composition that improves cellular energy production and/or ECM repair and renewal processes in a skin cell by targeting specific genes involved in these biochemical pathways. It would further be desirable to provide a combination of peptides that provide desirable efficacy at low concentrations.

SUMMARY

Disclosed herein is a skin care composition, comprising: a combination of palmitoyl dipeptide-7 (pal-KT) and acetyl tetrapeptide-11 (ac-PPYL) [SEQ ID NO: 1]; and a dermatologically acceptable carrier. Also disclosed is a method of treating a skin condition comprising applying the novel composition herein to a target portion of skin where treatment is desired. The combination of peptides can improve cellular ATP level and/or upregulate certain genes involved in ECM repair and renewal processes, in some instances synergistically.

DETAILED DESCRIPTION

The use of peptides for improving the health and appearance of skin is generally known. However, it has now been surprisingly discovered that a combination of palmitoyl dipeptide-7 ("pal-KT") and acetyl tetrapeptide-11 (ac-PPYL) [SEQ ID NO: 1] can boost cellular energy production and ECM repair and renewal processes. In particular, select combinations of pal-KT and ac-PPYL [SEQ ID NO: 1] can synergistically modulate the expression of key genes known to be involved in cellular bioenergetics and ECM repair and renewal. Improving cellular energy production and/or ECM repair and renewal is important for improving the health and/or appearance of skin, especially skin that exhibits visible signs of aging.

Reference herein to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

SEQUENCE LISTING

A sequence listing that sets forth the amino acid or nucleotide sequences for SEQ ID NO: 1 and the nucleotide sequences for SEQ ID NOS: 2 and 3, which are primary sequences and include conservatively modified variants thereof, is being filed concurrently with the present application as an ASCII text file titled "15965_seq_list_ST25". This ASCII text file was created on Jan. 19, 2021 and is 138 KB in size. In accordance with MPEP § 605.08 and 37 CFR § 1.52(e), the subject matter in the ASCII text file is incorporated herein by reference.

Definitions

"About" modifies a particular value by referring to a range equal to plus or minus twenty percent (+/−20%) or less (e.g., less than 15%, 10%, or even less than 5%) of the stated value.

"Apply" or "application", as used in reference to a composition, means to apply or spread the compositions of the present invention onto a human skin surface such as the epidermis.

"Cosmetic composition" means a composition comprising a cosmetic agent and intended for non-therapeutic (i.e., medical) use. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Derivative," herein, means amide, ether, ester, amino, carboxyl, acetyl, and/or alcohol derivatives of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of sucrose ester and fatty alcohol is an amount sufficient to increase cellular ATP levels that have been reduced as a result of oxidative stress.

"Skin care" means regulating and/or improving a skin condition (e.g., skin health, appearance, or texture/feel). Some nonlimiting examples of improving a skin condition include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Synergy" and variations thereof mean that the cellular energy production and/or ECM repair effects provided by a combination of palmitoyl dipeptide-7 (pal-KT) and acetyl tetrapeptide-11 [SEQ ID NO: 1] is more than the predicted additive effect of these ingredients alone. For example, synergy is demonstrated when upregulation of PPARA [SEQ ID NO: 2] and/or MSMO1 [SEQ ID NO: 3] is increased by a combination of pal-KT and acetyl tetrapeptide-11 [SEQ ID NO: 2] more than the calculated additive effects of these ingredients individually.

"Treatment period," as used herein, means the length of time and/or frequency that a material or composition is applied to a target skin surface.

"Upregulation" and variations thereof mean an increase in gene expression. Conversely, "downregulation" means a decrease in gene expression. Upregulation and downregulation, with respect to a particular gene, can be determined according to the Gene Modulation Assay described in more detail below.

Skin Care Composition

The novel skin care compositions herein are intended for topical application to human skin to improve cellular energy production and/or the health of the ECM. The present skin care compositions contain a safe and effective amount of palmitoyl dipeptide-7 (pal-KT) and acetyl tetrapeptide-11 (ac-PPYL) [SEQ ID NO: 1]. An effective amount of these two ingredients in combination has been shown to upregulate PPARA [SEQ ID NO: 2] and MSMO1 [SEQ ID NO: 3], which is believed to be involved in cellular energy production. See, Lopez-Leon, S et al. "Sports genetics: the PPARA gene and athletes' high ability in endurance sports. A systematic review and meta-analysis." Biology of sport vol. 33,1 (2016): 3-6. An effective amount of pal-KT and ac-PPYL [SEQ ID NO: 1] can also synergistically upregulate MSMO1 (SEQ ID NO: 3), which is believed to be involved in cholesterol synthesis, which is involved in the repair and renewal of the skin barrier. See, He M. et al, "The role of sterol-C4-methyl oxidase in epidermal biology." Biochim Biophys Acta. 2014 March; 1841(3):331-5.

It has been shown that PPARA and MSMO1 are downregulated as a result of dermal aging in skin (i.e., chronological aging and/or photo aging of the dermis). However, in some instances the combination of pal-KT and ac-PPYL [SEQ ID NO: 1] synergistically upregulates these genes and may even exhibit a synergy of factor of 1.2 or more (e.g., 1.3, 1.4, 1.5, 1.6, 1.7, 1.8, or 1.9 or more). The compositions herein may contain a weight ratio of pal-KT to ac-PPYL [SEQ ID NO: 1] of between 10:1 and 1:10 (e.g., 5:1 to 1:10, 5:1 to 1:5, 1:1 to 1:5, or 1:1 to 1:10).

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

The compositions herein may be prepared by conventional methods of making topical skin care compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Vitamin $B_3$ Compound

The compositions herein may optionally include a safe and effective amount of a vitamin $B_3$ compound. In some instances, the present compositions may contain 0.01% to 10%, by weight, of the vitamin $B_3$ compound, based on the weight or volume of the composition (e.g., 0.1% to 10%, 0.5% to 5%, or even 1% to %).

As used herein, "vitamin $B_3$ compound" means a compound having the formula:

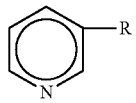

Where: R is $CONH_2$ (i.e., niacinamide), COOH (i.e., nicotinic acid) or $CH_2OH$ (i.e., nicotinyl alcohol); derivatives thereof; and salts of any of the foregoing.

Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Dipeptide

The compositions herein include a safe and effective amount of the palmitoylated dipeptide, pal-KT (INCI: Palmitoyl Dipeptide-7). In some instances, pal-KT may be present in the present compositions at 0.0001% to 3% (e.g., 0.001% to 2%, 0.01% to 1% or 0.1% to 0.5%). Pal-KT is available as Palestrina® from Sederma (France).

Tetrapeptide

The compositions herein include a safe and effective amount of the acetylated tetrapeptide, ac-PPYL [SEQ ID NO: 2] (INCI: Acetyl Tetrapeptide-11). In some instances, ac-PPYL may be present in the present composition at 0.0001% to 3% (e.g., 0.001% to 2%, 0.01% to 1% or 0.1% to 0.5%). Ac-PPYL is available as SYNIORAGE from BASF Care Creations (New Jersey).

Dermatologically Acceptable Carrier

The compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion that has a continuous aqueous phase (e.g., an oil-in-water or water-in-oil-in-water emulsion) or a continuous oil phase (e.g., water-in-oil or oil-in-water-in-oil emulsion). The oil phase of the emulsion may include silicone oils, non-silicone oils such as hydrocarbon oils, esters, ethers, and mixtures thereof. The aqueous phase may include water and water-soluble ingredients (e.g., water-soluble moisturizing agents, conditioning agents, anti-microbials, humectants and/or other skin care actives). In some instances, the aqueous phase may include components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable diluents. As used herein, "diluent" refers to materials in which the skin care actives herein can be dispersed, dissolved, or otherwise incorporated. Some non-limiting examples of hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 2,6-hexanetriol, ethanol, isopropanol, sorbitol esters, butanediol, ether propanol, ethoxylated ethers, propoxylated ethers and combinations thereof.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Rheology Modifiers

The compositions herein may include 0.1% to 5% of a rheology modifier (e.g., thickening agent) to provide the composition with suitable rheological and skin feels properties. Some non-limiting examples of thickening agents include crosslinked polyacrylate polymers, polyacrylamide polymers, polysaccharides, gums and mixtures thereof. In a particularly suitable example, the composition may include a superabsorbent polymer thickening agent such as sodium polyacrylate, starch grafted sodium polyacrylate, or a combination of these. Some non-limiting examples of superabsorbent polymer thickeners are described in, for example, U.S. Pat. No. 9,795,552.

Some consumers find compositions that use silicone fluids as conditioning agents to be undesirably greasy or heavy feeling. Thus, it may be desirable to provide a composition that is free of or substantially free of silicone fluid. It may also be desirable to tailor a superabsorbent polymer thickener to provide the composition with a light, airy feel, for example, by adjusting the amount of water in the composition, the water:oil ratio (e.g., 12:1 to 1:1), and/or the ratio of water to thickener or oil to thickener.

Emulsifiers

When the dermatologically acceptable carrier is in the form of an emulsion, it may be desirable to include an emulsifier to provide a stable composition (e.g., does not phase separate), When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition, especially pH sensitive ingredients like niacinamide, salicylates and peptides. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The present method includes identifying a target portion of skin where treatment is desired and applying a composition comprising an effective amount of vitamin $B_3$ compound, pal-KT, ac-PPYL [SEQ ID NO: 1] and, optionally, one or more additional skin care actives to the target portion of skin. The target portion of skin may be on a facial skin surface such as the forehead, perioral, chin, periorbital, nose, and/or cheek) or another part of the body (e.g., hands, arms, legs, back, chest). The person or target portion of skin in need of treatment may be one that exhibits a telltale sign of aging skin (e.g., fine lines, wrinkles, hyperpigmented spots). In some instances, a target portion of skin may not exhibit a sign of skin aging, but a user may still wish to treat the portion of skin if it is one that is known to exhibit visible signs of aging (e.g., skin that is exposed to the sun). In this way, the present methods and compositions may be used prophylactically to help delay the visible signs of skin aging.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. The treatment period herein is ideally of sufficient time for the pal-KT and ac-PPYL [SEQ ID NO: 1] to improve the appearance of the skin. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a wrinkle or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Gene Modulation Assay

This method provides a way to measure the ability of a compound or material to modulate the expression of a target gene such as PPARA [SEQ ID NO: 2] or MSMO1 [SEQ ID NO: 3].
Cells: tert keratinocytes (tKC)
BJ Fibroblasts
Plating: Cells are plated the day before treatment.
For tert keratinocytes: 100,000 cells/well in 2 ml volume of medium/well for 12-well plates (e.g., Collagen I coated plates, Corning cat #356500), or 50,000 cells/well in 1 ml volume of medium/well for 24-well plates.
For BJ fibroblasts: 88,000 cells/well in 2 ml volume of medium/well for 12-well plates (e.g., Corning cat #3512), or 44,000 cells/well in 1 ml volume of medium/well for 24-well plates.
Medium: For tert keratinocytes: EpiLife (e.g., Thermo Fisher Scientific cat #MEPI500CA+HKGS (e.g., Thermo Fisher Scientific cat #S-001-5).
For BJ Fibroblasts: EMEM (e.g., ATCC cat #30-2003)+ 10% FBS (e.g., HyClone cat #SH30071.02).
Treatments are made in media and aliquoted to dose plates. When it is time to treat cells, all plates of cells are removed from the incubator at the same time. Working with one plate at a time, media is removed and treatment is added, as follows:
Media is decanted from plate of cells.
Inverted plate is blotted briefly on paper towels.
Lid is put back onto plate and plate is moved into biosafety cabinet.
Treatments are transferred from dose plate to plate of cells, one column at a time, using a multichannel pipette.
Once all plates have been treated, they are moved into incubator at 37° C., with 5% $CO_2$ and 90% humidity. About 15-30 min before the end of the treatment period, cells from representative wells of each treatment are observed via microscope, then plates are returned to the incubator. When treatment time is complete, all plates are removed from incubator. Media is decanted from each plate, and plates are blotted on paper towels. 350 ul Qiagen Buffer RLT is added to each well to lyse cells, and lysates are transferred to 2 ml Eppendorf tubes and stored at −20° C. until ready for genomics.

Wafergen Process: Total RNA Purification and qPCR

Cell lysates are thawed at 4° C. and then isolated using the Biomek FxP and the RNAdvance Tissue Isolation kit (Beckman Coulter, p/n A32646). The resulting RNA is quantified using the Nandrop 8000 (Nanodrop, ND-8000). cDNA is generated using 500 ng of Total RNA and Applied Biosystems High Capacity cDNA with Reverse Transcription kit (Applied Biosystems p/n 4368814). cDNA, assays, and dilutions of PrimeTime GeneExpression MasterMix (IDT, p/n 1055771) are plated onto a Wafergen MyDesign SmartChip (TakaraBio, p/n 640036) using the Wafergen Nanodispenser. The chip is then loaded into the SmartChip cycler and qPCR performed using the following PCR conditions:
Hold stage: 50° C. for 2 minutes (warm up), then 95° C. for 10 minutes.
PCR stage (40 cycles): 95° C. for 15 seconds, then 60° C. for 1 minute.
Export data in .txt file format for analysis.

Hydrogen Peroxide Stressed ATP Assay

Skin Cells (e.g., keratinocytes and fibroblasts) fight reactive oxygen species by using energy to generate enzymes and reducing equivalents (e.g., GSH), which causes a depletion of cellular ATP levels. Lower energy levels leave the cells susceptible to decreased ability to adapt and function normally. Thus, increasing cellular ATP levels may help the cells fight off stress and maintain sufficient energy for normal homeostasis.
Hydrogen peroxide is a well-known surrogate for ROS. When skin cells are treated with high levels (e.g., 200-500 uM) of hydrogen peroxide, a decrease of about 10% in cellular ATP level is observed in non-stressed cells in an hour. Cellular ATP levels can be quantitated with a CELL TITER GLO brand assay kit from Promega, or equivalent, in which a luminescence signal is proportional to the quantity of ATP present.
Summary of Method:
The assay is performed using expanded tKCs from storage stocks. The cells are expanded over 5 days in culture flasks, trypsinized, seeded and then grown in 96-well plates. After growing for 1 day in 96-well plates, column 1 cells are not treated nor stressed, columns 2-12 of the cells are treated with hydrogen peroxide (300 uM in media), column 2 is not treated with test materials while columns 3-12 are treated with serial dilutions of test materials for 1 hour (37° C., 5% $CO_2$ incubator).
Cell Preparation:
1. Seed cells at 10,000 cells/well in 100 uL total volume/ well in suitable 96-well plates (e.g., CORNING brand white, clear bottom plates, #3903 or equivalent).
2. Incubate cells for 24 hours at 37° C., 5% $CO_2$, 95% humidity until treatment day. For example, cells can be seeded on Monday and assayed on Tuesday.
Treatment:
1. Aspirate the media from the cell plates.
2. Add 100 uL medium to column 1 wells A1-H1.
3. Add 100 uL medium containing 300 uM hydrogen peroxide to all wells in columns 2-12.
4. Add vehicle control to column 2 (A2-H2) and 1 uL of serial dilutions of treatments to columns 3-11.
5. Add 1 ul of 40.9 mM niacinamide to all wells in column 12 making final level of niacinamide 409 uM (positive control).
6. Place in 37° C., 5% $CO_2$ incubator for 1 hour.
7. Aspirate media from all wells.
8. Add 100 uL of CELL TITER GLO brand reagent to each well per manufacturer instructions.
9. Incubate at room temperature for 5-10 minutes.
10. Read luminescence on a suitable plate reader.

Luminescence Detection:
Use SYNERGY NEO brand plate reader from BioTek or equivalent.

EXAMPLES

Example 1: Formulations

Table 1 below provides examples of the present skin care compositions. The exemplary compositions are made by blending the A phase components with a suitable mixer (e.g., Tekmar RW20DZM or equivalent) and heating to a temperature of 70-80° C. and maintaining the temperature while stirring. Separately, the B phase components are blended with a suitable mixer and heated to 70-75° C., while maintaining temperature during mixing. Phase B is added to Phase A while mixing well to form an oil-in-water (O/W) emulsion. The emulsion is then milled using a suitable mill (e.g., Tekmar T-25 or equivalent) for 5 minutes. When the emulsion is at 60° C., phase C is added while continuing to mix. At 40° C., the ingredients of phase D and E are added to the emulsion. The emulsion is then milled for 5 minutes to provide a uniform composition.

TABLE 1

| Component | I | II | III | IV | V | VI | VII | VIII | IX |
|---|---|---|---|---|---|---|---|---|---|
| Phase A | | | | | | | | | |
| Water | qs | qs | qs | qs | qs | qs | qs | qs | qs |
| Glycerol | 5.00 | 7.00 | 3.00 | 15.0 | 7.00 | 5.00 | 5.00 | 3.00 | 5.00 |
| Disodium EDTA | 0.10 | 0.05 | 0.10 | 0.10 | 0.05 | 0.05 | 0.05 | 0.05 | 0.10 |
| Phase B | | | | | | | | | |
| Dimethicone 5 cSt | — | — | — | — | — | — | — | 10.0 | 15.0 |
| Dimethicone and Dimethicone Crosspolymer | — | — | — | — | — | — | — | 13.0 | 15.0 |
| Laureth-4 | — | — | — | — | — | — | — | 0.25 | 0.35 |
| Polysorbate 20 | — | — | — | — | — | — | — | 0.15 | 0.25 |
| Tapioca Starch and Polymethylsilsesquioxane | — | — | — | — | — | — | — | 2.50 | 3.50 |
| Avobenzone | — | — | — | 3.00 | — | 3.00 | — | — | — |
| Homosalate | — | — | — | 15.0 | — | 10.0 | — | — | — |
| Octisalate | — | — | — | 5.00 | — | 5.00 | — | — | — |
| Octocrylene | — | — | — | 2.60 | — | 9.00 | — | — | — |
| Isopropyl Isostearate | 5.00 | 2.50 | 1.00 | — | — | — | — | — | — |
| Isohexadecane | 1.00 | 1.50 | 3.00 | — | — | — | — | — | — |
| Cetyl Alcohol | 0.25 | 0.50 | 0.32 | 0.40 | 0.40 | 0.30 | 0.50 | — | — |
| Tocopherol Acetate | — | 0.50 | 0.25 | 1.00 | 0.25 | 0.25 | 0.25 | — | — |
| PEG-100 Stearate | 0.20 | 0.10 | 0.10 | 0.30 | 0.10 | 0.20 | 0.10 | — | — |
| Stearyl Alcohol | 0.50 | 1.50 | 0.40 | 0.60 | 0.50 | 0.40 | 0.60 | — | — |
| Behenyl Alcohol | 0.40 | 1.00 | 0.50 | 0.50 | 0.40 | 0.35 | 0.50 | — | — |
| Ethyl Paraben | 0.20 | 0.15 | 0.20 | 0.25 | — | — | — | — | — |
| Propyl Paraben | 0.10 | 0.15 | 0.10 | 0.15 | — | — | — | — | — |
| Polymethylsilsesquioxane | 1.25 | 2.50 | 1.00 | — | — | — | — | — | — |
| Phase C | | | | | | | | | |
| Titanium Dioxide | — | 0.50 | — | 0.25 | — | — | — | — | — |
| Tapioca Starch and Polymethylsilsesquioxane | — | — | — | — | — | 12.0 | — | — | — |
| Vinyl Dimethicone/Methicone Silsesquioxane Crosspolymer | 1.50 | — | 1.50 | 3.50 | 5.00 | — | 7.50 | — | — |
| Sodium Polyacrylate Starch | — | 1.50 | — | — | 1.50 | 1.00 | 1.50 | — | — |
| Hydroxyethyl acrylate/sodium acryloyldimethyltaurate copolymer | 2.00 | 1.50 | 2.50 | 2.00 | — | — | — | 1.25 | 2.00 |
| Phase D | | | | | | | | | |
| Water | 5 | 10 | 10 | 5 | 10 | 10 | 10 | 5 | 10 |
| Pal-KT | 0.00005 | 1 | 0.5 | 0.1 | 0.05 | 0.025 | 0.01 | 0.005 | 0.0005 |
| Ac-PPYL | 0.00005 | 1 | 5 | 1 | 0.1 | 0.005 | 0.05 | 0.0005 | 0.005 |
| Niacinamide | 3.5 | — | 3.5 | — | 4 | 5 | — | — | 2 |
| Dexpanthenol | 0.5 | 0.5 | 0.5 | 1 | 1 | 1.5 | 0.25 | 1 | 0.5 |
| Phase E | | | | | | | | | |
| Benzyl alcohol | 0.25 | 0.40 | 0.25 | 0.50 | — | — | — | — | — |
| Hexanediol and Caprylyl Glycol | — | — | — | — | 0.70 | 0.80 | 0.70 | 0.70 | 1.00 |
| Phenoxyethanol | — | — | — | — | 0.3 | 0.4 | 0.5 | 0.20 | 0.25 |
| Dimethicone/dimethiconol | 0.5 | 1.00 | 2.00 | 1.00 | 2.00 | 2.00 | 1.00 | 1.75 | 1.00 |

Example 2: pal-KT and Ac-PPYL [SEQ ID NO: 1] Synergistically Upregulate PPARA [SEQ ID NO: 2] and MSMO1 [SEQ ID NO: 3]

This example demonstrates the ability of a combination of pal-KT and ac-PPYL [SEQ ID NO: 1] to synergistically upregulate PPARA [SEQ ID NO: 2]. Test compositions and control compositions were prepared as described above in the Gene Modulation Assay and tested accordingly. The pal-KT used in this example is PALESTRINA brand pal-KT from Sederma (France), and the ac-PPYL is SYNIORAGE brand tetrapeptide from BASF Care Creations (New Jersey). The results of the test are summarized below in Table 2. P+A refers to the combination of pal-KT (P), and ac-PPYL (A) [SEQ ID NO: 1].

Synergy Factor is calculated as:

$$\frac{\text{Observed response for the combination of ingredients}}{\text{Sum of the individual ingredient responses}}$$

A synergy factor greater than 1.00 with p-value ≤0.05 indicates a statistically significant synergistic effect. Preferred synergy factors are 1.3 or greater.

TABLE 2

| Peptide amount (ppm) | | | Fold change vs. control | | | | | |
|---|---|---|---|---|---|---|---|---|
| Pal-KT | Ac-PPYL | Biomarker | Pal-KT | Ac-PPYL | P + A (expected) | P + A (observed) | Synergy factor | P-value |
| 15 | 40.5 | MSMO1 | 5.63 | 0.560 | 9.62 | 3.15 | 3.06 | 4.46E−14 |
| 15 | 13.5 | MSMO1 | 5.63 | 0.510 | 5.84 | 2.87 | 2.04 | 1.14E−07 |
| 15 | 1 | MSMO1 | 5.63 | 0.496 | 5.25 | 2.79 | 1.88 | 1.71E−06 |
| 15 | 0.0135 | MSMO1 | 5.63 | 0.377 | 4.26 | 2.12 | 2.01 | 1.86E−07 |
| 7.5 | 40.5 | MSMO1 | 4.69 | 0.560 | 7.49 | 2.62 | 2.86 | 3.61E−12 |
| 7.5 | 13.5 | MSMO1 | 4.69 | 0.510 | 5.01 | 2.39 | 2.10 | 1.31E−07 |
| 7.5 | 1 | MSMO1 | 4.69 | 0.496 | 3.41 | 2.32 | 1.47 | 2.28E−03 |
| 7.5 | 0.0135 | MSMO1 | 4.69 | 0.377 | 2.58 | 1.77 | 1.46 | 8.57E−03 |
| 1 | 40.5 | MSMO1 | 4.32 | 0.560 | 6.24 | 2.42 | 2.58 | 2.63E−09 |
| 1 | 13.5 | MSMO1 | 4.32 | 0.510 | 2.27 | 2.20 | 1.03 | 8.11E−01 |
| 1 | 1 | MSMO1 | 4.32 | 0.496 | 2.50 | 2.14 | 1.17 | 2.15E−01 |
| 1 | 0.0135 | MSMO1 | 4.32 | 0.377 | 1.84 | 1.63 | 1.13 | 3.54E−01 |
| 15 | 40.5 | PPARA | 1.59 | 0.71 | 2.09 | 1.13 | 1.85 | 1.33E−03 |
| 15 | 13.5 | PPARA | 1.59 | 0.67 | 1.79 | 1.07 | 1.67 | 6.02E−03 |
| 15 | 1 | PPARA | 1.59 | 0.69 | 2.54 | 1.09 | 2.33 | 1.23E−05 |
| 15 | 0.0135 | PPARA | 1.59 | 0.70 | 1.60 | 1.11 | 1.44 | 4.98E−02 |
| 7.5 | 40.5 | PPARA | 1.43 | 0.71 | 0.94 | 1.02 | 0.93 | 6.96E−01 |
| 7.5 | 13.5 | PPARA | 1.43 | 0.67 | 1.35 | 0.96 | 1.40 | 7.97E−02 |
| 7.5 | 1 | PPARA | 1.43 | 0.69 | 1.18 | 0.98 | 1.21 | 2.97E−01 |
| 7.5 | 0.0135 | PPARA | 1.43 | 0.70 | 1.15 | 1.00 | 1.15 | 5.04E−01 |
| 1 | 40.5 | PPARA | 1.26 | 0.71 | 1.09 | 0.90 | 1.22 | 3.61E−01 |
| 1 | 13.5 | PPARA | 1.26 | 0.67 | 0.81 | 0.85 | 0.95 | 7.93E−01 |
| 1 | 1 | PPARA | 1.26 | 0.69 | 0.86 | 0.86 | 1.00 | 9.79E−01 |
| 1 | 0.0135 | PPARA | 1.26 | 0.70 | 0.63 | 0.88 | 0.72 | 9.12E−02 |

As can be seen in Table 2, not all combinations of pal-KT and ac-PPYL [SEQ ID NO: 1] yield the desired synergistic effect Test sample combinations containing 1 ppm pal-KT at a ratio of pal-KT to tetrapeptide of 1:13.5 to 100:1.35 did not exhibit a synergy factor of 1.3 or greater for upregulating MSMO1 [SEQ ID NO: 3]. Test sample combinations containing 7.5 ppm pal-KT only exhibited the desired synergy to upregulate PPARA [SEQ ID NO: 2] at a ratio of about 1:2, even though other combinations exhibited a lesser ability to synergistically upregulate PPARA [SEQ ID NO: 2]. Only one of the test samples containing 1 ppm were able to synergistically upregulate PPARA [SEQ ID NO: 2] and none of the test samples exhibited a synergy factor of 1.3 or greater. Thus, the data suggest that both the concentration of peptide and the ratio of the peptide can be important for upregulating PPARA [SEQ ID NO: 2] and MSMO1 [SEQ ID NO: 3].

Example 3: Pal-KT and Ac-PPYL [SEQ ID NO: 3] Improve Cellular Bioenergetics

This example demonstrates the ability of pal-KT and ac-PPYL [SEQ ID NO: 3] to combat ROS-induced ATP depletion. Test cells exposed to hydrogen peroxide, a well-known reactive oxygen species, will generally exhibit reduced ATP levels. Test agents that can restore ATP levels depleted by exposure to the ROS are desirable. Test agents that can synergistically restore ATP levels and exhibit a synergy factor of 1.3 or greater are preferred. The peptides were tested according to the Hydrogen Peroxide Stressed ATP assay above. The results of the test are summarized below in Table 3. A synergy factor greater than 1.00 with p-value ≤0.05 indicates a statistically significant synergistic effect. Preferred synergy factors are 1.3 or greater.

TABLE 3

ROS-induced ATP restoration

| Ratio of pal-KT to ac-PPYL | Luminescence P + A (measured) | Luminescence P + A (calculated) | Synergy factor | p-value |
|---|---|---|---|---|
| 100:1 | 18655 | 19547 | 0.95 | 0.4508 |
| 10:1 | 18271.33 | 19529 | 0.94 | 0.0810 |
| 1:1 | 16946.33 | 10547 | 1.61 | 0.0004 |
| 1:10 | 13446 | 9390 | 1.43 | 0.0076 |
| 1:100 | 12044 | 12156.33 | 0.99 | 0.7825 |

As can be seen in Table 3, not all combinations of pal-KT and ac-PPYL [SEQ ID NO: 1] can synergistically restore ROS-depleted ATP levels in a cell. Indeed, only combinations containing pal-KT and ac-PPYL at a ratio of between about 10:1 and 1:10 were able to synergistically increase ATP production. In this example, test samples with a ratio of pal-KT to ac-PPYL [SEQ ID NO: 1] of about 1:1 appear to exhibit the highest synergy factor.

Example 4: Dipeptide Specificity

This example demonstrates the importance of selecting a specific dipeptide to provide the desired synergistic upregulation of PPARA [SEQ ID NO: 2] and/or MSMO1 [SEQ ID NO: 3]. In this test, the amino acids from pal-KT were rearranged to form a new dipeptide, pal-TK. Test compositions and control compositions were prepared as described above in the Gene Modulation Assay and tested accordingly. The results of the test are summarized in Table 4 below. Fold change factor is calculated as.

$$\frac{\text{fold change of } pal-KT + \text{ac}-PPYL}{\text{fold change of } pal-TK + \text{ac}-PPYL}$$

A fold change factor of greater than 1 is desired, and a fold change factor of 1.3 or greater is preferred.

Surprisingly, pal-KT was able to upregulate PPARA [SEQ ID NO: 2] and MSMO1 [SEQ ID NO: 3] significantly better than pal-TK and exhibited a fold change factor of greater than 1.3 for upregulating both PPARA [SEQ ID NO: 2] and MSMO1 [SEQ ID NO: 3]

TABLE 4

Specificity of pal-KT to pal-TK

| Biomarker | Fold change vs. control (all peptides at 1 ppm) | | Fold change factor | p-value |
| --- | --- | --- | --- | --- |
| | pal-KT + ac-PPYL | pal-TK + ac-PPYL | | |
| PPARA | 1.56 | 1.04 | 1.50 | 2.54E–05 |
| MSMO1 | 2.34 | 1.32 | 1.78 | 4.06E–07 |

Surprisingly, as can be seen in Table 4, a dipeptide with the same amino acids as pal-KT, but arranged in a different order, does not provide the desired synergistic effect. These data suggest that the specific peptide sequence is important for providing the desired synergy.

Example Combinations

A. A skin care composition, comprising:
  a) a combination of palmitoyl dipeptide-7 (pal-KT) and acetyl tetrapeptide-11 (ac-PPYL) [SEQ ID NO: 1], wherein the combination of pal-KT and ac-PPYL [SEQ ID NO: 1] upregulates at least one of PPARA (SEQ ID NO: 2) and MSMO1 (SEQ ID NO: 3); and
  b) a dermatologically acceptable carrier.
B. The composition of paragraph A, wherein the combination of pal-KT and ac-PPYL [SEQ ID NO: 1] synergistically upregulates at least one of PPARA (SEQ ID NO: 2) and MSMO1 (SEQ ID NO: 3).
C. The composition of paragraph A or B, wherein the combination of pal-KT and ac-PPYL [SEQ ID NO: 1] exhibits a synergy factor of at least 1.3.
D. The composition of any preceding paragraph, wherein the pal-KT is present at 0.00005% to 5%.
E. The composition of any preceding paragraph, wherein the ac-PPYL [SEQ ID NO: 1] is present at 0.00005% to 5%.
F. The composition of any preceding paragraph, wherein the pal-KT and ac-PPYL [SEQ ID NO: 1] are present at a ratio of between 10:1 and 1:10.
G. The composition of any preceding paragraph, further comprising at least one additional ingredient selected from vitamins, minerals, peptides, sugar amines, sunscreen agents, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, pH adjustors, thickening agents, preservatives, and combinations thereof.
H. The composition of paragraph G, wherein the additional ingredient comprises a vitamin B3 compound, a vitamin A compound, a vitamin E compound, a saccharide, or a botanical extract.
I. A method of cosmetically treating skin, comprising:
  a) identifying a target portion of skin where treatment is desired; and
  b) applying the skin care composition of any preceding paragraph to the target portion of skin over the course of a treatment period, the skin care composition comprising a combination of palmitoyl dipeptide-7 (pal-KT) and acetyl tetrapeptide-11 (ac-PPYL) [SEQ ID NO: 1]) and a dermatologically acceptable carrier.
J. The method of paragraph I, wherein the combination of pal-KT and ac-PPYL [SEQ ID NO: 1] upregulates at least one of PPARA [SEQ ID NO: 2] and MSMO1 [SEQ ID NO: 3], preferably the combination of pal-KT and ac-PPYL [SEQ ID NO: 1] synergistically upregulates at least one of PPARA [SEQ ID NO: 2] and MSMO1 [SEQ ID NO: 3].
K. The method of paragraph I, wherein the combination of pal-KT and ac-PPYL [SEQ ID NO: 1] improves cellular ATP level, preferably synergistically improves cellular ATP level, according to the Hydrogen Peroxide Stressed ATP assay.
L. The method of paragraph I, wherein the treatment period is at least 2 weeks.
M. The method of paragraph, wherein the method improves a visible sign of skin aging.
N. A method of synergistically upregulating at least one of PPARA [SEQ ID NO: 2] and MSMO1 [SEQ ID NO: 3] in a skin cell, comprising: contacting a skin cell with an effective amount of pal-KT and ac-PPYL [SEQ ID NO: 1] in combination, wherein the effective amount of pal-KT and ac-PPYL [SEQ ID NO: 1] upregulates at least one of PPARA [SEQ ID NO: 2] and MSMO1 [SEQ ID NO: 3].

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition, comprising:
   a) a combination of palmitoyl dipeptide-7 (pal-KT) and acetyl tetrapeptide-11 (ac-PPYL) [SEQ ID NO: 1]; and
   b) a dermatologically acceptable carrier; wherein the combination of pal-KT and ac-PPYL synergistically improves cellular ATP level according to the Hydrogen Peroxide Stressed ATP assay: wherein the pal-KT and ac-PPYL [SEQ ID NO: 1] are present at a ratio of between about 10:1 and 1:10.

2. The composition of claim 1, wherein the combination exhibits a synergy factor of at least 1.3.

3. The composition of claim 1, wherein the pal-KT is present at about 0.00005% to about 5%.

4. The composition of claim 1, wherein the ac-PPYL [SEQ ID NO: 1] is present at about 0.00005% to about 5%.

5. A method of cosmetically treating skin, comprising:
   a) identifying a target portion of skin where treatment is desired; and
   b) applying the composition of claim 1.

6. The method of claim 5, wherein the combination exhibits a synergy factor of at least 1.3.

7. The method of claim 5, wherein the pal-KT is present at about 0.00005% to about 5%.

8. The method of claim 5, wherein the ac-PPYL [SEQ ID NO: 1] is present at about 0.00005% to about 5%.

9. The method of claim 5, wherein the treatment period is at least 2 weeks.

10. The method of claim 1, wherein the combination exhibits a synergy factor of at least 1.00.

11. The method of claim 1, wherein the pal-KT and ac-PPYL [SEQ ID NO: 1] are present at a ratio of about 1:1.

12. The method of claim 1, wherein the pal-KT and ac-PPYL [SEQ ID NO: 1] are present at a ratio of between about 5:1 and 1:5.

* * * * *